United States Patent
Jennewein et al.

(10) Patent No.: US 12,060,593 B2
(45) Date of Patent: Aug. 13, 2024

(54) FUCOSYLTRANSFERASES AND THEIR USE IN PRODUCING FUCOSYLATED OLIGOSACCHARIDES

(71) Applicant: Chr. Hansen HMO GmbH, Rheinbreitbach (DE)

(72) Inventors: Stefan Jennewein, Bad Honnef (DE); Katja Parschat, Bonn (DE)

(73) Assignee: Chr. Hansen HMO GmbH, Rheinbreitbach (DE)

( * ) Notice: Subject to any disclaimer, the term of this patent is extended or adjusted under 35 U.S.C. 154(b) by 0 days.

(21) Appl. No.: 16/628,516

(22) PCT Filed: Jul. 6, 2018

(86) PCT No.: PCT/EP2018/068356
§ 371 (c)(1),
(2) Date: Jan. 3, 2020

(87) PCT Pub. No.: WO2019/008133
PCT Pub. Date: Jan. 10, 2019

(65) Prior Publication Data
US 2020/0181665 A1    Jun. 11, 2020

(30) Foreign Application Priority Data

Jul. 7, 2017 (EP) .................................... 17180176

(51) Int. Cl.
| | | |
|---|---|---|
| *C12P 19/18* | (2006.01) | |
| *A23L 33/00* | (2016.01) | |
| *A23L 33/125* | (2016.01) | |
| *A23L 33/21* | (2016.01) | |
| *C12N 1/21* | (2006.01) | |
| *C12N 9/10* | (2006.01) | |
| *C12N 15/63* | (2006.01) | |

(52) U.S. Cl.
CPC .............. *C12P 19/18* (2013.01); *A23L 33/125* (2016.08); *A23L 33/21* (2016.08); *A23L 33/40* (2016.08); *C12N 9/1051* (2013.01); *C12N 15/63* (2013.01); *C12Y 204/01065* (2013.01)

(58) Field of Classification Search
None
See application file for complete search history.

(56) References Cited

U.S. PATENT DOCUMENTS

| | | | | |
|---|---|---|---|---|
| 2017/0081353 A1* | 3/2017 | McCoy | .......... | C12Y 204/01069 |
| 2017/0204443 A1* | 7/2017 | Baumgartner | ....... | C12Y 204/01 |
| 2018/0371432 A1* | 12/2018 | Chen | ....... | C12P 19/26 |

FOREIGN PATENT DOCUMENTS

| | | | | |
|---|---|---|---|---|
| JP | 2012529274 A | 11/2012 | | |
| JP | 2017509346 A | 4/2017 | | |
| KR | 1020170028438 A | 3/2017 | | |
| RU | 2013138474 A | 2/2015 | | |
| RU | 2584599 C2 | 5/2016 | | |
| WO | 2010070104 A1 | 6/2010 | | |
| WO | 2010142305 A1 | 12/2010 | | |
| WO | 2012097950 A1 | 7/2012 | | |
| WO | 2015036138 A1 | 3/2015 | | |
| WO | 2015150328 A1 | 10/2015 | | |
| WO | 2016008602 A1 | 1/2016 | | |
| WO | 2016040531 A1 | 3/2016 | | |
| WO | WO-2016040531 A * | 3/2016 | .............. | C07H 3/06 |
| WO | 2017106864 A1 | 6/2017 | | |

OTHER PUBLICATIONS

GenBank, Accession No. WP_013031010.1, 2016, www.ncbi.nlm.gov. (Year: 2016).*
Baumgartner et al., Synthesis of fucosylated lacto-N-tetraose using whole-cell biotransformation, Bioorganic Medicinal Chem. 23, 2015, 6799-6806. (Year: 2015).*
Engels et al., WbgL: a novel bacterial α1,2-fucosyltransferase for the synthesis of 2'-fucosyllactose, Glycobiology 24, 2014, 170-78. (Year: 2014).*
Wahl et al., Molecular Hybridization of Immobilized Nucleic Acids: Theoretical Concepts and Practical Considerations, Methods Enz . 152, 1987, 399-407. (Year: 1987).*
Dumon et al., "In vivo fucosylation of lacto-N-neotetraose and lacto-N-neohexaose by heterologous expression of Helicobacter pylori alpha-1,3 fucosyltransferase in engineered *Escherichia coli*", Glycoconjugate Journal, Chapman & Hall, Boston, vol. 18, No. 6, Jan. 1, 2001 (Jan. 1, 2001), XP002380631, pp. 465-474.
Drouillard et al., "Large-Scale Synthesis of H-Antigen Oligosaccharides by Expressing Helicobacter pylori [alpha] 1,2-Fucosyltransferase in Metabolically Engineered *Escherichia coli* Cells", Angewandte Chemie International Edition, vol. 45, No. 11, Mar. 6, 2006, XP055105681, pp. 1778-1780.
Gunn, F.J. et al., "Identification of a novel sugar-H+ symport protein, FucP, for transport of L-fucose into *Escherichia coli*," Mol. Microbiol., 1994, 12:799-809 (abstract only), 1 page.

* cited by examiner

*Primary Examiner* — Todd M Epstein

(57) ABSTRACT

Fucosyltransferases capable of transferring a fucose residue from a donor substrate to a lactotetraose, methods for producing fucosylated oligosaccharides utilizing the fucosyltransferases, and the use of the thus produced fucosylated oligosaccharides for manufacturing nutritional compositions are provided.

12 Claims, 6 Drawing Sheets
Specification includes a Sequence Listing.

FUCOSYLTRANSFERASES AND THEIR USE IN PRODUCING FUCOSYLATED OLIGOSACCHARIDES

CROSS-REFERENCE TO RELATED APPLICATIONS

This application is the National Stage entry of International Application No. PCT/EP2018/068356, filed 6 Jul. 2018, which claims priority to European Patent Application No. 17180176.4, filed 7 Jul. 2017.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_3000045-009000_ST25.txt" created on 2 Jan. 2020 and 143,967 bytes in size) is submitted concurrently with the instant application, and the entire contents of the Sequence Listing are incorporated herein by reference.

BACKGROUND

Field

The present invention relates to novel fucosyltransferases and their use in producing fucosylated oligosaccharides.

Description of Related Art

Approximately 200 structurally distinct human milk oligosaccharides (HMOs) have been identified so far. Said HMOs are based on the disaccharide lactose and bear additional monosaccharide residues which are based on N-acetyl-glucosamine, fucose, sialic acid, and galactose. The concentration and composition of HMOs in human milk varies between individuals and during the lactation period from up to 20 g/L in the colostrum to 5-10 g/L in the mature milk.

Milk of women belonging to the so-called "secretor phenotype" contains a high content of α-1,2-fucosylated HMOs. These women express the FUT2 gene encoding the so-called "fucosyltransferase 2". The most abundant HMOs in their milk are 2'-fucosyllactose (2'-FL; Fuc(α1-2)Gal(β1-4)Glc) and Lacto-N-fucopentaose-I (LNPF-I; Fuc(α1-2) Gal (β1-3)GlcNAc(β1-3)Gal(β1-4)Glc).

Human milk oligosaccharides are not digested during their transit through the intestine of infants. Due to their persistence in the infant's gut, they exhibit beneficial effects to the children. More specifically, HMOs have been shown to be prebiotic as they serve as carbon source for commensal microorganisms of the genera *Bifidobacterium, Bacteroides* and *Lactobacillus*. Therefore, HMOs support proliferation of these microorganisms in infants' guts.

Human milk oligosaccharides also directly reduce colonization of the infant's gut by pathogens in that they prevent adherence of said pathogens to glycan structures on the gut's mucosal surface. The HMOs function as a decoy due to their structural similarity to epithelial surface glycans and inhibit invasion of the pathogens thereby reducing the risk of infections.

Alpha-1,2-fucosylated HMOs have been shown to be protective against infections with *Campylobacter jejuni*, the causative agent of most common bacterial diarrheas. The α-1,2-fucosylated HMOs are also associated with protection against diarrhea caused by the heat stable toxin of *Escherichia coli*. Also, the risk of infections with diarrhea-mediating caliciviruses is reduced by a high content of α-1,2-fucosylated HMOs in breast milk. HMOs, especially the fucosylated HMO Lacto-N-fucopentaose V (LNFP-V; Gal (β1-3)GlcNAc (β1-3)Gal(β1-4)[Fucα1-3]Glc), bind(s) to the carbohydrate binding site of toxin A from *Clostridium difficile*, the most common cause of nosocomial diarrhea. Thus, HMOs seem to prevent the interaction of toxin A from *C. difficile* with cellular receptors. Furthermore, adherence of *Pseudomonas aeruginosa* to epithelial cells was significantly inhibited by 2'-FL and 3-fucosyllactose (3-FL; Gal (β1-4)[Fucα1-3]Glc). Binding of noroviruses (Norwalk-like viruses, NLV), the main cause of acute gastro-enteritis, to histo-blood group antigens is prevented by α-1,2-fucosylated HMOs as well as by α-1,3-fucosylated HMOs. This indicates the potential of these HMOs to inhibit norovirus capsid-binding to host receptor glycans.

Due to the known benefits of HMOs, and especially of fucosylated HMOs, an economically worthwhile process for their synthesis is desired. Biotechnological processes for producing HMOs utilizing bacteria which were metabolically engineered have been described. Several fructosyltransferases have been described for producing fucosylated oligosaccharides by genetically engineered bacteria.

For producing 2'-fucosyllactose (2'-FL), the α-1,2-fucosyltransferases WbgL from *E. coli* O126 and FucT2 from *Helicobacter pylori* (EP 2 479 263 B1), the α-1,2-fucosyltransferases WblA from *Vibrio cholera* O22, FutD from *H. bilis* ATCC 437879, FutE from *H. cinaede* CCUG 18818, FutN from *Bacteroides vulgatus* ATCC 8482, FutO from *Bacteroides ovatus* ATCC 8483, WbgN from *E. coli* O55: H7, Bft1 and Bft3 from *Bacteroides fragilis* NCTC 9343 (WO 2014/018596 A2), and the α-1,2-fucosyltransferases FucT2 from *H. pylori* for the synthesis of Lewis Y and Lewis B saccharides (U.S. Pat. No. 6,670,160 B2) were described.

For producing 3-fucosyllactose, the α-1,3-fucosyltransferase Amuc from *Akkermansia muciniphila*, and FucT6 and FucT7 from *Bacteroides fragilis* (EP 2 439 264 A1), the α-1,3-fucosyltransferase FutA from *H. pylori* (US 2014/0120611 A1) are described. In addition, WO 2016/040531 A1 discloses the α-1,3-fucosyltransferase CafC from *B. nordii* CL02T12C05 for the synthesis of 3-fucosyllactose and lactodifucotetraose, and CafD from *H. hepaticus* ATCC51449 for the production of LNnFP-III.

However, it is known in the art that glycosyltransferases including fucosyltransferases can vary greatly in terms of kinetics, substrate specificity, affinity for donor substrates and acceptor molecules, stability and solubility. In addition, the choice of a fucosyltransferase for mediating a desired fucosylation reaction significantly affects the final yield of the desired fucosylated oligosaccharide. For example, WO 2014/018596 A1 teaches that *E. coli* producing WbgL synthesized 2'-FL and was also able to synthesize lactodifucotetraose (LDFT), whereas *E. coli* producing WbsJ from *E. coli* or WblA from *V. cholerae* were able to promote 2'-FL synthesis but did not synthesize LDFT.

In addition, production of more complex fucosylated oligosaccharides such as fucosylated tetrasaccharides, fucosylated pentasaccharides, fucosylated hexasaccharides or even fucosylated heptasaccharides is known in small-scale only.

In view of these drawbacks, there is a need for additional fucosyltransferases with faster kinetics, greater affinity for nucleotide sugar donors and/or different specificities for acceptor molecules. There is a particular need of fucosyltransferases which can be employed in the commercial production of complex fucosylated human milk oligosaccharides, i.e. of fucosyltransferases which are capable of fucosylating tri-, tetra-, penta- or even hexasaccharides and/or possess sufficient activity for obtaining commercially worthwhile amounts of the desired fucosylated oligosaccharide.

In an attempt to solve this problem, the inventors searched protein databases and nucleotide sequence databases for entries representing yet unknown fucosyltransferases. Putative fucosyltransferases provided by the hits that were retrieved from the database searches were analyzed with respect to fucosyltransferase activity of the corresponding polypeptides. Based on this approach yet unknown fucosyltransferases were identified which utilize a lactotetraose as acceptor molecule to be fucosylated.

SUMMARY

Provided are novel fructosyltransferases originating from bacterial cells. Said fucosyltransferases utilize a lactotetraose as acceptor molecule for their fucosyltransferase activity. Said novel fucosyltransferases can be used to synthesize fucosylated oligosaccharides based on LNT and/or LNnT.

According to a first aspect, provided is a method for producing fucosylated oligosaccharides, wherein a genetically engineered cell is used for producing said fucosylated oligosaccharide. Said genetically engineered cell has been genetically engineered to express a heterologous fucosyltransferase which is capable of transferring a fucose residue from a donor substrate to an acceptor molecule, wherein said acceptor molecule is a lactotetraose.

According to a second aspect, provided is a genetically engineered cell for use in a method for producing fucosylated oligosaccharides. Said genetically engineered cell has been genetically engineered to express a heterologous fucosyltransferase which is capable of transferring a fucose residue from a donor substrate to an acceptor molecule, wherein said acceptor molecule is a lactotetraose.

According to a third aspect, provided is a recombinant nucleic acid molecule for expressing a heterologous fucosyltransferase when propagated in a cell, wherein said fucosyltransferase is capable of transferring a fucose residue from a donor substrate to an acceptor molecule, wherein said acceptor molecule is a lactotetraose.

According to a fourth aspect, provided are fucosyltransferases being capable of transferring a fucose residue from a donor substrate to an acceptor molecule, wherein said acceptor molecule is a lactotetraose.

According to a fifth aspect, provided is the use of a fucosyltransferase being capable of transferring a fucose residue from a donor substrate to an acceptor molecule, wherein said acceptor molecule is a lactotetraose, for the production of fucosylated oligosaccharides.

According to a sixth aspect, provided is a method for producing fucosylated oligosaccharides by in vitro biocatalysis, wherein a fucosyltransferase is used, said fucosyltransferase being capable of transferring a fucose residue from a donor substrate to an acceptor molecule.

According to a seventh aspect, provided are fucosylated oligosaccharides being produced by a method according to the first aspect or by a method according to the sixth aspect.

According to an eight aspect, provided is the use of fucosylated oligosaccharides according to the seventh aspect for manufacturing a nutritional composition.

According to a ninth aspect, provided is a nutritional composition containing at least one fucosylated oligosaccharide according to the seventh aspect.

BRIEF DESCRIPTION OF THE DRAWINGS

FIG. 2a shows chromatograms of fucosylated derivatives of LNT and LNnT.

FIG. 2b shows chromatograms of a mixture of LNFP-III and LNnFP-V as synthesized in in-vitro reactions using cell extracts containing a heterologously expressed fucosyltransferase from *B. fragilis*, i.e. FucT109 (upper panel) compared to chromatograms of sugar standards.

DETAILED DESCRIPTION

Figure 1:
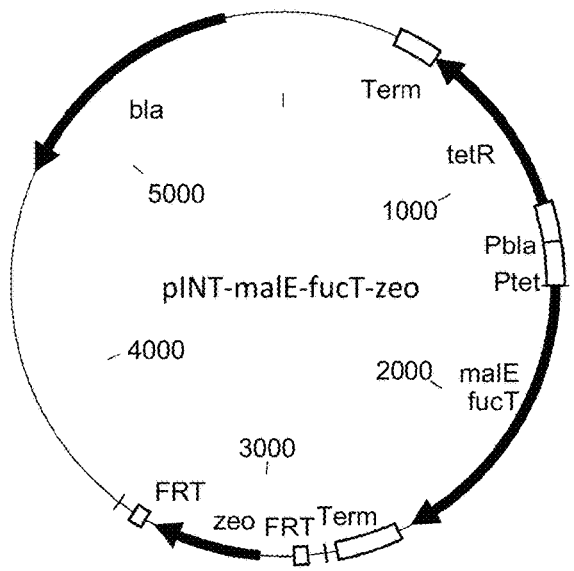
FIG. 1 is a schematic representation showing the plasmid map of expression vector pINT-malE-fucT-zeo which was used for heterologous expression of nucleotide sequences encoding putative fucosyltransferases in *E. coli*.
Figure 3:
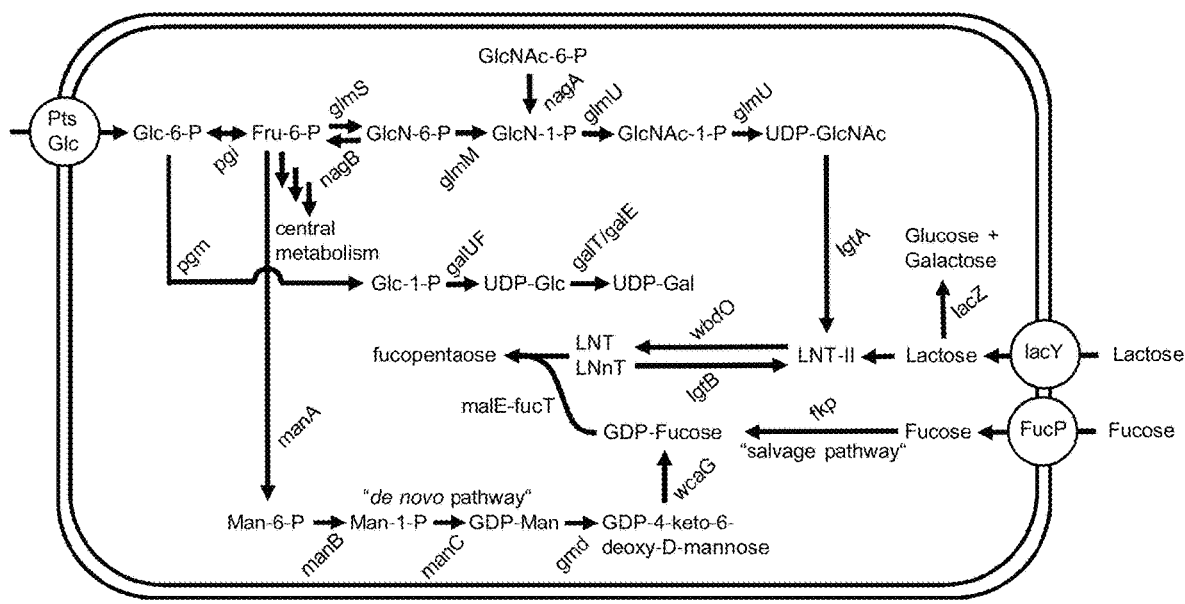
FIG. 3 is a schematic representation of metabolic pathways for the production of fucosylated oligosaccharides based on Lacto-N-tetraose and Lacto-N-neotetraose in *E. coli*.

According to the first aspect, provided is a method for producing fucosylated oligosaccharides, the method comprising the steps of:
a) providing at least one genetically engineered cell that has been genetically engineered to express a heterologous fucosyltransferase, wherein said heterologous fucosyltransferase is capable of transferring a fucose residue from a donor substrate to an acceptor molecule, said acceptor molecule being a lactotetraose;
b) cultivating the at least one genetically engineered cell in the presence of at least one carbon source and under conditions suitable for the at least one genetically engineered cell to transfer the fucose residue from the donor substrate to the acceptor molecule; and
c) optionally, recovering the fucosylated oligosaccharide.

In the method according to the first aspect, a genetically engineered cell is provided. The term "genetically engineered" as used herein refers to the modification of the cell's genetic make-up using molecular biological methods. The modification of the cell's genetic make-up may include the transfer of genes within and (or across species boundaries, inserting, deleting, replacing and/or modifying nucleotides, triplets, genes, open reading frames, promoters, enhancers, terminators and other nucleotide sequences mediating and/or controlling gene expression. The modification of the cell's genetic make-up aims to generate a genetically modified organism possessing particular, desired properties. Genetically engineered cells can contain one or more genes that are not present in the native (not genetically engineered) form of the cell. Techniques for introducing exogenous nucleic acid molecules and/or inserting exogenous nucleic acid molecules (recombinant, heterologous) into a cell's hereditary information for inserting, deleting or altering the nucleotide sequence of a cell's genetic information are known to the skilled artisan. Genetically engineered cells can contain one or more genes that are present in the native form of the cell, wherein said genes are modified and re-introduced into the cell by artificial means. The term "genetically engineered" also encompass cells that contain a nucleic acid molecule being endogenous to the cell, and that has been modified without removing the nucleic acid molecule from the cell. Such modifications include those obtained by gene replacement, site-specific mutations, and related techniques.

The genetically enginieered cell is a prokaryotic cell or a eukaryotic cell. Appropriate cells include yeast cells, bacteria, archaebacteria, fungal cells, insect cells, plant cells and animal cells, including mammalian cells (such as human cells and cell lines).

In an additional and/or alternative embodiment, the prokaryotic cell is a bacterial cell, preferably selected from the genus selected from the group consisting of *Bacillus, Lactobacillus, Lactococcus, Enterococcus, Bifidobacterium, Sporolactobacillus* spp., *Micromonospora* spp., *Micrococcus* spp., *Rhodococcus* spp., and *Pseudomonas*. Suitable bacterial species are *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus, Bacillus circulans, Bifidobacterium longum, Bifidobacterium infantis, Bifidobacterium bifidum, Citrobacter freundii, Clostridium cellulolyticum, Clostridium ljungdahlii, Clostridium autoethanogenum, Clostridium acetobutylicum, Corynebacterium glutamicum, Enterococcus faecium, Enterococcus thermophiles, Escherichia coli, Erwinia herbicola (Pantoea agglomerans), Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, Lactococcus lactis, Pantoea citrea, Pectobacterium carotovorum, Proprionibacterium freudenreichii, Pseudomonas fluorescens, Pseudomonas aeruginosa, Streptococcus thermophiles* and *Xanthomonas campestris*.

In an additional and/or alternative embodiment, the eukaryotic cell is a yeast cell, an insect cell, a plant cell or a mammalian cell. The yeast cell is preferably selected from the group consisting of *Saccharomyces* sp., in particular *Saccharomyces cerevisiae, Saccharomycopsis* sp., *Pichia* sp., in particular *Pichia pastoris, Hansenula* sp., *Kluyveromyces* sp., *Yarrowia* sp., *Rhodotorula* sp., and *Schizosaccharomyces* sp.

The genetically engineered cell has been genetically enginieered to express a heterologous fucosyltransferase. The term "heterologous" as used herein refers to a nucleotide sequence, nucleic acid molecule or polypeptide that is foreign to a cell or organism, i.e. to a nucleotide sequence, nucleic acid molecule or polypeptide that does not naturally occurs is said cell or organism. A "heterologous sequence" or a "heterologous nucleic acid" or "heterologous polypeptide", as used herein, is one that originates from a source foreign to the particular host cell (e.g. from a different species), or, if from the same source, is modified from its original form. Thus, a heterologous nucleic acid operably linked to a promoter is from a source different from that from which the promoter was derived, or, if from the same source, is modified from its original form. The heterologous sequence may be stably introduced, e.g. by transfection, transformation, conjugation or transduction, into the genome of the host microbial host cell, thus representing a genetically modified host cell. Techniques may be applied which will depend on the host cell the sequence is to be introduced. Various techniques are known to a person skilled in the art and are, e.g., disclosed in Sambrook et al., Molecular Cloning: A Laboratory Manual, 2nd Ed., Cold Spring Harbor Laboratory Press, Cold Spring Harbor, N.Y. (1989). Accordingly, a "heterologous polypeptide" is a polypeptide that does not naturally occur in the cell, and a "heterologous fucosyltransferase" is a fucosyltransferase that does not naturally occur in the cell.

The term "fucosyltransferase" as used herein, refers to polypeptides which are capable of catalyzing the transfer of a fucose residue from a donor substrate to an acceptor molecule. The donor substrate for the transfer of a fucose residue to an acceptor molecule is typically guanosinediphosphate L-fucose (GDP-L-fucose). Suitable acceptor molecule for fucose residues include oligosaccharides, glycopetides, glycoproteins, and glycolipids. Typically, the fucose residue is transferred to e.g. an N-acetylglucosamine residue, N-acetylgalactosamine residue, galactose residue, fucose residue, sialic acid residue, or glucose residue of the oligosaccharide or a saccharide moiety of the glycoprotein or glycolipid. The term "fucosyltransferase" as used herein is also understood to encompass functional variants of said novel fucosyltransferase, functional fragments of said fucosyltransferases and functional fragments of said functional variants. The term "functional" indicates that said variants and fragments are also capable of catalysing the transfer of a fucose residue from a donor substrate to an acceptor molecule, i.e. they can possess fucosyltransferase activity.

The term "functional fragment" as used herein refers to a truncated polypeptide as compared to the naturally occurring fucosyltransferase, and which fragment is capable of possessing the same fucosyltransferase activity as the naturally occurring polypeptide said fragment originates from.

The term "functional variant" as used herein refers to a polypeptide which is capable of possessing the same fucosyltransferase activity as the naturally occurring polypeptide said derivative originates from, but which has an altered amino acid sequence as compared to the naturally occurring polypeptide.

The heterologous fucosyltransferase is capable of transferring a fucose residue from a donor substrate to an acceptor molecule. The term "capable of" with respect to the heterologous fucosyltransferase refers to the fucosyltransferase activity of the heterologous fucosyltransferase and the provision that suitable reaction conditions are required for the heterologous fucosyltransferase to possess its enzymatic activity. In the absence of suitable reaction conditions, the heterologous fucosyltransferase does not possess its enzymatic activity, but retains its enzymatic activity and possesses its enzymatic activity when suitable reaction conditions are restored. Suitable reaction conditions include the presence of a suitable donor substrate, the presence of suitable acceptor molecules, the presence of essential cofactors such as—for example—monovalent or divalent ions, a pH value in an appropriate range, a suitable temperature and the like. It is not necessary that the optimum values for each and every factor effecting the enzymatic reaction of the heterologous fucosyltransferase is met, but the reaction conditions have to be such that the heterologous fucosyltransferase performs its enzymatic activity. Accordingly, the term "capable of" excludes any conditions upon which the enzymatic activity of the heterologous fucosyltransferase has been irreversibly impaired, and also excluded exposure of the heterologous fucosyltransferase to any such condition. Instead, "capable of" means that the fucosyltransferase is enzymatically active, i.e. possesses its fucosyltransferase activity, if suitable reactions conditions (where all requirements being necessary for the fucosyltransferase to perform its enzymatic activity) are provided.

Fucosyltransferases can form α-1,2-, α-1,3-, α-1,4-, or α-1,6-glycosidic linkages between fucose and the saccharide moiety of the acceptor molecule. Accordingly, the term "alpha-1,2-fucosyltransferase" refers to a glycosyltransferase that catalyzes the transfer of fucose from a donor substrate to an acceptor molecule forming an alpha-1,2-linkage of the fucose residue and a saccharide residue of the acceptor molecule. The term "alpha-1,3-fucosyltranferase" refers to a glycosyltransferase that catalyses the transfer of fucose from a donor substrate to an acceptor molecule in an alpha-1,3-linkage of the fucose residue and a saccharide residue of the acceptor molecule. The term "alpha-1,4-fucosyltranferase" refers to a glycosyltransferase that catalyses the transfer of fucose from a donor substrate to an acceptor molecule in an alpha-1,4-linkage of the fucose residue and a saccharide residue of the acceptor molecule; and the term "alpha-1,6-fucosyltranferase" refers to a glycosyltransferase that catalyses the transfer of fucose from a donor substrate to an acceptor molecule in an alpha-1,6-linkage of the fucose residue and a saccharide residue of the acceptor molecule.

The term "donor substrate" with respect to transferring a fucose residue from the donor substrate to an acceptor molecule refers to a molecule comprising a fucose residue, said molecule being utilized by the heterologous fucosyltransferase a source of fucose which is to be transferred to a specific acceptor molecule. Typically, the donor substrate is GDP-fucose.

The term "acceptor molecule" as used herein refers to a molecule which receives the fucose residue from the donor substrate by the enzymatic activity of the heterologous fucosyltransferase. As used herein, the term "acceptor molecule" more specifically refers to a molecule consisting of or comprising a saccharide moiety. Unless otherwise stated, the term "acceptor molecule" as used herein refers to a lactotetraose.

The heterologous fucosyltransferase is capable of transferring a fucose residue to a lactotetraose as an acceptor molecule. The term "lactotetraose" as used herein refers to a tetrasaccharide, i.e. an oligosaccharide consisting of 4 monosaccharide residues, wherein the tetrasaccharide comprises a lactose motif (Gal(β1,4)Glc) at its reducing end.

In an embodiment, the lactotetraose is selected from the group consisting of Lacto-N-tetraose (LNT; Gal(β1,3)GlcNAc(β1,3)Gal(β1,4)Glc) and Lacto-N-neotetraose (LNnT; Gal(β1,3)GlcNAc(β1,4)Gal(β1,4)Glc). The enzymatic activity of the heterologous fucosyltransferase leads to a fucosylated oligosaccharide, more specifically to a fucosylated lactotetraose, i.e. a lactofucopentaose. Said lactofucopentaose is a pentasaccharide preferably selected from the group consisting of lacto-N-fucopentaose I (LNFP-I), lacto-N-neofucopentaose I (LNnFP-I), lacto-N-fucopentaose II (LNFP II), lacto-N-neofucopentaose III (LNnFP-III), lacto-N-fucopentaose V (LNFP-V) and lacto-N-neofucopentaose V (LNnFP-V).

Polypeptides which were identified in the genome of various bacterial species and which are capable of possessing fucosyltransferase activity for transferring a fucose residue from a donor substrate to a lactotetraose are shown in Table 1.

TABLE 1

Fucosyltransferases being capable of transferring a fucose residue from a donor substrate to a lactotetraose. The amino acid sequences (aa) of the fucosyltransferases used in the examples and the nucleotide sequences (nt) encoding said amino acid sequences and being used for expressing the fucosyltransferases according to the examples are indicated in the last two columns of the table by identifying their SEQ ID NOs.

| Species/source | Genbank accession number | SEQ ID NOs: nucleic acid | SEQ ID NOs: amino acid |
|---|---|---|---|
| *Helicobacter hepaticus* ATCC 51449 (HH_0072) | AAP76669 | 1 | 16 |
| *Brachyspira pilosicoli* WesB (WESB_1374) | CCG56842 | 2 | 17 |
| *Yersinia* sp. A125 KOH2 (WbcH-like) | CAI39173 | 3 | 18 |
| *Gramella forsetii* KT0803 | WP_011708479 | 4 | 19 |
| *Francisella philomiragia* ssp. *philomiragia* ATCC 25015 (FTPG_00102) | EET21243 | 5 | 20 |
| *Pseudogulbenkiania ferrooxidans* 2002 (FuraDRAFT_0420) | EEG10438 | 6 | 21 |
| *Sideroxydans lithotrophicus* ES-11 (Slit_2889) | ADE13114 | 7 | 22 |
| *Providencia alcalifaciens* (WdcS) | AFH02807 | 8 | 23 |
| *Pseudoalteromonas haloplanktis* ANT/505 (PH505_ae00940) | EGI74693 | 9 | 24 |
| *Roseovarius nubinhibens* ISM (ISM_09170) | EAP78457 | 10 | 25 |
| *Thalassospira profundimaris* WP0211 (TH2_05058) | EKF09232.1 | 11 | 30 |
| *Desulfovibrio alaskensis* G20 (Dde_2877) | ABB39672 | 12 | 26 |
| *Thermosynechococcus elongates* BP-1 (tl10994) | BAC08546 | 13 | 27 |

TABLE 1-continued

Fucosyltransferases being capable of transferring a fucose residue from a donor substrate to a lactotetraose. The amino acid sequences (aa) of the fucosyltransferases used in the examples and the nucleotide sequences (nt) encoding said amino acid sequences and being used for expressing the fucosyltransferases according to the examples are indicated in the last two columns of the table by identifying their SEQ ID NOs.

| Species/source | Genbank accession number | SEQ ID NOs: nucleic acid | SEQ ID NOs: amino acid |
|---|---|---|---|
| *Bacteroides fragilis* strain ATCC 25285 (BF9343_3370) | CAH09151 | 14 | 28 |
| *Escherichia coli* O126 (WbgL) | ABE98421 | 15 | 29 |

Thus, in an additional and/or alternative embodiment, the heterologous fucosyltransferase is selected from the group consisting of polypeptides as represented by any one of SEQ ID NOs: 16 to 30, functional variants of the polypeptides as represented by any one of SEQ ID NOs: 16 to 30, functional fragments of the polypeptides as represented by any one of SEQ ID NOs: 16 to 30, and functional variants of the functional fragments of the polypeptides as represented by any one of SEQ ID NOs: 16 to 30. Thus, the heterologous fucosyltransferase is selected from the group of polypeptides as represented by any one of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 and SEQ ID NO: 30, functional fragments of the polypeptides as represented by any one of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 and SEQ ID NO: 30, functional variants of the polypeptides as represented by any one of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 and SEQ ID NO: 30, and functional variants of the functional fragments of the polypeptides as represented by any one of SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29 and SEQ ID NO: 30.

In an additional and/or alternative embodiment, the heterologous fucosyltransferase is encoded by a nucleic acid molecule comprising i) a nucleotide sequence as represented by any one of SEQ ID NOs: 1 to 15;

ii) a nucleotide sequence having a sequence identity of at least 80% to one of the nucleotides sequences as represented by any one of SEQ ID NOs: 1 to 15, preferably across the entire length of the sequence;

iii) a nucleotide sequence which encodes a polypeptide having an amino acid sequence as represented by any one of SEQ ID NOs: 16 to 30;

iv) a nucleotide sequence which encodes a polypeptide having an amino acid sequence which has at least 80% identity to any one of the amino acid sequences as represented by any one of SEQ ID NOs: 16 to 30;

v) a nucleotide sequence encoding a functional fragment of any one of the polypeptides according to iii) and iv); or vi) wherein the nucleic acid molecule hybridizes to a complementary strand of a nucleic acid molecule according to i), ii), iii), iv) or v) under stringent conditions.

The expression "SEQ ID NOs: 1 to 15" refers to the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15.

"Hybridizing under stringent conditions" refers—for example—to: hybridizing in 4×SSC at 65° C. and subsequent multiple washings in 0.1×SSC at 65° C. for—in total—about 1 hour. Less stringent hybridization conditions are for example: hybridizing in 4×SSC at 37° C. and subsequent multiple washing in 1×SSC at room temperature. "Stringent hybridization conditions" can also mean: hybridizing at 68° C. in 0.25 M sodium phosphate, pH 7.2, 7% (w/v) SDS, 1 mM EDTA and 1% (w/v) BSA for 16 hours and subsequent washing, two times with 2×SSC and 0.1% (w/v) SDS at 68° C.

The nucleotide sequence encoding the heterologous fucosyltransferase may be present on a linear nucleic acid molecule or on a circular nucleic acid molecule. Additionally and/or alternatively, the nucleotide sequence encoding the heterologous fucosyltransferase may be present on an extrachromosomal nucleic acid molecule or be integrated into the or at least one of the cell's chromosomal nucleic acid molecule(s), wherein said chromosomal nucleic acid molecule may be a linear or a circular (bacterial chromosome) nucleic acid molecule.

The at least one genetically engineered cell is cultivated in the presence of at least one carbon source.

As used herein, the term "cultivating" means growing a cell in a fermentation broth and under conditions permissive and suitable for the production of the desired fucosylated oligosaccharide(s). A couple of suitable fermentation broths and conditions for cell cultivation will be readily available for one skilled in the art upon reading the disclosure of this invention in connection with the skilled person's technical and expert background.

In an additional and/or alternative embodiment, the at least one carbon source is selected from the group consisting glycerol, sucrose, glucose, galactose, fructose, molasses, lactose, xylose, cellulose, pyruvate, succinate, syngas carbon monoxide and any other source of carbon and energy that can be metabolized be the genetically engineered cell to produce the desired fucosylated oligosaccharide. In this context, it is to be understood that any other—preferably low-cost—fermentation substrates can be employed as carbon source, and the person skilled in the art will readily able to employ a carbon source suitable within the present invention in order to grow the microorganism to produce the desired monosaccharide in a large scale. In a preferred embodiment of the production of fucosylated oligosaccharides, lactose is supplied to the fermentation broth, in particular if the genetically engineered cell is not capable of synthesizing lactose itself. In an additional and/or alternative embodiment of the production of fucosylated oligosaccharides, fucose is supplied to the fermentation broth, in particular if the genetically engineered cell is not capable of synthesizing fucose itself. Supplementing the fermentation broth with fucose may enhance intracellular synthesis of GDP-fucose using a fucose salvage pathway or fucose salvage system.

The at least one genetically engineered cell is cultivated under conditions that are suitable for the at least one genetically engineered cell to transfer the fucose residue from the donor substrate of the heterologous fucosyltransferase to the acceptor molecule. For producing the fucosylated oligosaccharide, the at least one genetically engineered cell is cultivated in a fermentation broth which provides sufficient amounts of nutrients for the at least one cell to be metabolically active such that the heterologous fucosyltransferase is expressed and such that the cell provides sufficient amounts of donor substrate and acceptor molecules for the heterologous fucosyltransferase to be enzymatically active. For the conditions to be suitable for the at least one genetically engineered cell to transfer the fucose residue from the donor substrate to the acceptor molecule by means of the activity of its heterologous fucosyltransferase, the fermentation broth has—among others—a suitable temperature, a suitable pH value, a suitable amount of oxygen dissolved in the fermentation broth, as well as a suitable osmolarity. The suitable values may vary and are depend on the type of cell that is cultivated. Suitable values can easily be determined by the skilled artisan.

In an additional and/or alternative embodiment, cultivating of the at least one genetically engineered cell under conditions suitable for the at least one genetically engineered cell to transfer the fucose residue from the donor substrate of the heterologous fucosyltransferase to the acceptor molecule comprises the step of supplying exogenous lactose to the fermentation broth while cultivating the at least one genetically engineered cell. This enables the at least one genetically engineered cell to take-up said exogenously supplied lactose for endogenous synthesis of a lactotetraose. Said endogenously synthesized lactotetraose can then serve as acceptor substrate for the heterologous fucosyltransferase.

In an additional and/or alternative embodiment, cultivating of the at least one genetically engineered cell under conditions suitable for the at least one genetically engineered cell to transfer the fucose residue from the donor substrate of the heterologous fucosyltransferase to the acceptor molecule comprises an endogenous synthesis of lactose by the at least one genetically engineered cell. In an embodiment, the endogenous synthesis of lactose may occur due to the natural competence of the genetically engineered cell to synthesize lactose. Additionally and/or alternatively, the endogenous synthesis of lactose occurs by overexpressing a heterologous β-1,4-galactosyltransferase in the genetically engineered cell. Thus, the genetically engineered cell has also been genetically engineered to overexpress, as compared to the genetically not engineered progenitor cell, said heterologous β-1,4-galactosylatransferase gene. Said heterologous β-1,4-galactosylatransferase gene encodes a β-1,4-galactosylatransferase which catalyses the formation of lactose from galactose and glucose. Examples of suitable β-1,4-galactosylatransferases are selected from the group consisting of Pm1141 from *Pasteurella multocida* (accession no. AEC04686) and Lex1 from *Aggregatibacter aphrophilus* NJ8700 (accession no. AK965832).

In an additional and/or alternative embodiment, cultivating of the at least one genetically engineered cell under conditions suitable for the at least one genetically engineered cell to transfer the fucose residue from the donor substrate of the heterologous fucosyltransferase to the acceptor molecule comprises the step of supplying lacto-N-triose-2 (LNT-2) to the fermentation broth while cultivating the at least one genetically engineered cell, wherein said at least one genetically engineered cell comprises (i) a β-1,3-galactosyltransferase or a β-1,4-galactosyltransferase, and (ii) an α-1,2- and/or α-1,3-fucosyltransferase as glycosyltransferase. LNT-2 is a trisaccharide which can be produced fairly efficient. Supplementing the fermentation broth with LNT-2 enables the at least one genetically engineered cell to take-up said exogenously supplied LNT-2 as precursor for endogenous synthesis of LNT or LNnT, which can in turn serve as acceptor molecules for the heterologous fucosyltransferase.

According to an additional and/or alternative embodiment of the method for producing a fucosylated oligosaccharide, the method comprising the step of cultivating at least one genetically engineered cell is a continuous fermentation process or a batch fermentation process, preferably a fed batch fermentation process.

Thus, according to the embodiment wherein the cultivation is a continuous fermentation process, i.e. a process wherein the at least one carbon source is constantly added to the fermentation broth during the cultivating step of the genetically engineered cell, and wherein fermentation broth is continuously recovered from the fermentation process. By constantly adding the carbon source during the cultivation step, a constant and effective production of the oligosaccharide is accomplished.

According to the embodiment wherein the cultivation is a batch fermentation process, a closed culture system is used with a specific nutrient composition at the beginning of the fermentation, and specific temperature, pressure, aeration and other environmental conditions to optimize growth. Neither nutrients are added to, nor waste products are removed from the fermentation process during cultivation of the cells.

Fed-batch fermentation is understood to be an operational technique where one or more nutrients (substrates) are fed (supplied) to the bioreactor during cultivation and in which the product(s) remain in the bioreactor until the end of the run or in which at least one portion of the fermentation broth including cells and product(s) is removed from the bioreactor during the fermentation process. Portions of the fermentation broth can be removed from the bioreactor multiple times and/or at different intervals during the fermentation process.

In an additional and/or alternative embodiment, the method for producing a fucosylated oligosaccharide comprises a recovery of the desired fucosylated oligosaccharide from the culture of the producing cell. As used herein, the term "recovering" means isolating, harvesting, purifying, collecting or otherwise separating from the host microorganism culture the oligosaccharide produced by the host microorganism according to the invention. The term "purifying" as used herein refers to the removal of at least a significant amount of impurities and undesired compound. Said impurities and undesired compounds (undesired side-products) comprise cells, ions and salts, other saccharides that the desired lactofucopentaose, for example monosaccharides, disaccharides, trisaccharides, tetrasaccharides, especially lactotetraoses, and other pentsaccharides than the desired lactofucopentaose.

In an additional and/or alternative embodiment, the recovering and/or purifying of the fucosylated oligosaccharide comprises a step selected from the group consisting of (i) crystallizing the fucosylated oligosaccharide from a solution of said fucosylated oligosaccharide, and (ii) spray-drying the fucosylated oligosaccharide. These steps provide a fucosylated oligosaccharide in crystallized of amorphous form.

In an additional and/or alternative embodiment of the recovery or purification of the desired fucosylated oligosaccharides, at least one glycosidase is applied, wherein the at least one glycosidase is used for degrading hindering and/or undesired impurities or side-products, unused starting substrates and intermediate products generated during the production of the desired oligosaccharide. By means of using the at least one glycosidase it is achieved that, e.g. other (oligo-)saccharides than the desired fucosylated oligosaccharide—which other (oligo-)saccharides are produced in or by the at least one genetically engineered cell during the synthesis of the desired fucosylated oligosaccharide, and which other oligosaccharides interfere with the purification step of the desired oligosaccharide, can be metabolised.

The at least one glycosidase can be either be externally added to the fermentation broth at the end of the fermentation process or endogenously synthesized by the at least one genetically engineered cell.

Adding the at least one glycosidase to the fermentation broth is advantageous, if the genetically engineered cell does not synthesize one or more glycosidases, for example because endogenous genes of the genetically engineered cell encoding said one or more glycosidases have been deleted or expression of endogenous genes encoding said one or more glycosidases has been impaired.

In an embodiment, wherein the at least one glycosidase is added to the fermentation broth, the at least one glycosidase is produced by at least one other cell than the genetically engineered cell for producing the fucosylated oligosaccharide, and said at least one other cell is additionally added to the fermentation broth for expressing the gene(s) encoding the at least one glycosidase.

In this embodiment, the at least one glycosidase being expressed by the at least one other cell is either a naturally occurring glycosidase of said one other cell or a heterologous glycosidase, wherein said other cell has been stably transformed to express the heterologous glycosidase, and wherein the expression of the heterologous glycosidase in the other cell is inducible. Preferably the heterologous glycosidase is encoded by a nucleotide sequence that has been stably integrated into the genome of the at least one other cell.

This embodiment is particularly suitable in a continuous fermentation process for the production of the fucosylated oligosaccharide, where, e.g., two separate fermentation vessels or containers are provided, whereas one vessel/container is used for the oligosaccharide synthesis reaction and the second vessel/container is essentially employed for cultivating the cells which express the heterologous glycosidase.

In an additional and/or alternative embodiment, the at least one glycosidase being expressed by the at least one other cell is an intracellular glycosidase. Thus, the at least one glycosidase being expressed be the at least one cell resides within said at least one cell. Said at least one other cell therefore ingests the undesired impurities, side-products, the unused starting substrates and/or intermediate products generated during the production of the desired oligosaccharide such that the internalized compounds are degraded by the at least one intracellular glycosidase.

In an alternative embodiment, the at least one glycosidase being expressed by the at least one other cell is secreted from the at least one other cell into the fermentation broth. Then, the undesired impurities, side-products, the unused starting substrates and/or intermediate products generated during the production of the desired oligosaccharide is degraded in the fermentation broth. This embodiment is advantageous in that the at least one other cell does not have to be capable of internalizing the undesired impurities, side-products, the unused starting substrates and/or intermediate products generated during the production of the desired oligosaccharide.

In a preferred embodiment, the glycosidase degrades lactose. A suitable glycosidase for degrading lactose is the β1,4-galactosidase LacZ of *E. coli*. A suitable glycosidase for hydrolyzing LNT-2, an intermediate product, is the β-N-acetylhexosaminidase Bbhl from *Bifidobacterium bifidum* JCM1254. A suitable glycosidase for hydrolysing the intermediate product LNT, is the β-1,3-galactosidases Bga42A from *Bifidobacterium longum* subsp. *infantis*.

In an additional and/or alternative embodiment, the genetically engineered cell, which also produces the at least one glycosidase or the at least one other cell producing the at least one glycosidase expresses the at least one glycosidase upon external induc-tion, e.g. via temperature-induced expression or via substrate-induced expression. This means that expression of the at least one glycosidase is downregulated during synthesis of the desired fucosylated oligosaccharide, and may be induced, e.g. by temperature or addition of an inductor such as IPTG, at the end of the fermentation process. The expression of the glycosidase will be induced after sufficient and/or essentially maximum amount of oligosaccharide has been produced during cultivation of the genetically engineered cell. Subsequently, the glycosidases being expressed will degrade undesired saccharide intermediates, substrates, etc., rendering the medium essentially free of the saccharide intermediates or substrates that would otherwise hinder or complicate the purification of the desired oligosaccharide. A couple of suitable inducible expression tools are known in the prior art (see, e.g. Sambrook et. al, 1989, supra), and one skilled will be able to apply a respectively suitable one for the desired oligosaccharide.

"Regulated" within the present context with reference to a gene is generally understood as a gene, whose transcription can be regulated in a controlled fashion, e.g. down- or up-regulated, i.e. the quantity of the synthesised protein encoded by the regulated gene is different, e.g. de-/down-regulated or upregulated, from the otherwise unregulated gene.

In an additional embodiment, monosaccharides resulting from the degradation of the undesired saccharide intermediates, substrates, etc. can be metabolized by the genetically engineered cell.

According to the second aspect, provided is a genetically engineered cell for producing or for use in a method for producing a fucosylated oligosaccharide. Said genetically engineered cell has been genetically engineered to express a heterologous fucosyltransferase which is capable of transferring a fucose residue from a donor substrate to an acceptor molecule, wherein said acceptor molecule is a lactotetraose.

The term "genetically engineered" as used herein with reference to a host cell indicates that the host cell replicates a heterologous or recombinant nucleic acid molecule, and/or expresses a peptide or protein encoded by a heterologous nucleotide sequence (i.e., a nucleotide sequence "foreign to said cell"). Genetically engineered cells can contain genes that are not found within the native (non-recombinant) form of the cell. Genetically engineered cells can also contain genes found in the native form of the cell wherein the genes are modified and re-introduced into the cell by artificial means. The term also encompasses cells that contain a nucleic acid molecule endogenous to the cell that has been modified without removing the nucleic acid from the cell; such modifications include those obtained by gene replacement, site-specific mutation, and related techniques. Accordingly, a "recombinant polypeptide" is one which has been produced by a genetically engineered cell.

Accordingly, a "genetically engineered cell" is understood as a cell which has been transformed or transfected.

Thus, the nucleotide sequences as used in the present invention, may, e.g., be comprised in a vector which is to be stably transformed/transfected or otherwise introduced into host microorganism cells.

Methods for generating "recombinant DNA", including isolation, synthesis, purification and amplification of genetic material, for use in transforming or transfecting selected host cells are known to the skilled artisan. Thus, it is common knowledge to transform cells with "hybrid" viral or circular plasmid DNA which includes selected exogenous (i.e. foreign or "heterologous") nucleotide sequences. These procedures known in the art involve generating a transformation vector by enzymatically cleaving circular viral or plasmid DNA to form linear DNA strands. Selected foreign DNA strands usually including sequences coding for desired protein product are prepared in linear form through use of the same/similar enzymes. The linear viral or plasmid DNA is incubated with the foreign DNA in the presence of ligating enzymes capable of effecting a restoration process and forming "hybrid" vectors which include the selected exogenous DNA segment "spliced" into the viral or circular DNA plasmid.

The genetically enginieered cell is a prokaryotic cell or a eukaryotic dell. Appropriate cells include yeast, bacteria, archaebacteria, fungi, insect cells, plant cells and animal cells, including mammalian cells (such as human cells and cell lines).

In an additional and/or alternative embodiment, the prokaryotic cell is a bacterial cell, preferably selected from the genus selected from the group consisting of *Bacillus, Lactobacillus, Lactococcus, Enterococcus, Bifidobacterium,* Sporolactobacillus spp., *Micromonospora* spp., *Micrococcus* spp., *Rhodococcus* spp., and *Pseudomonas*. Suitable bacterial species are *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus, Bacillus circulans, Bifidobacterium longum, Bifidobacterium infantis, Bifidobacterium bifidum, Citrobacter freundii, Clostridium cellulolyticum, Clostridium ljungdahlii, Clostridium autoethanogenum, Clostridium acetobutylicum, Corynebacterium glutamicum, Enterococcus faecium, Enterococcus thermophiles, Escherichia coli, Erwinia herbicola (Pantoea agglomerans), Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii, Lactococcus lactis, Pantoea citrea, Pectobacterium carotovorum, Proprionibacterium freudenreichii, Pseudomonas fluorescens, Pseudomonas aeruginosa, Streptococcus thermophiles* and *Xanthomonas campestris*.

In an additional and/or alternative embodiment, the eukaryotic cell is a yeast cell, an insect cell, a plant cell or a mammalian cell. The yeast cell is preferably selected from the group consisting of *Saccharomyces* sp., in particular *Saccharomyces cerevisiae, Saccharomycopsis* sp., *Pichia* sp., in particular *Pichia pastoris, Hansenula* sp., *Kluyveromyces* sp., *Yarrowia* sp., *Rhodotorula* sp., and *Schizosaccharomyces* sp.

The genetically engineered cell has been genetically engineered to express a heterologous fucosyltransferase being capable of transferring a fucose residue from a donor substrate to an acceptor molecule being a lactotetraose. In an additional and/or alternative embodiment, the heterologous fucosyltransferase is selected from the group consisting of polypeptides as represented by any one of SEQ ID NOs: 16 to 30, functional variants of the polypeptides as represented by any one of SEQ ID NOs: 16 to 30, functional fragments of the polypeptides as represented by any one of SEQ ID NOs: 16 to 30, and functional variants of the functional fragments of the polypeptides as represented by any one of SEQ ID NOs: 16 to 30.

In an additional and/or alternative embodiment, the heterologous fucosyltransferase is encoded by a nucleic acid molecule comprising
i) a nucleotide sequence as represented by any one of SEQ ID NOs: 1 to 15;
ii) a nucleotide sequence having a sequence identity of at least 80% to one of the nucleotides sequences as represented by any one of SEQ ID NOs: 1 to 15, preferably across the entire length of the sequence;
iii) a nucleotide sequence which encodes a polypeptide having an amino acid sequence as represented by any one of SEQ ID NOs: 16 to 30;
iv) a nucleotide sequence which encodes a polypeptide having an amino acid sequence which has at least 80% identity to any one of the amino acid sequences as represented by any one of SEQ ID NOs: 16 to 30;
v) a nucleotide sequence encoding a functional fragment of any one of the polypeptides according to iii) and iv); or
vi) wherein the nucleic acid molecule hybridizes to a complementary strand of a nucleic acid molecule according to i), ii), iii), iv) or v) under stringent conditions.

The nucleotide sequence encoding the heterologous fucosyltransferase may be present on a linear or circular extra-chromosomal nucleic acid molecule within the genetically engineered cell or be integrated into the cell's chromosomal nucleic acid molecule, wherein said chromosomal nucleic acid molecule may be a linear or circular (bacterial chromosome) nucleic acid molecule.

The genetically engineered cell is capable of synthesizing GDP-fucose which is necessary for the reaction to be catalyzed by the heterologous polypeptide capable of possessing fucosyltransferase activity for transferring a fucose residue from a donor substrate to a lactotetraose to produce the desired fucosylated oligosaccharide, because GDP-fucose serves as donor substrate for the fucose residue to be transferred to a lactotetraose by the heterologous fucosyltransferase. Thus, in an embodiment, the genetically engineered cell has also been genetically engineered to comprise an increased intracellular GDP-fucose production capability as compared to the cell prior to being genetically engineered.

In an additional and/or alternative embodiment, providing an intracellular pool of GDP-fucose for producing fucosylated oligosaccharides is achieved that the genetically engineered cell has also been genetically engineered such that a gene encoding a bifunctional fucosekinase/L-fucose-1-phosphate-guanyltransferase (Fkp), preferably a gene encoding the bifunctional fucosekinase/L-fucose-1-phosphate-guanyltransferase (Fkp) from *Bacteroides fragilis* (acc. no. AY849806), which is capable of converting L-fucose into GDP-fucose, is expressed or overexpressed by said cell. Preferably, L-fucose is fed to the genetically engineered cell during fermentation of the cells for producing the desired fucosylated oligosaccharide.

In an additional and/or alternative embodiment, GDP-fucose for synthesis of the desired fucosylated oligosaccharide can be taken from the cell's own GDP-fucose metabolism using the "de novo pathway". To increase the intracellular GDP-fucose pool via the "de novo pathway", the genetically engineered cell has also been genetically engineered to express or overexpress—as compared to the cell prior to being genetically engineered—at least one of the genes encoding phosphomannomutase, mannose-1-phosphate guanosyltransferase, GDP-mannose-4,6-dehydratase, and GDP-L-fucose synthase. In a preferred embodiment, the cell is genetically modified to overexpress all four of said genes.

In an additional and/or alternative embodiment, the genetically engineered cell has also been genetically engineered to possess an increased import of exogenous L-fucose across its cell membrane. Preferably, the genetically engineered cell has also been genetically engineered to express or overexpress—as compared to the progenitor cell before being genetically engineered—one nucleotide sequence selected from the group consisting of nucleotide sequences encoding the major facilitator transporter FucP from *E. coli.* MG1655 (acc. no. AIZ90162), nucleotide sequences encoding functional variants of the major facilitator transporter FucP from *E. coli*, nucleotide sequences encoding functional fragments of the major facilitator transporter FucP from *E. coli*, and nucleotide sequences encoding functional variants of the functional fragments of the major facilitator transporter FucP from *E. coli*. Expression or overexpression of the major facilitator transporter FucP, is functional variants and/or the functional fragments thereof in the genetically engineered cell increases the cell's uptake of exogenous L-fucose across its cell membrane.

In an additional and/or alternative embodiment, the genetically engineered cell has also been genetically engineered to prevent depletion of the cell's intracellular GDP-fucose pool. In an embodiment, the cell is genetically engineered in that expression of the gene encoding WcaJ, which catalyses the first step in colonic acid synthesis, is impaired or inactivated, preferably in that the WcaJ gene has been at least partially deleted from the cell's genetic information, or in that the nucleotide sequence of the WcaJ gene has been altered such that transcription of the gene encoding WcaJ is impossible. In an additional and/or alternative approach, the nucleotide sequence of the gene encoding WcaJ has been altered such that an enzymatically inactive polypeptide is encoded by the altered WcaJ gene, for example in that a stop codon is introduced into the open reading frame leading to a truncated variant of WcaJ, which represents an non-functional fragment, is expressed, or in that the nucleotides sequence of the WcaJ gene is altered such that the polypeptide encoded by said altered WcaJ gene differs from the wild type WcaJ in one or more amino acid residues rendering the resulting polypeptide enzymatically inactive.

In an additional and/or alternative embodiment, the genetically engineered cell has also been genetically engineered in that the genes fucI and/or fucK, encoding the L-fucose isomerase and the L-fuculose kinase respectively, are deleted, the nucleotide sequence of fucI and/or fucK is altered to irreversibly inactivate the enzymatic activity of the corresponding polypeptide(s), or in that the expression of fucI and/or fucK is impaired. Abolishing intracellular synthesis of FucI and/or fucK abolishes fucose catabolism in the corresponding cell, thereby increasing the amount of fucose that is available for generating GDP-fucose.

In an additional embodiment, the genetically engineered cell has also been genetically engineered such that the cell (i) does not to express one or more polypeptides which intracellularly degrade one or more precursors of the desired fucosylated oligosaccharide to be produced, or (ii) expresses one or more polypeptides having an altered amino acid sequence and/or length—as compared to its naturally occurring homolog—to impair the activity of such an enzyme intracellularly degrading one or more precursors of the desired fucosylated oligosaccharide to be produced.

The term "precursor" as used herein with respect to the desired fucosylated oligosaccharides refers to compounds which are intermediates in the biosynthetic pathway of the desired fucosylated oligosaccharide to be produced. These intermediates include endogenous compounds, i.e. compounds which are produced and may be naturally present in the host cell, even when their synthesis in the bacterial host cell is enhanced by genetic modification of the host.

In an additional and/or alternative embodiment, the genetically engineered cell has also been genetically engineered to not comprise an enzymatically active β-galactosidase.

In an additional and/or alternative embodiment, the genetically engineered cell has also been genetically modified to lack a functional LacZ or to comprise a functional LacZ gene whose expression is tightly regulated and which is not expressed during the fermentation process for producing the fucosylated oligosaccharide.

Additionally and/or alternatively, the genetically engineered cell has also been genetically engineered such that the cell does not comprise or express polypeptides possessing an enzymatic activity which hydrolyzes another precursor of the desired fucosylated oligosaccharide than lactose, e.g. LNT-2, LNT or LNnT, or larger derivatives of LNT and LNnT. To this end, the genetically engineered cell has also been genetically engineered such that the genome of the cell does not contain a nucleotide sequence encoding a polypeptide being capable of hydrolyzing said another precursor of the desired fucosylated oligosaccharide, or such that expression of the genes encoding such proteins are regulated in that way that they are not expressed during the fermentation process for producing the fucosylated oligosaccharide.

In an additional and/or alternative embodiment, the genetically engineered cell comprises at least one nucleotide sequence encoding a polypeptide being capable of exhibiting β-1,3-N-acetylglucosaminyltransferase activity. The genetically engineered cell of this embodiment is capable of expressing the polypeptide being capable of exhibiting β-1,3-N-acetylglucosaminyltransferase activity. Preferably, the genetically engineered cell expresses said polypeptide being capable of exhibiting β-1,3-N-acetylglucosaminyltransferase activity. More preferably, said genetically engineered cell comprises the polypeptide being capable of exhibiting β-1,3-N-acetylglucosaminyltransferase activity. Preferably, said at least one nucleotide sequence encoding a polypeptide being capable of exhibiting β-1,3-N-acetylglucosaminyltransferase activity is a heterologous nucleic acid sequence, i.e. is a nucleotide sequence not naturally occurring in a non-genetically engineered ancestor of the genetically engineered cell.

By expressing a polypeptide being capable of exhibiting β-1,3-N-acetylglucosaminyltransferase activity, the host cell is able to ligate N-acetylglucosamine to the acceptor substrate lactose when said polypeptide possesses its β-1,3-N-acetylglucosaminyltransferase activity, thereby generating LNT-2 intracellularly.

In an additional and/or alternative embodiment, the polypeptide being capable of exhibiting β-1,3-N-acetylglucosaminyltransferase activity for a transfer of N-acetylglucosamine to lactose is a β-1,3-N-acetylglucosaminyltransferase that can be selected from the group consisting of LgtA from *Neisseria meningitidis* MC58 (acc. no. NP_274923) and the β-1,3-N-acetylglucosaminyltransferase from *Pasteurella multocida* subsp. *multocida* str. HN06 (acc. no. PMCN06_0022).

In an additional and/or alternative embodiment, the genetically engineered cell comprises at least one nucleotide sequence encoding a polypeptide being capable of exhibiting β-1,3-galactosyltransferase activity or β-1,4-galactosyltransferase activity. The genetically engineered cell of this embodiment is capable of expressing the polypeptide being capable of exhibiting β-1,3-galactosyltransferase activity or β-1,4-galactosyltransferase activity. Preferably, the genetically engineered cell expresses said polypeptide being capable of exhibiting β-1,3-galactosyltransferase activity or β-1,4-galactosyltransferase activity. More preferably, said genetically engineered cell comprises the polypeptide being capable of exhibiting β-1,3-galactosyltransferase activity or β-1,4-galactosyltransferase activity. Preferably, said at least one nucleotide sequence encoding a polypeptide being capable of exhibiting β-1,3-galactosyltransferase activity or β-1,4-galactosyltransferase activity. is a heterologous nucleic acid sequence, i.e. is a nucleotide sequence not naturally occurring in a non-genetically engineered ancestor of the genetically engineered cell. By expressing a polypeptide being capable of exhibiting β-1,3-galactosyltransferase activity or β-1,4-galactosyltransferase activity, the genetically engineered cell is capable of galactosylating LNT-2 to intracellularly generate LNT or LNnT, respectively.

In an additional and/or alternative embodiment, the polypeptide being capable of exhibiting β-1,3-galactosyltransferase activity for the galactosylation of LNT-2 to produce LNT is a β-1,3-galactosyltransferase selected from the group consisting of the β-1,3-galactosyltransferase WbdO derived from *Salmonella enterica* (acc. no. AY730594) and the β-1,3-galactosyltransferase being encoded by a gene selected from the group consisting of wbgO from *E. coli* O55:H7 (acc. No. BAG11838), furA from *Lutiella nitroferrum* (FuraDRAFT_0419), and functional fragments of said β-1,3-galactosyltransferases.

In an additional and/or alternative embodiment, the polypeptide being capable of exhibiting β-1,4-galactosyltransferase activity for the galactosylation of LNT-2 to produce LNnT is a β-1,4-galactosyltransferase selected from the group consisting of LgtB from *Neisseria meningitides* (acc. no. AAF42257), Lex1 from *Aggregatibacter aphrophilus* NJ8700 (acc. no. YP_003008647), GalT from *Kingella denitrificans* ATCC 33394 (acc. no. HMPREF9098_2407), GatD from *Pasteurella multocida* M1404 (acc. no. GQ444331), GalT from *Bacterioidis fragilis* NCTC9343 (acc. no. BF9343_0585), IsgD from *Haemophilus influenza* (acc. no. AAA24981), GalT from *Helicobacter pylori* (acc. no. AB035971), and functional fragments of said β-1,4-galactosyltransferases.

UDP-galactose and UDP-N-acetylglucosamine are required for intracellular synthesis of LNT or LNnT, or larger derivatives thereof, in the genetically engineered cell.

Intracellular UDP-galactose in the genetically engineered cell can be provided by feeding galactose to the genetically engineered cell in that the cells are cultivated in a fermentation broth that contains galactose. The galactose is taken up by the cell, phosphorylated to galactose-1-phosphate and then converted to UDP-galactose. Genes encoding polypeptides bearing the enzymatic activities that are required for these reactions are well known.

In an additional and/or alternative embodiment, the intracellular supply of UDP-galactose can also be obtained from the cell's own metabolism, and the cell's own metabolism can be improved by genetic modification of the cell such that, for example, the cell overexpresses UDP-galactose-4'-epimerase, or overexpresses the UDP-galactose-4'-epimerase in combination with the glucose-1-phosphate-1-uridinyl-transferase.

Intracellular UDP-N-acetylglucosamine in the genetically engineered cell can be also obtained from the cell's own UDP-N-acetylglucosamine metabolism. To increase the intracellular UDP-N-acetylglucosamine pool in the genetically engineered cell, the cell can be genetically modified such that one or more of the genes encoding L-glutamine:D-fuctose-6-phosphate aminotransferase, phosphoglucosamine mutase, phosphoglucomutase, and N-acetylglucosamine-1-phosphate uridyltransferase/glucosamine-1-phosphate acetyltransferase are overexpressed.

In an additional and/or alternative embodiment, the cell is genetically modified such that the N-acetylglucosamine catabolism within the genetically engineered has been inactivated. Inactivation of the cell's N-acetylglucosamine catabolism improves the intracellular level of UDP-N-acetylglucosamine being available for the intracellular synthesis of N-acetylglucosamine.

In an additional and/or alternative embodiment, the genetically modified cell for use in the synthesis of complex fucosylated HMOs is capable of incorporating lactose across its cell membrane to accumulate lactose as starting material for the production of the desired fucosylated oligosaccharide. Therefore, the cell can express its endogenous gene encoding a lactose permease. In an additional and/or alternative embodiment, the cell is genetically modified to contain and express a heterologous lactose permease gene, in particular if the cell does not naturally comprise and expresses a gene encoding a lactose permease.

In an additional and/or alternative embodiment, the lactose for producing the desired fucosylated oligosaccharide is provided by means of intracellular synthesis of lactose by the cell. Preferably, this is achieved in that the cell expresses an endogenous or recombinant gene encoding a β1-4-galactosyltransefrase, said β1-4-galactosyltransferase being capable of transferring the galactose moiety of UDP-galactose to a glucose molecule. This β1-4-galactosyltransefrase can be selected from Pm1141 from *Pasteurella multocida* (acc. no.: AEC04686) or Lex1 from *Aggregatibacter aphrophilus* NJ8700 (acc. no. YP_003008647).

Thus, in an additional and/or alternative embodiment, the genetically engineered cell comprises
(i) a β-1,3-N-acetylglucosaminyltransferase,
(ii) a β-1,3-galactosyltransferase or a β-1,4-galactosyltransferase; and
(iii) an α-1,2- and/or α-1,3-fucosyltransferase.

In another embodiment, wherein the genetically engineered cell is cultivated for producing a fucosylated oligosaccharide in that LNT-2 is added to the fermentation broth as a precursor of the acceptor molecule, the genetically engineered cell comprises
(i) a β-1,3-galactosyltransferase or a β-1,4-galactosyltransferase; and
(ii) an α-1,2- and/or α-1,3-fucosyltransferase as glycosyltransferase.

According to the third aspect, provided are recombinant nucleic acid molecules for expressing a heterologous fucosyltransferase in a genetically engineered cell. The term "nucleic acid molecule" refers to a single- or double-stranded deoxyribonucleotide macromolecule or ribonucleotide macromolecule and comprises stranded deoxyribonucleotide macromolecule or ribonucleotide macromolecule comprising one or more known analogues or naturally or synthetically produced nucleotides.

The recombinant nucleic acid molecule comprises a nucleotide sequence encoding for a fucosyltransferase that is selected from the group consisting of polypeptides as represented by any one of SEQ ID NOs: 16 to 30, functional variants of the polypeptides as represented by any one of SEQ ID NOs: 16 to 30, functional fragments of the polypeptides as represented by any one of SEQ ID NOs: 16 to 30, and functional variants of the functional fragments of the polypeptides as represented by any one of SEQ ID NOs: 16 to 30.

In an additional and/or alternative embodiment, the nucleotide sequence encoding the fucosyltransferase is selected from the group consisting of:
i) a nucleotide sequence as represented by any one of SEQ ID NOs: 1 to 15;
ii) a nucleotide sequence having a sequence identity of at least 80% to one of the nucleotides sequences as represented by any one of SEQ ID Nos: 1 to 15, preferably across the entire length of the sequence;
iii) a nucleotide sequence which encodes a polypeptide having an amino acid sequence as represented by any one of SEQ ID NOs: 16 to 30;
iv) a nucleotide sequence which encodes a polypeptide having an amino acid sequence which has at least 80% identity to any one of the amino acid sequences as represented by any one of SEQ ID NOs: 16 to 30;
v) a nucleotide sequence encoding a functional fragment of any one of the polypeptides according to iii) and iv); and
vi) a nucleic acid molecule that hybridizes to a complementary strand of a nucleic acid molecule according to i), ii), iii), iv) or v) under stringent conditions.

Within the scope of the present invention, also nucleic acid/polynucleotide and polypeptide polymorphic variants, alleles, mutants, and interspecies homologs are comprised by those terms, that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, or more amino acids, to a polypeptide resembling one of the amino acid sequences from SEQ ID NOs. 16 to 30.

"Variant(s)" as the term is used herein, is a polynucleotide or polypeptide that differs from a reference polynucleotide or polypeptide respectively, but retains the essential (enzymatic) properties of the reference polynucleotide or polypeptide. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to the persons skilled in the art.

In the recombinant nucleic acid molecule, the nucleotide sequence encoding the fucosyltransferase, the functional variant thereof, the functional fragment of the fucosyltransferase or the functional variant of the functional fragment is operably linked to at least one nucleotide sequence which mediates and/or controls expression of the fucosyltransferase, variant or fragment thereof, provided that the recombinant nucleic acid molecule is present in the cell.

The term "operably linked" as used herein, refers to a functional linkage between a nucleic acid expression control sequence (such as promoter, operator, enhancer, regulator, array of transcription factor binding sites, transcriptional terminator, ribosome binding site) and a second nucleotide sequence, wherein the expression control sequence affects transcription and/or translation of the nucleic acid corresponding to the second nucleotide sequence. Accordingly, the term "promoter" designates DNA sequences which usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcriptional initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene in a DNA polymer and provide a signal for termination of the transcription into mRNA are referred to as transcription "terminator" sequences.

A great variety of expression systems can be used to produce the polypeptides of the invention. Such systems include, among others, chromosomal, episomal and virus-derived vectors, e.g., vectors derived from bacterial plasmids, from bacteriophage, from transposons, from yeast episomes, from insertion elements, from yeast chromosomal elements, from viruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and to synthesize a polypeptide in a host may be used for expression in this regard. The appropriate DNA sequence may be inserted into the expression system by any of a variety of well-known and routine techniques, such as, for example, those set forth in Sambrook et al., supra. Accordingly, the nucleic acid molecule for expressing a heterologous fucosyltransferase in a genetically engineered cell is selected from the group consisting of plasmids, phagemids, cosmids, bacterial artificial chromosomes (BACs) and yeast artificial chromosomes (YACs).

According to the fourth aspect, provided are fucosyltransferases being capable of transferring a fucose residue from a donor substrate to an acceptor molecule, wherein said acceptor molecule is a lactotetraose.

The fucosyltransferases are of bacterial origin. The fucosyltransferases can be used to synthesize fucosylated oligosaccharides, preferably complex fucosylated HMOs based on lactose, LNT and/or LNnT or other oligosaccharides. The fucosylated oligosaccharide is a lactofucopentaose.

The fucosyltransferases are capable of transferring a fucose residue from a donor substrate, preferably GDP-fucose, to an acceptor molecule. In a preferred embodiment, the acceptor molecule is a lactotetraose, preferably LNT and/or LNnT.

In an additional and/or alternative embodiment, the fucosyltransferase is selected from the group consisting of polypeptides as represented by any one of SEQ ID NOs: 16 to 30, functional variants of the polypeptides as represented by any one of SEQ ID NOs: 16 to 30, functional fragments of the polypeptides as represented by any one of SEQ ID NOs: 16 to 30, and functional variants of the functional fragments of the polypeptides as represented by any one of SEQ ID NOs: 16 to 30.

The fucosyltransferases as represented by any one of SEQ ID NOs: 16 to 30 were not described to be fucosyltransferases which are capable of transferring a fucose residue from a donor substrate to a lactotetraose as acceptor substrate. The novel fucosyltransferases as represented by any one of SEQ ID NOs: 16 to 27 have previously not even been described as fucosyltransferases as such, i.e. regardless of their acceptor molecule.

The fucosyltransferases described herein before can be used for producing complex fucosylated oligosaccharides, either by a whole cell fermentation process, for example as described herein before, or by means of in-vitro biocatalysis. Hence, according to the fifth aspect, the use of at least one of the fucosyltransferases being capable of transferring a fucose residue from a donor substrate to an acceptor molecule, wherein said acceptor molecule is a lactotetraose for producing a fucosylated oligosaccharide is provided.

In an additional and/or alternative embodiment, the fucosyltransferases described herein before are used to synthesize complex fucosylated HMOs by in-vitro biocatalysis.

Using at least one of the novel fucosyltransferases in an in-vitro biocatalysis process comprises adding a suitable donor substrate containing a fucose residue, preferably GDP-fucose, and a suitable acceptor molecule to at least one of the novel fucosyltransferases in a solvent and under conditions appropriate for the fucosyltransferase to transfer the fucose residue from the donor substrate to the acceptor molecule, thereby synthesizing a fucosylated oligosaccharide. Preferably, the suitable acceptor molecule is a lactotetraose, more preferably LNT or LNnT. Using a lactotetraose as acceptor molecule, the reaction product of the fucosyltransferase in the in-vitro biocatalytic reaction is a lactofucopentaose. Said lactofucopentaose is preferably one pentasaccharide selected from the group consisting of lacto-N-fucopentaose I, lacto-N-neofucopentaose I, lacto-N-neofucopentaose III, lacto-N-fucopentaose V and lacto-N-neofucopentaose V.

According to the sixth aspect, provided is a method for producing fucosylated oligosaccharides, preferably fucosylated human milk oligosaccharides, more preferably complex human milk oligosaccharides, most preferably a lactofucopentaose, by in vitro biocatalysis, wherein a fucosyltransferase is used, said fucosyltransferase being capable of transferring a fucose residue from a donor substrate to an acceptor molecule.

In an embodiment of the in vitro biocatalysis, the method comprises the steps of
a) providing the fucosyltransferase being capable of transferring a fucose residue from a donor substrate to an acceptor molecule in a reaction mixture;
b) contacting said fucosyltransferase with a donor substrate comprising a fucose residue and an acceptor molecule, wherein said acceptor molecule is a lactotetraose, for synthesizing the fucosylated oligosaccharide.

This embodiment comprises providing in a reaction mixture a fucosyltransferase. The term "fucosyltransferase" as used herein also comprises functional variants, functional fragments of said fucosyltransferase and functional variant of fragments of the fucosyltransferase, wherein "functional" denotes that said variants and fragments are capable of possessing a fucosyltransferase activity as described herein before.

The method according to this embodiment further comprises reacting the mixture under conditions appropriate for having the fucose residue transferred from the donor substrate, preferably GDP-fucose, to an acceptor moiety of the acceptor molecule, said acceptor molecule preferably being a lactotetraose.

In an additional embodiment, the method of in-vitro biocatalysis further comprises subsequent purifying and/or isolating the fucosylated acceptor molecule from the reaction mixture.

According to the seventh aspect, provided are fucosylated oligosaccharides being produced by a whole cell fermentation approach or an in-vitro biocatalysis as described herein before.

In an embodiment, the fucosylated oligosaccharide is a human milk oligosaccharide. Selected human milk oligosaccharides are 2'-fucosyllactose, 3-fucosyllactose, 2',3-difucosyllactose, 3-fucosyl-3'-sialyllactose, 3-fucosyl-6'-sialyllactose, lacto-N-fucopentaose I, lacto-N-neofucopentaose III, lacto-N-fucopentaose V, lacto-N-neofucopentaose I, lacto-N-neofucopentaose V, lacto-N-difucosylhexaose I, lacto-N-difucosylhexaose II, fucosyl-lacto-N-sialylpentaose b, fucosyl-lacto-N-sialylpentaose c, lacto-N-neodifucohexaose I, Disialyl-lacto-N-fucopentaose V, and fucosyl-para-lacto-N-hexaose IV. The structures of selected human milk oligosaccharides are displayed in Table 2.

In an embodiment, the fucosylated oligosaccharide that can be produced by utilizing a fucosyltransferase as described herein before is selected from the group consisting of pentasaccharides, preferably selected from the group consisting of lacto-N-fucopentaose I, lacto-N-neofucopentaose I, lacto-N-neofucopentaose III, lacto-N-fucopentaose V, lacto-N-neofucopentaose V.

Notwithstanding that the lactofucopentaoses named in the previous paragraph constitute direct reaction products of the enzymatic activities of the fucosyltransferase described herein before, said lactofucopentaoses may be further processed. For example, said lactofucopentaoses can be provided as acceptor molecules to further glycosyltransferases such that the resulting hexaoses, for example those in Table 2, and heptaoses can also be considered as fucosylated oligosaccharides that can be produced by utilizing the fucosyltransferases as disclosed herein. Moreover, it can be envisaged that the fucosyltransferases can also be employed in producing trisaccharides and/or tetrasaccharides such as those identified in Table 2.

TABLE 2

Structures of exemplary HMOs.

| Name | Abbreviation | Structure |
|---|---|---|
| 2'-Fucosyllactose | 2'-FL | Fuc($\alpha$1-2)Gal($\beta$1-4)Gluc |
| 3-Fucosyllactose | 3-FL | Gal($\beta$1-4)[Fuc($\alpha$1-3)]Gluc |
| 2',3-Difucosyllactose | DF-L | Fuc($\alpha$1-2)Gal($\beta$1-4)[Fuc($\alpha$1-3)]Gluc |
| Lacto-N-fucopentaose I | LNFP I | Fuc($\alpha$1-2)Gal($\beta$1-3)GlcNAc($\beta$1-3)Gal($\beta$1-4)Gluc |
| Lacto-N-neofucopentaose I | LNnFP I | Fuc($\alpha$1-2)Gal($\beta$1-4)GlcNAc($\beta$1-3)Gal($\beta$1-4)Gluc |
| Lacto-N-neofucopentaose III | LNFP III | Gal($\beta$1-4)[Fuc($\alpha$1-3)]GlcNAc($\beta$1-3)Gal($\beta$1-4)Gluc |
| Lacto-N-fucopentaose V | LNFP V | Gal($\beta$1-3)GlcNAc($\beta$1-3)Gal($\beta$1-4)[Fuc($\alpha$1-3)]Gluc |
| Lacto-N-neofucopentaose V | LNnFP V | Gal($\beta$1-4)GlcNAc($\beta$1-3)Gal($\beta$1-4)[Fuc($\alpha$1-3)]Gluc |
| Lacto-N-difucohexaose I | LNDH I | Fuc($\alpha$1-2)Gal($\beta$1-3)[Fuc($\alpha$1-4)]GlcNAc($\beta$1-3)Gal($\beta$1-4)Gluc |
| Lacto-N-difucohexaose II | LND | Gal($\beta$1-3)[Fuc($\alpha$1-4)]GlcNAc($\beta$1-3)Gal($\beta$1-4)[Fuc($\alpha$1-3)]Gluc |
| para-Lacto-N-fucohexaose | paraLNT | Gal($\beta$1-3)GlcNAc($\beta$1-3)Gal($\beta$1-4)[Fuc($\alpha$1-3)]GlcNAc($\beta$1-3)Gal($\beta$1-4)Gluc |
| Fucosyl-lacto-N-sialylpentaose b | F-LST-b | Fuc($\alpha$1-2)Gal($\beta$1-3) [Neu5Ac($\alpha$2-6)]GlcNAc($\beta$1-3)Gal($\beta$1-4)Gluc |
| Fucosyl-lacto-N-sialylpentaose c | F-LST-c | Neu5Ac($\alpha$2-3)Gal($\beta$1-3)GlcNAc($\beta$1-3)Gal($\beta$1-4)[Fuc($\alpha$1-3)]Gluc |
| Disialyl-lacto-N-fucopentaose | DS-LNFP V | Neu5Ac($\alpha$2-3)Gal($\beta$1-4)[Neu5Ac($\alpha$2-6)]GlcNAc($\beta$1-3)Gal($\beta$1-4)[Fuc($\alpha$1-3)]Gluc |
| 3-Fucosyl-3'-sialyllactose | 3F-3'-SL | Neu5Ac($\alpha$2-3)Gal($\beta$1-4)[Fuc($\alpha$1-3)]Gluc |
| 3-Fucosyl-6'-sialyllactose | 3F-6'-SL | Neu5Ac($\alpha$2-6)Gal($\beta$1-4)[Fuc($\alpha$1-3)]Gluc |
| Lacto-N-neodifucohexaose I | LNnDFH I | Gal($\beta$1-4)[Fuc($\alpha$1-3)]GalNAc($\beta$1-3)Gal($\beta$1-4)[Fuc($\alpha$1-3)]Gluc |

According to the eighth aspect, provided is the use of a fucosylated oligosaccharide being produced by a whole cell fermentation approach or an in vitro biocatalysis as described herein before for manufacturing a nutritional composition. Said nutritional composition contains at least one fucosylated oligosaccharide which has been produced by a method as disclosed herein before.

Thus, according to the ninth aspect, provided is a nutritional composition containing at least one fucosylated oligosaccharide which has been produced by a method as disclosed herein before. The at least one fucosylated oligosaccharide is a lactofucopentaose. The at least one lactofucopentaose in the nutritional composition is selected from the group consisting of lacto-N-fucopentaose I, lacto-N-neofucopentaose I, lacto-N-neofucopentaose III, lacto-N-fucopentaose V and lacto-N-neofucopentaose V.

In an additional embodiment, the nutritional composition is selected from the group consisting of medicinal formulations, infant formulations and dietary supplements.

The nutritional composition may be present in liquid form or in solid form including, but not limited to, powders, granules, flakes and pellets.

The present invention will be described with respect to particular embodiments and with reference to drawings, but the invention is not limited thereto but only by the claims. Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description and drawings provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

Example 1: Identification of Fucosyltransferases Fucosylating Lacto-N-Tetraose and Lacto-N-Neotetraose The GenBank database was reviewed for putative fucosyltransferases encoded in the genome of various bacterial species. One hundred twentyfive putative fucosyltransferases which were not annotated as fucosyltransferase before were revealed by this approach.

The genes encoding the putative fucosyltransferases (fucTs) were codon optimized for expression in *E. coli* and purchased from GenScript Cooperation (Piscataway, USA).

The fucosyltransferase genes were subcloned by sequence and ligation-independent cloning (SLIC) in vector pINT-malE-zeo downstream of the malE gene which encodes the maltose-binding protein (MBP) and allows the synthesis of a MBP-fusion protein (FIG. 1), using primers 2700, and 2702 for amplification of the fucT-genes and primers 2701 and 2703 for amplification of pINT-malE-zeo (oligonucleotide primers used are listed in Table 3).

The fucT-genes were expressed in *E. coli* ER 2508 (New England Biolabs, Ipswich, USA). The genes encoding the alpha-1,2-fucosyltransferases wbgL from *E. coli* O126 and fucT2Hp from *Helicobacter pylori* were also codon optimized for expression in *E. coli*, also purchased from GenScript Cooperation, and cloned into the NcoI and BamHI sites of vector pACYC (Novagen, Merck, Darmstadt, Germany) under transcriptional control of the T7 promoter. WbgL and fucT2Hp were amplified with oligonucleotides 141 and 142, and 143 and 144, respectively. The vector as well the PCR amplification products were digested with restriction endonucleases NcoI and BamHI and ligated. *E. coli* transformants were selected on chloramphenicol. WbgL and fucT2HP were expressed in *E. coli* BL21(DE3) ΔlacZ (bacterial strains used in this work are listed in Table 4).

TABLE 3

| | Oligonucleotides used for polymerase chain reactions | |
|---|---|---|
| primer | Sequence (5'-3') | SEQ ID NO: |
| 2700 | AACGCCGCCAGCGGTCGTCAGACTGTCG | 44 |
| 2702 | TAAGCAGAAGGCCATCCTGACGGATGGC | 45 |
| 2701 | GCGGCCGCGTCGACACGCAAAAAGG | 46 |
| 2703 | AGTCTGCGCGTCTTTCAGGGCTTCATCG | 47 |
| 141 | GATCCCATGGAAGTTAAAATCATTGGTGGTC | 48 |
| 142 | GCGCGGATCCTTACAGTTTCACCCAAGATTCCG | 49 |
| 143 | TATACCATGGCTTTTAAGGTGGTGCAAATTTGCGG | 50 |
| 144 | AATTCGGATCCTTAAGCGTTATACTTTTGGGATTTCACC | 51 |
| 1119 | CTGTCTCTTATACACATCTCCTGAAATTGGCCAGATGATTAATTCCTAATTTTTGTTG | 52 |
| 1120 | CTGTCTCTTATACACATCTCAGCATTACACGTCTTGAGCGATTGTGTAGG | 53 |
| 2194 | CTGTCTCTTATACACATCTGGGAATTGATTCTGGTACCAAATGAGTC | 54 |
| 2235 | CTGTCTCTTATACACATCTCCCCAGGCTTTACACTTTATGCTTCC | 55 |
| 6473 | CTGTCTCTTATACACATCTTTACTCAGCAATAAACTGATATTCCGTCAGGCTGG | 56 |
| 6474 | CTGTCTCTTATACACATCTTTCCGTTAACGTCGGTAGTGCTGACCTTGCCGGAGG | 57 |

TABLE 4

| Bacterial strains used | | |
|---|---|---|
| Strain | Genotype | Reference |
| *E. coli* BL21(DE3) | F– ompT hsdSB(rB–, mB–) gal dcm (DE3) | Merck KGaA, Darmstadt, Germany |
| *E. coli* ER 2508 | F– ara-14 leuB6 fhuA2 Δ(argF-lac)U169 lacY1 Ion::miniTn10(Tet$^R$) glnV44 galK2 rpsL20(Str$^R$) xyl-5 mtl-5 Δ(malB) zjc::Tn5(Kan$^R$) Δ(mcrC-mrr)$_{HB101}$ | New England Biolabs, Ipswich, USA |

TABLE 4-continued

Bacterial strains used

| Strain | Genotype | Reference |
| --- | --- | --- |
| E. coli BL21(DE3) ΔlacZ | E. coli BL21(DE3) ΔlacZ | This study |
| E. coli BL21(DE3) 534 | E. coli BL21(DE3) ΔlacZ Δara ΔwcaJ ΔfucIK ΔnagAB harbouring genomic integrations of: galETKM, lacY | This study |
| E. coli BL21(DE3) #724 | E. coli BL21(DE3) ΔlacZ Δara ΔwcaJ ΔfucIK ΔnagAB harbouring genomic integrations of: galETKM, lacY, lgtA-galT-kanR, glmUM-glmS-dhfr | Patent WO 2015/15032811 |
| E. coli BL21(DE3) #753 | E. coli BL21(DE3) ΔlacZ Δara ΔwcaJ ΔfucIK ΔnagAB harbouring genomic integrations of: galETKM, lacY, lgtA-galT-kanR, glmUM-glmS-dhfr, wbdO-galE-cat | This study |
| E. coli BL21(DE3) #993 | E. coli BL21(DE3) ΔlacZ Δara ΔwcaJ ΔfucIK ΔnagAB harbouring genomic integrations of: galETKM, lacY, lgtA-galT-kanR, glmUM-glmS-dhfr, wbdO-galE-cat, fkp-aacC1 | This study |
| E. coli BL21(DE3) #1046 | E. coli BL21(DE3) ΔlacZ Δara ΔwcaJ ΔfucIK ΔnagAB harbouring genomic integrations of: galETKM, lacY, lgtA-galT-kanR, glmUM-glmS-dhfr, lgtB-tetA, galE-cat | This study |
| E. coli BL21(DE3) #1076 | E. coli BL21(DE3) ΔlacZ Δara ΔwcaJ ΔfucIK ΔnagAB harbouring genomic integrations of: galETKM, lacY, lgtA-galT-kanR, glmUM-glmS-dhfr, lgtB-tetA, galE-cat, fkp-aacC1 | This study |
| E. coli BL21(DE3) #1197 | E. coli BL21(DE3) ΔlacZ Δara ΔwcaJ ΔfucIK ΔnagAB harbouring genomic integrations of: galETKM, lacY, lgtA-galT-kanR, glmUM-glmS-dhfr, wbdO-galE-cat, fkp-aacC1, malE-fucT61-zeoR | This study |
| E. coli BL21(DE3) #1369 | E. coli BL21(DE3) ΔlacZ Δara ΔwcaJ ΔfucIK ΔnagAB harbouring genomic integrations of: galETKM, lacYHis-aad1, bbhI-zeoR, lacZ-aacC1 | EP 2 845 905 (A1) |
| E. coli BL21(DE3) #1445 | E. coli BL21(DE3) ΔlacZ Δara ΔwcaJ ΔfucIK ΔnagAB harbouring genomic integrations of: galETKM, lacY, lgtA-galT-kanR, glmUM-glmS-dhfr, wbdO-galE-cat, manC-manB-gmd-wcaG | This study |
| E. coli BL21(DE3) #1772 | E. coli BL21(DE3) ΔlacZ Δara ΔwcaJ ΔfucIK ΔnagAB harbouring genomic integrations of: galETKM, lacY, lgtA-galT-kanR, glmUM-glmS-dhfr, wbdO-galE-cat, fkp-aacC1, malE-fucT61-zeoR, fucP-aad1 | This study |
| E. coli BL21(DE3) #1796 | E. coli BL21(DE3) ΔlacZ Δara ΔwcaJ ΔfucIK ΔnagAB harbouring genomic integrations of: galETKM, lacY, fkp, setA-tetA, malE-fucT109-zeoR | This study |
| E. coli BL21(DE3) #1886 | E. coli BL21(DE3) ΔlacZ Δara ΔwcaJ ΔfucIK ΔnagAB harbouring genomic integrations of: galETKM, lacYHis-aad1, bbhI-zeoR, lacZ-aacC1, bga42A-cat | This study |

E. coli ER 2508 containing pINT-malE-fucT-zeo plasmids were grown in 2YT broth (Sambrook et. al, 1989, supra) containing ampicillin 100 µg/ml and zeocin 40 µg/ml to an OD600 nm of 0.3 before expression of the malE-fucT genes was induced by adding 200 µg/ml anhydrotetracycline. E. coli BL21(DE3) ΔlacZ harbouring pACYC-wbgL or pACYC-fucT2Hp was grown in 2YT broth containing 34 µg/ml chloramphenicol. When an OD600 nm of 0.3 was reached, expression was induced with 0.3 mM IPTG. After 16 h incubation at 30° C. cells were harvested by centrifugation.

Cells were disrupted mechanically using glass beats. Cell free extracts of the expression clones containing equal protein concentrations were incubated in 100 µl fucosyltransferase activity assays for 22 h at 37° C. The assays contained 5 mM GDP-L-fucose, 5 mM LNT or LNnT and 1 mM ATP in 20 mM Tris/HCl, pH 7.4 with 200 mM NaCl.

Formation of fucosylated LNT or LNnT was determined by thin layer chromography (TLC) using silica gel TCL plates (Silica Gel 60 $F_{254}$ (Merck KGaA, Darmstadt, Germany)). A mixture of butanol:acetone:acetic acid:$H_2O$ (35/35/7/23 (v/v/v/v)) was used as mobile phase. For detection of the separated substances the TCL was soaked with Thymol reagent (0.5 g Thymol solved in 95 ml ethanol, 5 ml sulfuric acid added) and heated.

Product formation and identification was additionally determined by mass spectrometry. Mass spectrometry analysis was performed by MRM (multiple reaction monitoring) using a LC Triple-Quadrupole MS detection system (Shimadzu LC-MS 8050) (Shimadzu Corporation, Kyoto, Japan). Precursor ions are selected and analyzed in quadrupole 1, fragmentation takes place in the collision cell using argon as CID gas, selection of fragment ions is performed in quadrupole 3. Selected transitions and collision energies (CE) for intermediates and end-product metabolites are listed in Table 5. Chromatographic separation of lactose, LNT-II, LNT and LNFP variants after dilution of culture supernatant, particle-free biocatalysis-reaction or crude extract, respectively, 1:50 or 1:100 with $H_2O$ (LC/MS Grade), was performed on a XBridge Amide HPLC column LNnFP-III and LNnFP-V have only a slight difference in retention time by 0.1 min. Analysis of in vitro enzyme reactions using the α-1,3-fucosyltransferase FucT109 showed a mixture of LNnFP-III and LNnFP-V (see FIG. 2b).

Table 6 summarizes the fucosyltransferases tested for fucopentaose production and the detected products from the biocatalytic reactions when using LNT, and LNnT as glycan substrate, respectively.

TABLE 5

List of transitions for metabolites analyzed for identification and quantification of intermediates and end-products.

| Metabolite | Transition 1 [m/z Q1 > Q3] | CE | Transition 2 [m/z Q1 > Q3] | CE | Transition 3 [m/z Q1 > Q3] | CE |
|---|---|---|---|---|---|---|
| Lactose [M − H] | 341.00 > 161.15 | 9 | 341.00 > 101.05 | 15 | 341.00 > 179.15 | 7 |
| LNT-II [M − H] | 544.20 > 161.00 | 16 | 544.20 > 382.10 | 11 | 544.20 > 112.90 | 28 |
| LNT [M − H] | 706.20 > 202.10 | 22 | 706.20 > 142.00 | 31 | 706.20 > 382.10 | 17 |
| LNnT [M − H] | 706.10 > 179.20 | 29 | 706.10 > 263.25 | 21 | 706.10 > 382.30 | 17 |
| LNFP-I [M − H] | 852.10 > 690.20 | 16 | 852.10 > 325.10 | 23 | 852.10 > 205.20 | 40 |
| LNnFP-I [M − H] | 852.30 > 409.20 | 29 | 852.30 > 427.20 | 22 | 852.30 > 205.15 | 49 |
| LNFP-II [M − H] | 852.30 > 348.20 | 23 | 852.30 > 163.05 | 40 | 852.30 > 288.20 | 29 |
| LNnFP-III [M − H] | 852.30 > 364.10 | 21 | 852.30 > 179.10 | 35 | 852.30 > 161.15 | 30 |
| LNFP-V [M − H] | 852.30 > 544.20 | 15 | 852.30 > 202.15 | 29 | 852.30 > 142.15 | 44 |
| LNnFP-V [M − H] | 852.30 > 544.20 | 13 | 852.30 > 179.15 | 38 | 852.30 > 281.15 | 24 |

(3.5 µm, 2.1×50 mm (Waters, USA). Before applying to the LC/MS analyses samples were prepared by filtering (0.22 µm pore size) and clearing by solid phase extraction on an ion exchange matrix (Strata ABW, Phenomenex). The HPLC system consists of a Shimadzu Nexera X2 SIL-30AC$_{MP}$ Autosampler run at 8° C., a Shimadzu LC-20AD Pump, and a Shimadzu CTO-20AC column oven that was run at 35° C. (Shimadzu Corporation, Kyoto, Japan). The mobile phase was composed of acetonitrile:$H_2O$ with 0.1% (v/v) ammonium hydroxide. A 1 µl sample was injected into the instrument; the run was performed for 5.00 min with a flow rate of 300 µl/min. All metabolites were analyzed by MRM in ESI negative ionization mode. The mass spectrometer was operated at unit resolution. Collision energy, Q1 and Q3 Pre Bias were optimized for each analyte individually. Quantification methods were established using commercially available standards (Carbosynth, Compton, U K and Elicityl, Crolles, France).

LNFP variants based on the fucosylation of the intermediate Lacto-N-tetraose (LNT) can be identified by chromatographic separation (LNFP-I—2.4 min; and LNFP-V—2.5 min). The slightly different retention times are caused by the difference in the type of fucosylation of LNT (alpha-1,2-fucosylation on galactose for LNFP-I; alpha-1,4-fucosylation on N-acetyl-glucosamine for LNFP-II and alpha-1,3-fucosylation on glucose for LNFP-V). In addition, they can be identified by their transition pattern (see Table 5) due to specific fragmentation patterns related to the position of the fucosylation.

Figure 2A:
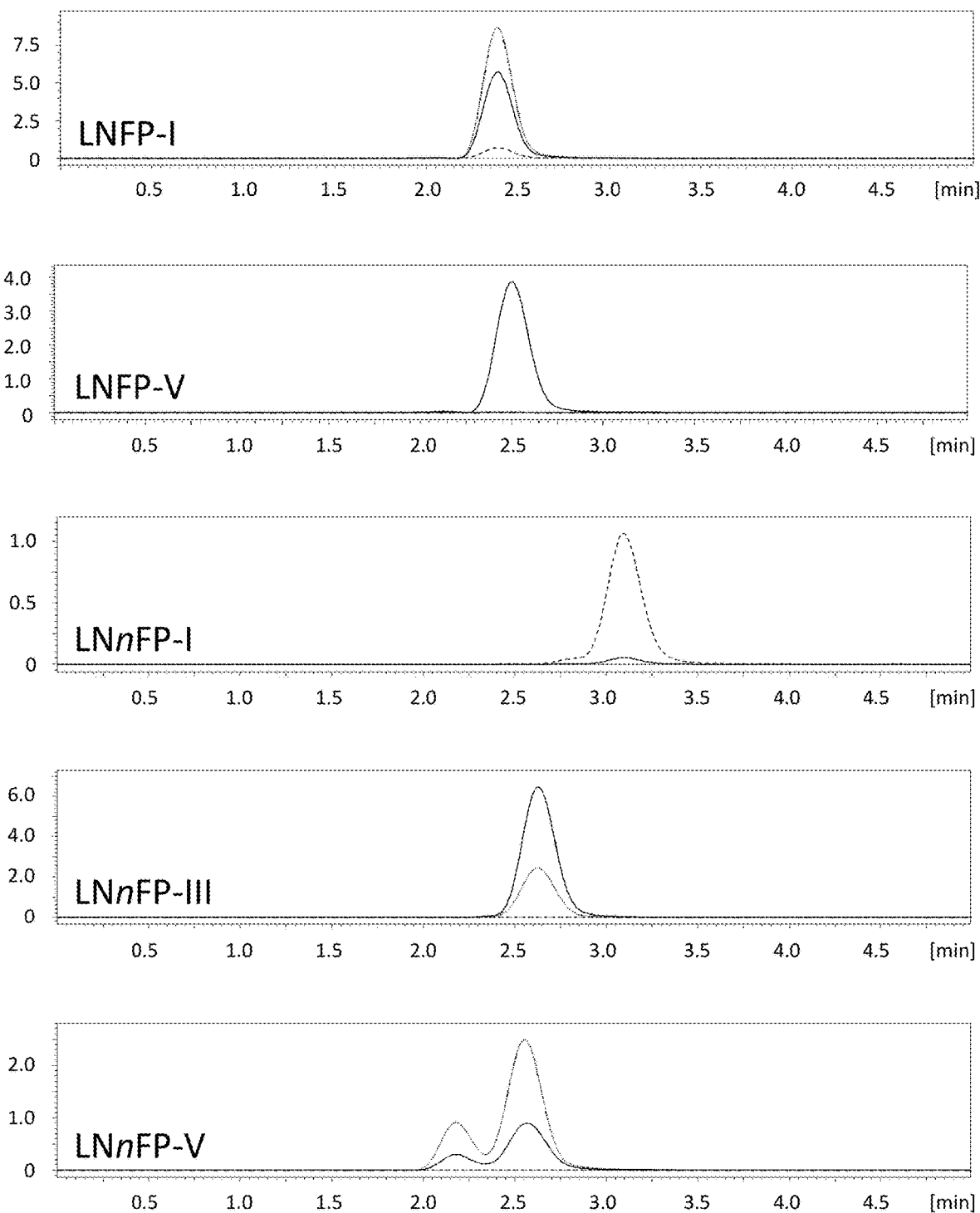
FIG. 2a and 2b show chromatograms of LC/MS analyses of fucosylated type 1 (core structure: Gal(β1,3)GlcNAc) and type 2 (core structure: Gal(β1,4)GlcNAc) products.
Figure 2B:
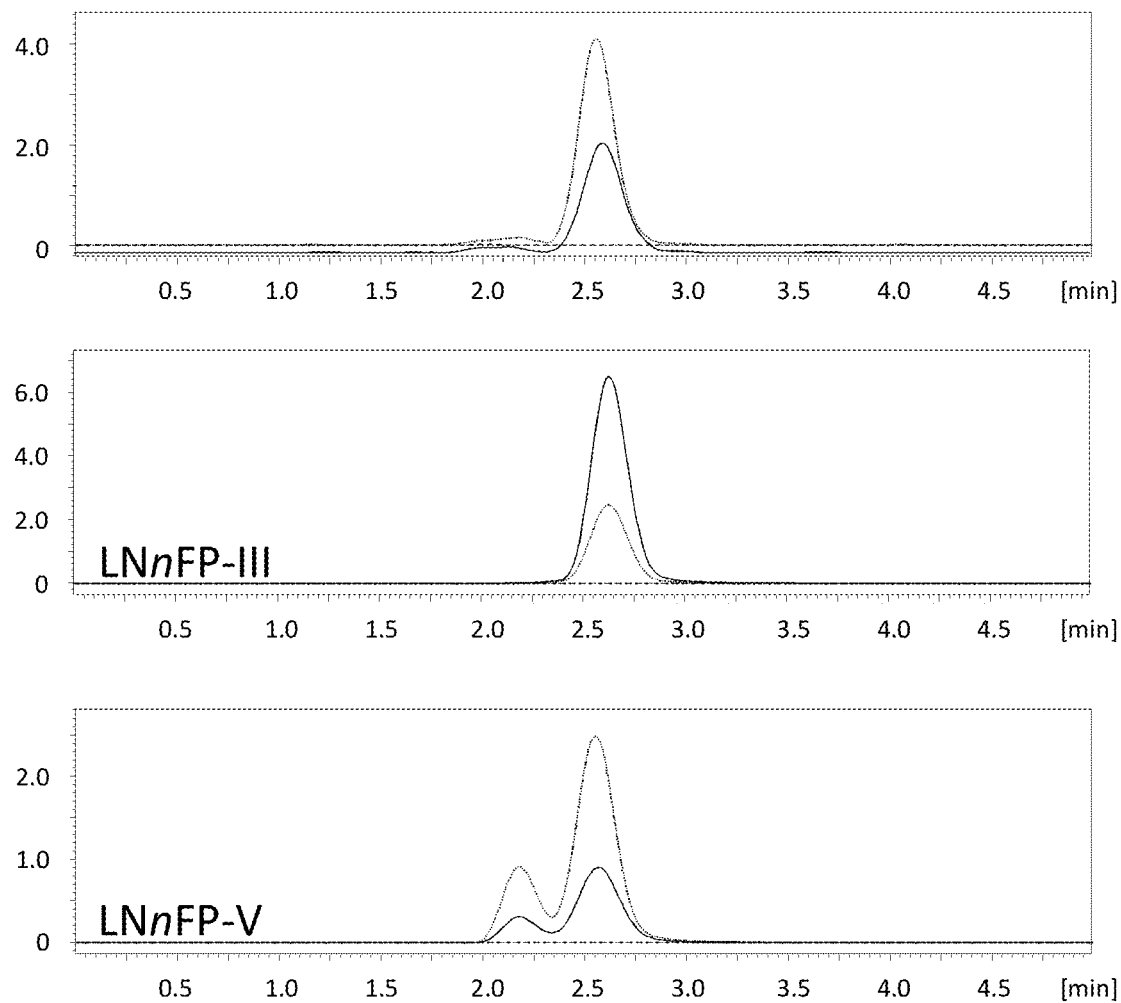

LNnFP variants based on the difference in position of the fucosylation (alpha-1,2-fucosylation on galactose for LNnFP-I and alpha-1,3-fucosylation on N-acetylglucosamine for LNnFPIII and on glucose for LNnFP-V) of the intermediate Lacto-N-neotetraose (LNnT) can be identified by chromatographic separation (FIG. 2a). In addition, they can be identified by their transition pattern (see Table 5) due to specific fragmentation patterns related to the position of the fucosylation.

Example 2: Development of an *E. coli* Lacto-N-Triose II Production Strain

*Escherichia coli* BL21(DE3) was used to construct a lacto-N-triose II (LNT-2) producing strain. Metabolic engineering included mutagenesis and deletions of specific genes, respectively, and genomic integrations of heterologous genes. The genes lacZ and araA were inactivated by mutagenesis using mismatch-oligonucleotides.

Genomic deletions were performed according to the method of Datsenko and Wanner. To prevent intracellular degradation of N-acetylglucosamine, genes encoding N-acetyl-glucosamine-6-phosphate deacetylase (nagA) and glucosamine-6-phosphate deaminase (nagB) were deleted from the genome of the *E. coli* strain BL21 (DE3) strain. Also genes wzxC-wcaJ were deleted. WcaJ encodes an UDP-glucose:unde-caprenyl phosphate glucose-1-phosphate transferase catalysing the first step in colanic acid synthesis. In addition, the genes fucI and fucK, coding for L-fucose isomerase and L-fuculose kinase, respectively, were removed.

Genomic integration of heterologous genes was performed by transposition. Either the EZ-Tn5™ transposase (Epicentre, USA) was used to integrate linear DNA-fragments or the hyperactive C9-mutant of the mariner transposase Himar1 was employed for transposition. To produce EZ-Tn5 transposomes the gene of interest together with a FRT-site flanked antibiotic resistance marker was amplified with primers 1119 and 1120; the resulting PCR-product carried on both sites the 19-bp Mosaic End recognition sites for the EZ-Tn5 transposase. For integration using Himar1 transposase expression constructs (operons) of interest were similarly cloned together with a FRT-site flanked antibiotic resistance marker into the pEcomar vector. The pEcomar vector encodes the hyperactive C9-mutant of the mariner transposase Himar1 under the control of the arabinose inducible promoter P$_{araB}$. The expression fragment <P$_{tet}$-lacY-FRT-aadA-FRT> (SEQ ID NO: 31) was integrated by using the EZ-Tn5 transposase. After successful integration of the gene for the lactose importer LacY from *E. coli* K12 TG1 (acc. no. ABN72583) the resistance gene was eliminated from streptomycin resistant clones by the FLP recombinase encoded on plasmid. The strain obtained by that modifications was strain #534. The N-acetylglucosamine glycosyltransferase gene lgtA from *Neisseria meningitidis* MC58 (acc. no. NP_274923) was codon-optimized for expression in *E. coli* and prepared synthetically by gene synthesis. Together with the gene galT, encoding a galactose-1-phosphate uridylyltransferase from *E. coli* K-12 substr. MG1655 (acc. no. NP_415279) that was similarly obtained by gene synthesis, lgtA was inserted by transposition (SEQ ID NO: 32) using plasmid pEcomar-IgtA-galT. To enhance de novo synthesis of UDP-N-acetylglucosamine, genes encoding L-glutamine:D-fuctose-6-phosphate aminotransferase (glmS), phosphoglucosamine mutase from *E. coli* K-12 substr. MG1655 (glmM) and N-acetylglucosamine-1-phosphate uridyltransferase/glucosamine-1-phosphate acetyltransferase (glmU) from *E. coli* K-12 substr. MG1655 (acc. no. NP_418185, NP_417643, NP_418186, respectively) were codon-optimized and obtained by gene synthesis. The operon glmUM was cloned under the control of constitutive tetracycline promoter $P_{tet}$ while glmS was cloned under the constitutive PT5 promoter. The transposon cassette <$P_{tet}$-glmUM-$P_{T5}$-glmS-FRT-dhfr-FRT> (SEQ ID NO: 33), flanked by the inverted terminal repeats specifically recognized by the mariner-like element Himar1 transposase was inserted from pEcomar-glmUM-glmS revealing a lacto-N-triose 2 production strain (#724). The strain *E. coli* BL21(DE3) was used as initial host strain for the development of the *E. coli* production strain.

Example 3: Engineering of an *E. coli* Strain to Screen Fucosyltransferases In Vivo for Producing Fucosylated LNT The 1,3-galactosyltransferase gene wbdO from *Salmonella salamae* (acc. no. AAV34525) was codon-optimized for expression in *E. coli* and prepared synthetically by GenScript cooperation. The galE gene was amplified from genomic DNA of *E. coli* K12. Both genes were inserted as <$P_{tet}$-wbdOco-$P_{T5}$-galE-FRT-cat-FRT> (SEQ ID NO: 34) transposon into the strain #724 by transposition using plasmid pEcomar-wbdO-galE. The resulting strain is #753. To enhance the supply of GDP-fucose, the bifunctional fucosekinase/L-Fucose-1-phosphate-guanyltransferase (fkp) from *Bacteroides fragilis* (accession no. AY849806) converting L-fucose into GDP-fucose was overexpressed in the *E. coli* BL21 (DE3) strain. The fkp gene (originally amplified from genomic DNA of *Bacteroides fragilis* (ATCC 25285D)) together with a preceding promoter $P_{tet}$ was fused to the lox-site flanked gentamycin resistance gene using splicing by overlap extension PCR (SOE-PCR) and primers 1119 and 1120; the resulting EZ-Tn5<$P_{tet}$-fkp-lox-aacC1-lox> (SEQ ID NO: 35) transposon was integrated in the *E. coli* BL21(DE3) strain mediated by the EZ-Tn5™ transposase, obtaining strain #993. Alternatively, for the de novo synthesis of GDP-L-fucose genes encoding phosphomannomutase (manB), mannose-1-phosphate guanosyltransferase (manC), GDP-mannose-4,6-dehydratase (gmd), and GDP-L-fucose synthase (wcaG) from *E. coli* K12 DH5α were overexpressed in the *E. coli* BL21(DE3) strain; the operon manCB was set under control of the constitutive promoter $P_{tet}$, the operon gmd, wcaG is transcribed from the also constitutive PT5 promoter. The transposon cassette <$P_{tet}$-manCB-$P_{T5}$-gmd, wcaG-FRT-aacC1-FRT> (SEQ ID NO: 36), including the gene aacC1 conferring a gentamycin resistance to the bacterial host was flanked by the inverted terminal repeats specifically recognized by the mariner-like element Himar1 transposase. It was inserted into the genome of strain #753 from pEcomar C9-manCB-gmd, wcaG-aacC1, yielding strain #1445.

Example 4: Engineering of an *E. coli* Strain to Screen Fucosyltransferases In Vivo for Producing Fucosylated LNnT The β-1,4-galactosyltransferase genes lgtB from *Neisseria meningitides* (acc. no. AAF42257) was optimized for expression in *E. coli* and prepared synthetically by GenScript cooperation. Together with a FRT-site flanked tetracycline resistance gene it was inserted as <$P_{T5}$-IgtB-FRT-tetA-FRT> (SEQ ID NO: 37) transposon into the strain #724 by transposition using plasmid pEcomar-IgtB. The galE gene was amplified from genomic DNA of *E. coli* K12 and fused by SOE-PCR with the promoter $P_{tet}$ and a chloramphenicol resistance gene. Using primers that generate 19-bp Mosaic End recognition sites for the EZ-Tn5 transposase (primer 2194 and 2235) the EZ-transposon <$P_{tet}$-galE-FRT-cat-FRT> was constructed to be integrated into the *E. coli* BL21(DE3) strain to obtain strain #1046. Alternatively, the β-1,4-galactosyltransferase gene lex1 from *Aggregatibacter aphrophilus* NJ8700 (acc. no. YP_003008647), synthetically synthesised and codon optimized for *E. coli*, was integrated into strain #724. The lex1 gene was fused to the malE gene, encoding the maltose binding protein (MBP), obtaining a N-terminal fusion of MBP to Lex1. The malE-lex1 fusion was integrated concomitantly with galE (SEQ ID NO: 38), under transcriptional control of the Ret promoter, by transposition using pEcomar-malE-lex1-galE-cat. Using EZ-fragment EZ-Tn5<$P_{tet}$-fkp-FRT-aacC1-FRT> (see Example 3) the gene encoding the fucosekinase/L-Fucose-1-phosphate-guanyltransferase (fkp) from *Bacteroides fragilis* was chromosomally integrated in strain #1046, yielding strain #1076.

Example 5: In Vivo Screening of Fucosyltransferases Fucosylating LNT, and LNnT

The mineral salts (MS) medium used for cultivation of strains for the synthesis of fucopentaoses contained 7 g/L $NH_4H_2PO_4$, 7 g/L $K_2HPO_4$, 2 g/L KOH, 0.3 g/L citric acid, 2 g/L $MgSO_4 \times 7H_2O$, and 0.015 g/L $CaCl_2 \times 6H_2O$, supplemented with 1 mL/L trace element solution (54.4 g/L ammonium ferric citrate, 9.8 g/L $MnCl_2 \times 4H_2O$, 1.6 g/L $CoCl_2 \times 6H_2O$, 1 g/L $CuCl_2 \times 2H_2O$, 1.9 g/L $H_3BO_3$, 9 g/L $ZnSO_4 \times 7H_2O$, 1.1 g/L $Na_2MoO_4 \times 2H_2O$, 1.5 g/L $Na_2SeO_3$, 1.5 g/L $NiSO_4 \times 6H_2O$).

Using strains #993 or #1445 for LNT, and #1076 for LNnT as FucT substrates, respectively, plasmids pINT-malE-fucT-zeo were used to produce fucosylated pentasaccharides in vivo. The plasmid containing strains were grown in 20 ml mineral salt (MS) medium with 2% glucose as carbon source, 200 ng/ml anhydrotetracycline as inducer for gene expression and the antibiotics ampicillin 100 µg/ml, and zeocin 20 µg/ml. The bacteria were cultivated at 30° C. in baffled shaking flasks to an $OD_{600nm}$ of 0.3 before 3 mM lactose and 2 mM L-fucose for derivatives of strain #993, and #1076, and 3 mM lactose for derivatives of strain #1445 were added.

After 24 h to 72 h of cultivation cells were harvested by centrifugation, washed once in saline (0.9% (w/v) NaCl), resuspended in 150 µl to 200 µl saline (depending on the pellet size), and disrupted mechanically using glass-beats.

Figure 4:
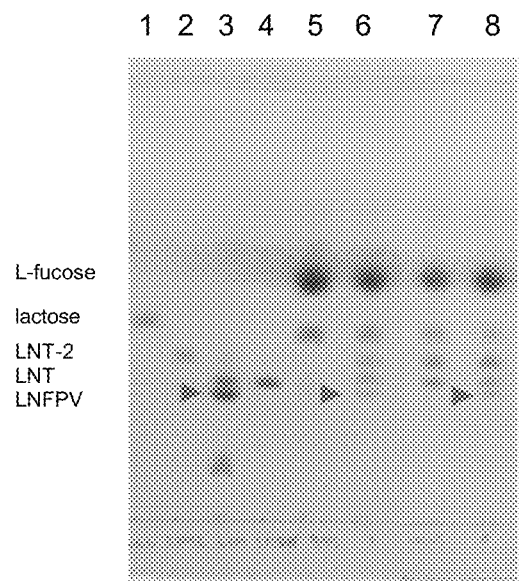
FIG. 4 depicts a TLC analyses of culture supernatants of lacto-N-fucopentaose producing *E. coli* strains containing pINT-malE-fucT109-zeo.

Clear supernatant was achieved by palletising the cell debris. The formation of fucosylated LNT was detected by analysing the intracellular metabolites by TLC, the results are summarized in Table 6. In order to analyse the formation of LNFP-V by FucT109 from *Bacteroides fragilis* NTCT 9343 that is secreted in the culture supernatant, intact cells were centrifuged and the supernatant was applied to a TLC analysis (FIG. 4). FIG. 4 depicts a TLC analyses of culture supernatants of lacto-N-fucopentaose producing *E. coli* strains, containing pINT-malE-fucT109-zeo. LNFP-V is detected in the supernatant of strains expressing the malE-fucT109 fusion gene by comparing the migration rate to purified a standard sugar. Reference sugars: lane 1: lactose; lane 2: LNT-2, lane 3: LNT+LNFP-V, lane 4: LNT; lane 5: supernatant sample from strain #993, lane 6: supernatant sample from strain #993 pINT-malE-fucT109-zeo, lane 7: supernatant sample from strain #1445, lane 8: supernatant sample from strain #1445 pINT-malE-fucT109-zeo.

Example 6: Synthesis of LNFP-I in a Fermentative Process

Integration of fucT Genes in *E. coli* BL21(DE3) Derivatives

Using strain #993 as host, the genes encoding fucosyltransferases fucT41 (*Gramella forsetii* KT0803, acc. No. WP_011708479), FucT 48 (*Francisella philomiragia* ssp. *philomiragia* ATCC 25015, acc. No. EET21243.1), FucT49 (*Pseudogulbenkiania ferrooxidans*, acc. No. EEG10438.1), FucT54 (*Sideroxydans lithotrophicus* ES-11, acc. No. ADE13114.1), FucT61 (*Pseudoalteromonas haloplanktis* ANT/505, acc. No. EG174693.1), FucT66 (*Roseovarius nubinhibens* ISM, acc. No. EAP78457.1), and FucT69 (*Thalassospira profundimaris* WP0211, acc. No. EKF09232.1), were chromosomally integrated. The malE-fucT fusion gene together with the preceding promoter $P_{tet}$ and the zeocine resistance gene was amplified with primers 1119 and 1120 using pINT-malE-fucT-zeo plasmids as templates; the transposon cassette EZ-Tn5<$P_{tet}$-malE-fucT-zeo> was inserted in the *E. coli* BL21(DE3) strain using the EZ-Tn5™ transposase.

Figure 5:
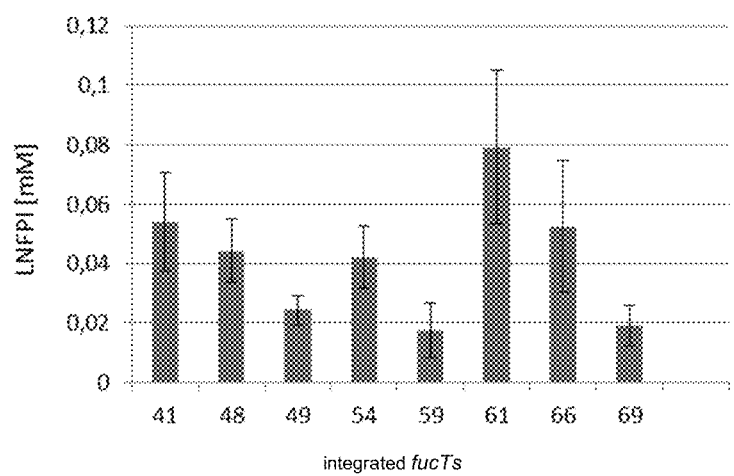
FIG. 5 shows a bar graph which demonstrates production of extracellular LNFP-I by *E. coli* (strain #993) after chromosomal integration of different fucT genes.

The strains harboring the malE-fucT integration were grown at 30° C. in 96-well pates in 200 µl MS medium containing 2% glucose, and 20 µg/ml zeocin with shaking. After 24 h cultivation, 50 µl of the cultures were transferred into 400 µl fresh MS-medium with 2% glucose, 20 µg/ml zeocin, 3 mM lactose and 2 mM L-fucose. After 48 h of cultivation the supernatants of the cultures were analyzed by LC/MS. Results for different FucT genes are shown in FIG. 5, wherein error bars display standard deviation of five separate cultures of the same strain. The fucT61 expressing strain (#1197) achieved the highest LNFP-I titer compared to the other integrants (FIG. 5).

Engineering of the Fucose Import for the Production of LNFP-I

Enhanced LNFP-I production by strain 1197 was achieved by integration of the major facilitator transporter FucP of *E. coli* MG1655 (acc. no. AIZ90162). FucP together with a preceding $P_{tet}$ promoter and a streptomycin resistance gene was amplified with primer 1119 and 1120 (<$P_{tet}$-fucP-FRT-aad1-FRT>, SEQ ID NO: 39) and chromosomally integrated by transposition using the EZ Tn5™ transposase. The strain with fucT61 and fucP was named as strain #1772.

Growing strains #1197 and #1772 in 96-well plates in MS medium with 2% glucose as carbon source in the presents of 3 mM lactose and 2 mM L-fucose, the LNFP-I concentration detected in the supernatant of strain #1772 was twice of that found in the supernatant of strain #1197.

Production of LNFP-I by Fermentation

Figure 6:
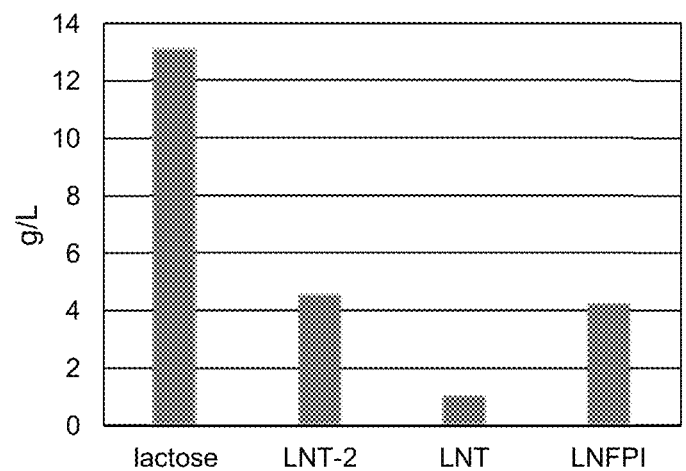
FIG. 6 shows a bar graph which demonstrates production of LNFP-I by *E. coli* (strain #1772) in a 1 L-fermentation using glucose as carbon source.

Pilot fermentation of strain #1772 was conducted at 30° C. in a 3 L-fermentor containing 1 L MS-medium. 2% glucose and 2.5 g/L NH$_4$Cl were added to the medium prior to inoculation; the fermentation was carried out without the addition of antibiotics. The pH was held constantly at 7.0 by titrating with 10% ammonia. The fermenter was seeded with cultures from shake flasks to an OD600 nm of 0.1. At an OD600 nm of about 10 1 mM lactose and 1 mM L-fucose were added; the two substrates were fed in 1-2 mM doses repeatedly according to grows and production rates. When the glucose batch of 2% was depleted, glucose was fed continuously from a 50% glucose stock. After 87 h of cultivation the culture reached an OD600 nm of 185. A LNFP-I concentration of 4.3 g/L was determined in the culture supernatant by LC/MS analysis. Lactose, LNT-2, and LNT were found as sugar by-products in the supernatant (FIG. 6). The graphic of FIG. 6 demonstrates the production of LNFP-I by *E. coli* (strain #1772) in a 1 L-fermentation using glucose as carbon source. The product concentrations were measured in the culture supernatant after 87 h of fermentation. Besides LNFP-I (4.3 g/L), lactose (13.11 g/L), LNT-2 (4.6 g/L), and LNT (1.1 g/L) were detected in the supernatant.

TABLE 6

Fucosyltransferases analysed in this study. Fucosyltransferase activities were determined using LNT and LNnT as glycan substrates. Formation of fucopentaoses was determined as well in vitro, as in vivo, using whole cell transformation. Identification of the fucopentaose was performed by LC/MS.

| FucT | source | acc. No. | predicted function | In vivo fucosylation of LNT | In vivo fucosylation of LNnT | In vitro fucosylation of LNT | product | In vitro fucosylation of LNnT | product |
|---|---|---|---|---|---|---|---|---|---|
| fucT2 | *Helicobacter hepaticus* ATCC 51449 | AAP76669 | α-(1,3)-fucosyltransferase | + | – | – | – | + | LNFP-III |
| fucT22 | *Brachyspira pilosicoli* WesB | CCG56842 | α-(1,2)-fucosyltransferase | n.t. | + | + | LNFP-I | – | – |
| fucT32 | *Yersinia* sp. A125 KOH2 | CAI39173 | α-(1,2)-fucosyltransferase | + | – | + | LNFP-I | – | – |
| fucT41 | *Gramella forsetii* KT0803 | WP_011708479 | putative α-(1,2)-fucosyltransferase | + | – | + | LNFP-I | – | – |
| fucT48 | *Francisella philomiragia* ssp. *philomiragia* ATCC 25015 | EET21243.1 | putative α-(1,2)-fucosyltransferase | + | + | + | LNFP-I | – | – |

TABLE 6-continued

Fucosyltransferases analysed in this study. Fucosyltransferase activities were determined using LNT and LNnT as glycan substrates. Formation of fucopentaoses was determined as well in vitro, as in vivo, using whole cell transformation. Identification of the fucopentaose was performed by LC/MS.

| FucT | source | acc. No. | predicted function | In vivo fucosylation of LNT | In vivo fucosylation of LNnT | In vitro fucosylation of LNT | product | In vitro fucosylation of LNnT | product |
|---|---|---|---|---|---|---|---|---|---|
| fucT49 | *Pseudogulbenkiania ferrooxidans* | EEG10438.1 | putative α-(1,2)-fucosyltransferase | + | − | + | LNFP-I | − | − |
| fucT54 | *Sideroxydans lithotrophicus* ES-11 | ADE13114.1 | putative α-(1,2)-fucosyltransferase | + | − | + | LNFP-I | − | − |
| fucT55 | *Providencia alcalifaciens* | AFH02807.1 | putative α-(1,2)-fucosyltransferase | − | − | + | LNFP-I | − | − |
| fucT61 | *Pseudoalteromonas haloplanktis* ANT/505 | EGI74693.1 | α-(1,2)-fucosyltransferase | + | − | − | − | − | − |
| fucT66 | *Roseovarius nubinhibens* ISM | EAP78457.1 | putative α-(1,2)-fucosyltransferase | + | − | + | LNFP-I | − | − |
| fucT69 | *Thalassospira profundimaris* WP0211 | EKF09232.1 | glycosyl transferase family 11 | + | + | − | − | − | − |
| fucT73 | *Desulfovibrio alaskensis* (strain G20) | ABB39672.1 | glycosyl transferase family 11 | n.t. | + | + | LNFP-I | − | − |
| fucT92 | *Thermosynechococcus elongatus* (strain BP-1) | BAC08546.1 | α-1,2-fucosyltransferase | n.t. | + | + | LNFP-I | − | − |
| fucT109 | *Bacteroides fragilis* (strain ATCC 25285/ NCTC 9343) | CAH09151.1 | putative LPS biosynthesis related glycosyltransferase | + | + | + | LNFP-V | + | LNFP-III/ LNnFP-V |
| wbgL | *Escherichia coli* O126 | ABE98421 | α-(1,2)-fucosyltransferase | n.t. | n.t. | + | LNFP-I | + | LNnFPI |
| fucT2 | *Helicobacter pylori* | AAD29863 | α-(1,2)-fucosyltransferase | n.t. | n.t. | + | LNFP-I | + | LNnFPI |

+ designates the detection of a reaction product, − designates no activity, n.t. means not tested.

Degradation of by-Products

To facilitate separation of the desired product LNFP-I from the by-products lactose, LNT-2, and LNT, these sugars can be enzymatically digested, and the resulting degradation products are metabolized by *E. coli* strains.

β-1,4-galactosidases, e.g. LacZ of *E. coli* efficiently degrades lactose to D-glucose and d D-galactose. These two monosaccharides are metabolized by *E. coli* strains expressing a functional gal-operon.

The β-N-acetylhexosaminidase Bbhl from *Bifidobacterium bifidum* JCM1254 hydrolyses LNT-2 highly specific and efficient to N-acetylglucosamine and lactose.

The β-1,3-galactosidases Bga42A from *Bifidobacterium longum* subsp. *infantis* hydrolyses LNT specifically to galactose and LNT-2.

Engineering of an *E. coli* Strain for Degradation of by-Products

*Escherichia coli* BL21(DE3) #534 was used to construct a degradation strain in order to recover LNFP-I after fermentative production from the supernatant without sugar by-products.

A functional galETKM operon together with its natural promoter was amplified from genomic DNA of *E. coli* K12 using oligonucleotides 6473 and 6474, producing a fragment with 5' 19-bp Mosaic End recognition sites for the EZ-Tn5 transposase. The fragment <galETKM> (SEQ ID NO: 40) was integrated into the genome of the *E. coli* strain mediated by the EZ-Tn5™ transposase. Clones with correct integrations were selected on MacConcey agar (Difco, Sparks, USA) containing 1% galactose, they appeared as red colonies after 36 h incubation at 37° C.

The gene encoding the β-N-acetylhexosaminidase Bbhl from *Bifidobacterium bifidum* JCM1254 was synthesized synthetically and codon optimizes for the expression in *E. coli*. Bbhl under transcriptional control of the $P_{tet}$ promoter and a gene conferring to the host a zeocin resistance (<$P_{tet}$-bbhl-zeo> (SEQ ID NO: 41) was integrated from plasmid pEcomar-bbhl-zeo mediated by the Himar1 transposase.

To ensure full β-1,4-galactosidases activity, lacZ from *E. coli* BL21(DE3) (acc. No. AM946981) was cloned under the transcriptional control of the constitutive promoter $P_{tet}$. Together with the gentamycin resistance gen aacC1 the fragment <$P_{tet}$-lacZ-FRT-aacC1-FRT> (SEQ ID NO: 42) was amplified with primers 1119 and 1120 and integrated by EZ Tn5 transposition, obtaining strain #1369.

The β-1,3-galactosidases Bga42A from *Bifidobacterium longum* subsp. *infantis* was codon optimized for *E. coli* and synthesised synthetically. Bga42A under transcriptional control of the $P_{tet}$ promoter and the cat gene conferring to the host a chloramphenicol resistance (<$P_{tet}$-bga42A-cat> (SEQ ID NO: 43) was integrated using the EZTn5 transposase. The strain expressing all three hydrolase genes is designated as strain #1886.

Degradation of lactose and LNT-2 was achieved efficiently by adding a culture of strain #1886 to a LNFP-I producing culture of strain #1772. To demonstrate the degradation of LNT-2 and lactose by LacZ and Bbhl, a culture of strain #1886, grown in MS medium with glucose as carbon source was added in a volume ratio of 1:40 to a culture of strain #1772, grown in MS medium with glucose in the presence of lactose and L-fucose for the production of LNFP-I.

Figure 7:
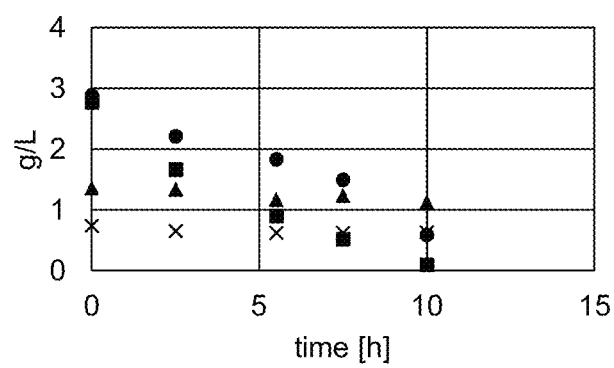
FIG. 7 shows a graph illustrating degradation of LNT-2 and lactose by hydrolases expressed in *E. coli* strain #1886.

FIG. 7 demonstrates degradation of lactose and LNT-2 by hydrolases being expressed in *E. coli* strain #1886. A growing culture of *E. coli* strain #1886 was added to a culture of *E. coli* strain #1772 that produced LNFP-I as main product and LNT, and LNT-2 as by-products. LNT-2 and lactose were nearly completely depleted in the culture supernatant within 10 h of incubation. Metabolites are marked as, circles: lactose, squares: LNT-2, triangles: LNFP-I, crosses: LNT. Within 10 h LNT-2 and lactose were degraded to near complete depletion, while LNFP-I and LNT were not degraded by the #1886 cells. Since strain #1886 contains an active galETKM-operon the monosaccharides glucose and galactose resulting from lactose hydrolyses are completely metabolized.

Figure 8:
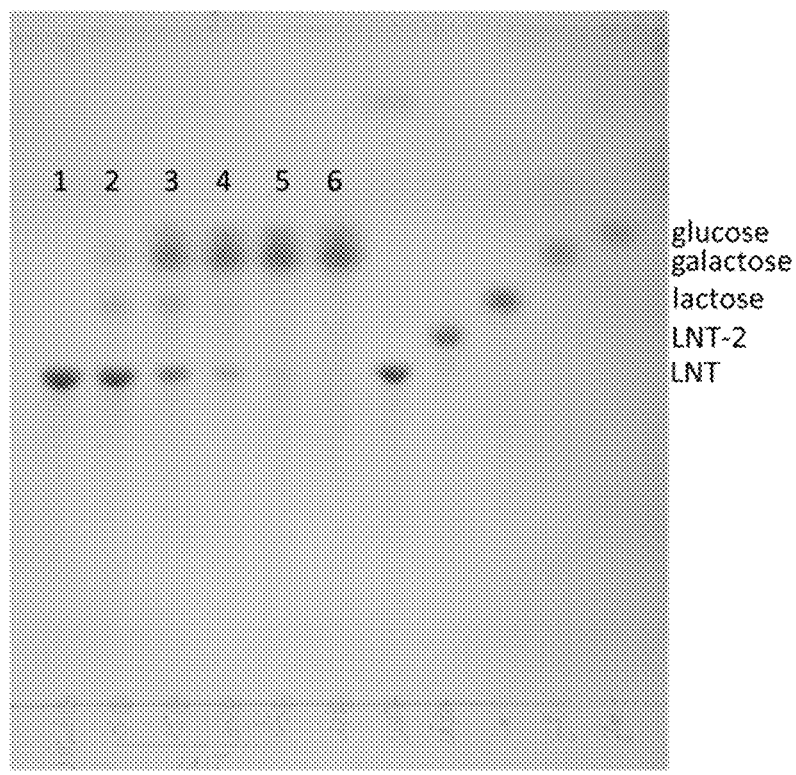
FIG. 8 shows an image of a thin layer chromatography illustrating time dependent LNT degradation by the β-1,3-galactosidase Bga42A.

The hydrolase Bga42A is not active extracellularly. However, when cells of strain #1886, grown on MS medium with glucose as carbon source, were disrupted mechanically, hydrolytic activity of Bga42A towards LNT was demonstrated as shown in FIG. 8 displaying an image of a thin layer chromatogram. Samples containing cell lysate from *E. coli* strain #1886 (lane 1: no enzyme, lanes 2 to 6: 100 μg protein) and 5 mM LNT in a 20 mM sodium-phosphate buffer pH 7 were incubated over a time period of up to 120 minutes (lane 1: 120 min, lane 2: 0 min, lane 3: 15 min, lane 4: 30 min, lane 5: 60 min, lane 6: 120 min) at 30° C. and before the enzyme was inactivated by heating at 95° C. for 5 minutes.

In FIG. 8 hydrolyses of LNT and the resulting degradation products LNT-2 and lactose in cell free extract of strain #1886 is shown.

The invention claimed is:

1. A method for producing a fucosylated oligosaccharide, the method comprising:
   a) providing at least one genetically engineered cell that has been engineered to express a heterologous fucosyltransferase, wherein the heterologous fucosyltransferase comprises an amino acid sequence having at least 80% sequence identity to one of SEQ ID NOs: 17-26 and 28-30, wherein the fucosyltransferase is capable of transferring a fucose residue from a donor substrate to an acceptor molecule;
   b) cultivating by fermentation the at least one genetically engineered cell in the presence of at least one carbon source, an acceptor molecule being a lactotetraose, and a donor substrate, comprising a fucose residue, and under conditions suitable for the at least one genetically engineered cell to transfer the fucose residue from the donor substrate to the acceptor molecule to produce the fucosylated oligosaccharide.

2. The method according to claim 1, wherein the acceptor molecule is selected from the group consisting of Lacto-N-tetraose (LNT) and Lacto-N-neotetraose (LNnT).

3. The method according to claim 2, wherein the acceptor is LNT and the heterologous fucosyltransferase is selected from the group consisting of SEQ ID NOs: 18-22, 24, 25, 28 and 30, functional variants of the polypeptides of SEQ ID NOs: 18-22, 24, 25, 28 and 30 having at least 80% sequence identity to SEQ ID NOs: 18-22, 24, 25, 28, and 30.

4. The method according to claim 2, wherein the acceptor is LNnT and the heterologous fucosyltransferase is selected from the group consisting of SEQ ID NOs: 17, 20, 26, 28, and 30, and functional variants of the polypeptides of SEQ ID NOs: 17, 20, 26, 28 and 30 having at least 80% sequence identity to SEQ ID NOs: 17, 20, 26, 28, and 30.

5. The method according to claim 2, wherein the fucosyltransferase is encoded by a gene with a sequence selected from the group consisting of SEQ ID NOs: 5, 11, and 14.

6. The method according to claim 5, wherein the gene has the sequence of SEQ ID NO: 14.

7. The method according to claim 2, wherein the acceptor molecule is LNT and the fucosyltransferase is encoded by a gene having a sequence selected from the group consisting of SEQ ID NOs: 3-7, 9-11, and 14.

8. The method according to claim 2, wherein the acceptor molecule is LNnT and the fucosyltransferase is encoded by a gene having a sequence selected from the group consisting of SEQ ID NOs: 2, 5, 11, 12, and 14.

9. The method according to claim 1, wherein the heterologous fucosyltransferase is encoded by a nucleic acid molecule, wherein the nucleic acid molecule:
   i) comprises a nucleotide sequence set forth in any one of SEQ ID NOs: 2-12 and 14-15.
   ii) comprises a nucleotide sequence having a sequence identity of at least 80% to any one of SEQ ID NOs: 2-12 and 14-15 over the entire length of the sequence;
   iii) comprises a nucleotide sequence which encodes a polypeptide having an amino acid sequence selected from any one of SEQ ID NOs: 17-26 and 28-30; or
   iv) comprises a nucleotide sequence which encodes a polypeptide having at least 80% sequence identity to any one of SEQ ID NOs: 17-26 and 28-30.

10. The method according to claim 9, wherein said genetically engineered cell is *Escherichia coli* and the nucleic acid molecule comprises a nucleotide sequence which encodes a polypeptide having at least 80% sequence identity to any one of SEQ ID NOs: 17-26, 28, and 30 that is codon-optimized for expression in *Escherichia coli* except if the nucleic acid molecule encodes the amino acid sequence of SEQ ID NO: 29.

11. The method according to claim 1, wherein said at least one genetically engineered cell is *Escherichia coli*.

12. The method according to claim 1, wherein the method further comprises recovering the fucosylated oligosaccharide.

* * * * *

```
                      SEQUENCE LISTING

<160> NUMBER OF SEQ ID NOS: 57

<210> SEQ ID NO 1
<211> LENGTH: 963
<212> TYPE: DNA
<213> ORGANISM: Helicobacter hepaticus

<400> SEQUENCE: 1
atgaaagatg acctggttat cctgcacccg gatggtggta tcgcctcgca gatcgcattt      60
gtcgcactgg gcctggcatt tgaacagaag ggtgcgaaag tgaagtatga cctgagctgg     120
tttgcggaag gcgccaaagg tttctggaac ccgtctaatg ctacgataa agtttatgac      180 attacctggg atatcagtaa ggcatttccg gctctgcata ttgaaatcgc aaacgaagaa     240
gaaatcgaac gttacaagtc taagtacctg atcgataacg accgcgttat cgattatgct     300
ccgccgctgt attgctacgg ctataaaggt cgtatctttc attacctgta tgcgccgttt     360
ttcgcccagt cattcgcacc gaaggaagct caagactcgc acacccgtt tgcagcactg      420 ctgcaggaaa ttgaaagctc tccgtcaccg tgcggtgttc atattcgtcg cggcgatctg     480
tcgcagccgc acatcgtcta cggtaacccg acgagcaatg aatatttcgc caaatctatt     540
gaactgatgt gtctgctgca cccgcagagt tccttttacc tgttcagcga tgacctggca     600
tttgtgaaag aacaaattgt tccgctgctg aaaggcaaga cctatcgcat ctgcgacgtc     660
aacaatccga gccagggcta cctggatctg tatctgctgt ctcgttgtcg caacattatc     720
ggctcacaag gttcgatggg cgaattcgcc aaagtgctga gcccgcataa cccgctgctg     780
attacgccgc gttaccgcaa tatctttaag gaagtggaaa acgttatgtg cgtcaattgg     840
ggtgaatccg tccagcaccc gccgctggtg tgtagtgcac cgccgccgct ggtgtcccaa     900
ctgaaacgta acgccccgct gaatagtcgc ctgtataaag aaaaggataa tgcatccgct     960
taa                                                                   963

<210> SEQ ID NO 2
<211> LENGTH: 1086
<212> TYPE: DNA
<213> ORGANISM: Brachyspira pilosicoli

<400> SEQUENCE: 2
atggctccga aacacctgat taacctgtat tatattgaca ttagtatcct gtacgtgaag      60
attaagcaga gagtaagat tttattaac ttcatgctgt acaacaacta cgaacatctg       120
atcaacaaga tcgtgcgtat tatcccgatt aaaaagcacc gtgataacct gcgcaatatt     180
```

```
ctgtatgaca tcgttaacag cctgtacaag atcgaataca tctctaagga actgaacaaa    240
aagcgcaaca ataacgatag tggcattgtc attatcgaat gccagggcgg tctggccgac    300
caattctgga agtacatcct gggtgaatct atcaaaaagc attacaactt caccgtgaag    360
tacgatatca cgtggttcga ctacaagcac aaggatatcg acggcaaaga tgaacgtccg    420
tttgaactga tcaaactgtg cccggatatt gacttcaaga tcgcgagcta cgatgaaatt    480 ttctttttata aggcctgttt cagtgttatc aacgaatcct acttcggtta cgacatcaac    540
aactacctgg aaaacaacaa gaacctgttt ctgtactcat acccgcgtat tctggatatc    600
aatgtctcgg acattaccaa aaacatcgat ctggacaagt atcattactc cacgctgaaa    660
gaagataatc tggtcctgta caacgaactg aagaattcag aatcggtggc cattcacatc    720
cgcctgggcg atagctacgt gatgtcttgt ttcaaagaag ttttcaacag ctcttacgaa    780
aactacgcaa actacttcat cgaatcaatc aacaagctgt cgaatgaact gaagaacccg    840
acctttttct ttttcagcga tgacattgat tgggttaaca agaacatcat caaaaagctg    900
aacaaccgta tctcttacaa agtcagttcc tgcaagaatc cgccgtacct ggatatctac    960
ctgatgagta acgcaaagca ttacatcatc tccctgggcg ttttggtga cctggctacg   1020 cgcttcaaca caacgaaaaa caagatcgtg atcaaggcgt gtaagtttca gtatgattac   1080
ctgtaa                                                               1086

<210> SEQ ID NO 3
<211> LENGTH: 861
<212> TYPE: DNA
<213> ORGANISM: Yersinia sp.

<400> SEQUENCE: 3
atgtttatga aaatctcggt cctggtccaa ggtggcctgg gtaatcaact gttccaaatc     60
gcatgggcaa actatctggt tcgtaagtat cagtataacg tcgaaattaa tctgcaactg    120
ctgtacagtc agtcccaaca tgcgtcaatt aacttttcgc agctgatcgg caaagttccg    180
ctgctgtcag tctcgaaaga aaagctgatt atgctggatg accgtctgag ctctaaaatt    240
atccgtaaga gcctgcgcat cctgggtgtt cattctattc cgaatatcct gctgcacgat    300
tatgacgcac tgaccgattt tgaacactgc aacaaaatgg ctaattatcg ttaccagttc    360
ggctactttc aattcattga agcggccatc ttttctcgtg atattttcct gagcaacatg    420
cgctctatcc atggtgaatt catcaaaaag tgtgaaagcg aattttttcga acgccattat    480 gtgggcattc acatccgtcg cggtgatttc attaaaagca ccgacccgct gcacctggca    540
acgggtattg attacatcaa aaagagtatc aaaaagttca acaatcgtaa ctttattgtg    600
ttctccgatg acatcggttg gtgccgcgat aaactgggcg aaagtgacgg tattgtttat    660
tttagtggca attccgccat tgaagatttc atcggtctga tgtgctgtaa ggactttatc    720
ctgagcggct ctaccttctc atggtgggca gctattctgt cgctgaacga aaatacgcgt    780
gtggttatcc cgaacagtaa agcgcagttt atgtccattg aagccaatac gcgcatcggt    840
tgggatttcg aagtcgtgta a                                              861

<210> SEQ ID NO 4
<211> LENGTH: 903
<212> TYPE: DNA
<213> ORGANISM: Gramella forsetii

<400> SEQUENCE: 4
atgtccaata aaaatccggt tatcgttgaa atcatgggtg gcctgggcaa tcagatgttc     60
```

```
caattcgccg tcgcaaaact gctggcagaa aagaacagca gcgtgctgct ggtcgatacg      120
aacttctaca aggaaatcag ccagaacctg aaggattttc gcgttatttc tcactgggc       180 attttcgaca tctcgtacaa aatgggcacc gaaaacggta tggtcaactt caagaacctg     240
agtttcaaga accgtgtgtc ccgcaaactg ggtctgaact atccgaagat ctttaaagaa     300
aagtcctacc gttttgatgc ggacctgttc aacaaaaaga cgccgattta tctgaaaggc     360
tactttcagt catataagta cttcattggt gttgaatcga aaatccgcca atggtttgaa     420
tttccgtacg aaaatctggg cgtcggtaac gaagaaatca gagtaagat cctggaaaag      480 acctcagtgt cggttcatat ccgtcgcggc gattacgtgg aaaacaaaaa gacgaaggaa     540
tttcacggta attgctctct ggaatattac aaaaacgcga ttacctactt tctggatatt     600
gtgaaggaat taacatcgt gttttcagc gatgacattt cttgggttcg tgatgaattt        660
aaagacctgc cgaacgaaaa ggtcttcgtg accggcaatc tgcatgaaaa cagttggaaa     720
gatatgtatc tgatgtccct gtgtgaccac aatattatcg ccaacagttc cttttcttgg     780
tgggcggcct ggctgaacaa taactctgaa aagaacgtga tcgcaccgaa aaagtggttc     840
gctgatattg accaggaaca aaaaagcctg gatctgctgc cgccgtcttg gattcgcatg     900
taa                                                                    903

<210> SEQ ID NO 5
<211> LENGTH: 1128
<212> TYPE: DNA
<213> ORGANISM: Francisella philomiragia ssp. philomiragia

<400> SEQUENCE: 5
atgaaaatta tcaaaatcca aggtggcctg ggtaaccaaa tgttccaata cgcattctac      60
aaaagcctga aaacaactg catcgattgc tacgtggata ttaagaacta cgacacctac     120
aagctgcatt atggcttcga actgaaccgt atcttcaaga acatcgatct gtcatttgca     180
cgcaaatatc acaaaaagga agttctgggt aaactgttca gtattatccc gtccaagttc     240
atcgtcaagt tcaacaagaa ctacatctta cagaaaaact ttgcgttcga taaggcctac     300
tttgaaatcg ataactgcta tctggacggc tactggcaat ccgaaaagta cttcaaaaag     360
attaccaagg atatttacga cgcttttacg ttcgaaccgc tggatagtat caacttcgaa     420
tttctgaaga acatccagga ctataatctg gtctccattc atgtgcgtcg cggtgattac     480
gttaatcatc cgctgcacgg cggtatttgt gacctggaat actacaacaa ggcaatttca     540
tttatccgtt cgaaagtggc taacgttcat tttctggtgt tcagcaatga tattctgtgg     600
tgcaaagata acctgaagct ggaccgtgtt acgtatattg atcacaatcg ctggatggat     660
agctacaaag acatgcatct gatgtctctg tgtaaacaca acattatcgc gaatagctct     720
ttttcttggt ggggcgcctg gctgaaccag aatgatgaca aaattgtcat cgcaccgtca     780
aagtggttca cgatgacaa gatcaaccaa aaggatattt gcccgaactc gtgggttcgc     840
atttaagcgg ccgcgtcgac acgcaaaaag gccatccgtc aggatggcct tctgcttaat     900
ttgatgcctg gcagtttatg gcgggcgtcc tgcccgccac cctccgggcc gttgcttcgc     960
aacgttcaaa tccgctcccg gcggatttgt cctactcagg agagcgttca ccgacaaaca    1020
acagataaaa cgaaaggccc agtctttcga ctgagccttt cgttttattt gatgcctggc    1080
agttccctac tctcgcatgg ggagaccca cactaccatc atgtatga                   1128

<210> SEQ ID NO 6
```

```
<211> LENGTH: 885
<212> TYPE: DNA
<213> ORGANISM: Pseudogulbenkiania ferrooxidans

<400> SEQUENCE: 6
atgattattg ttcgcctgat gggtggcatg ggtaaccaac tgtttcaata cgcaacggca    60
ttcgcactgt caaaacgcaa gtcggaaccg ctggtgctgg atacccgctt tttcgaccat   120
tatacgctgc acggcggtta caagctggat cattttaaca ttagcgcacg tatcctgtct   180
aaagaagaag aaagcctgta tccgaactgg caggcgaatc tgctgctgcg ctacccgatt   240
atcgatcgtg cctttaaaaa gtggcacgtt gaacgccagt tcacctatca agaccgtatt   300
taccgcatga acgtggcca ggcgctgctg ggttattggc agtcggaact gtacttccaa    360
gaataccgta aggaaattag cgcggaattt accctgaaag aacagagctc tgtcacggcg   420
cagcaaattt ccgtggccat gcaaggcggt aactcagtgg cagttcatat ccgtcgcggc   480
gattatctga gtaatccgtc cgctctgcgc acccacggca tttgcagcct gggttattac   540
aaccacgcaa tgagtctgct gaacgaacgt atcaatgatg ctcagttttta cattttcagc   600
gatgacatcg cgtgggccaa ggaaaacatt aaaatcggca agacgtccaa gaacctgatc   660
ttcatcgagg gtgaatcagt cgaaaccgat ttctggctga tgacgcagtc taaacatcac   720
attatcgcca ttcaaccttt tcgtggtgg ggtgcatggc tggctaacaa tacggacgaa    780
caactggtta tttgtccgag cccgtggttc gatgacaaaa acctgtcgga aaccgatctg   840
attccgaaga gctggattcg tctgaataaa gacctgccgg tctaa                   885

<210> SEQ ID NO 7
<211> LENGTH: 879
<212> TYPE: DNA
<213> ORGANISM: Sideroxydans lithotrophicus

<400> SEQUENCE: 7
atggttatct caaacattat cgtggcctg ggtaatcaaa tgttccaata cgcagcagca    60
cgcgccctgt ccctgaaact ggaagtgccg ctgaaactgg atatttccgg ttttaccaac   120
tatgccctgc atcagggttt tgaactggac cgtatcttcg gctgcaagat tgaaatcgcg   180
agcgaagccg atgtgcacga attctgggc tggcaaagtg cgtccggtat ccgtcgcgtg    240
gttagccgtc cgggcatgtc tattttttcgt cgcaaaggct tcgtcgtgga accgcatttt   300
tcatattgga atggcattcg caaaatcacg ggtgattgtt atctggcggg ctactggcag   360
tcggaaaagt acttcctgga tgcggccgtg gaaatccgca aagactttag tttcaagctg   420
ccgctggatt cccataacgc agaactggct gaaaaaattg accaagaaaa tgcggttagc   480
ctgcacatcc gtcgcggtga ttatgccaac aatccgctga ccgcagctac gcatggcctg   540
tgctcactgg actattaccg taaatcgatt aagcacatcg ccggtcaggt gcgcaacccg   600
tactttttcg tttttagtga tgacattgct tgggttaaag ataatctgga atcgaatttt   660
ccgtcccaat atgtggatta caaccacggt tcaatgtcgt tcaatgatat cgtctgatg    720
agcctgtgta acatcacat tatcgcaaac agctcttttt cttggtgggg cgcttggctg   780
aacccgaatc cggaaaaggt tgtcattgcg ccggaacgtt ggttcgccaa tcgcaccgat   840
gtccaggacc tgctgccgcc gggttgggtg aaactgtaa                          879

<210> SEQ ID NO 8
<211> LENGTH: 912
<212> TYPE: DNA
<213> ORGANISM: Providencia alcalifaciens
```

```
<400> SEQUENCE: 8
atgaaaatca acggtaaaga aagctcaatg aaaatcaaac aaaagaaaat tatctctcac        60
ctgatcggtg gcctgggtaa ccaactgttt cagtatgcga cgagctacgc gctggccaaa       120
gaaaacaatg ccaagattgt gatcgatgac cgtctgttca aaaagtataa actgcatggc       180
ggttaccgcc tggacaaact gaacatcatc ggcgaaaaaa ttagctctat cgataagctg       240
ctgtttccgc tgattctgtg caaactgagt cagaaggaaa acttcatctt caaatccacc       300
aaaaagttca tcctggaaaa gaaaccagc agctttaagt acctgacgtt cagtgataag        360
gaacacacca gatgctgat tggttactgg cagaacgcga tctacttcca aaagtacttc        420
tctgaactga aggaaatgtt tgttccgctg atatttcac aggaacaact ggacctgtcg        480
attcagatcc atgcacagca aagcgtggct ctgcacgttc gtcgcggcga ctatatttct       540
aacaaaaatg cactggctat gcatggtatt tgtagcatcg attactacaa aaactctatc       600
cagcacatca atgcaaaact ggaaaagccg tttttctata tttttagcaa cgacaaactg       660
tggtgcgaag aaaatctgac gccgctgttt gatggcaact tccatatcgt cgaaaacaat       720
tcacaggaaa ttgatctgtg gctgatctcg cagtgtcaac atcacattat cgcgaatagc       780
acgttttctt ggtggggtgc gtggctggcc aactcagatt cgcaaattgt catcaccccg       840
gacccgtggt tcaacaaaga aattgatatt ccgagtccgg tgctgtccca ctggctgaaa       900
ctgaaaaagt aa                                                          912

<210> SEQ ID NO 9
<211> LENGTH: 867
<212> TYPE: DNA
<213> ORGANISM: Pseudoalteromonas haloplanktis

<400> SEQUENCE: 9
atgattaagg tcaaagctat cggtggcctg ggtaaccaac tgttccaata cgcaacggcc        60
cgtgcaatcg cagaaaaacg tggtgatggc gtggttgtcg atatgagcga ctttagctct       120
tataaaaccc atccgttttg cctgaataag ttccgttgta aagcaacgta cgaaagcaaa       180
ccgaagctga tcaacaagct gctgtctaat gaaaaaattc gcaacctgct gcagaaactg       240
ggcttcatca aaaagtacta cttcgaaacc caactgccgt ttaatgaaga tgtgctgctg       300
aacaattcca tcaactatct gacgggttac ttccagtcag aaaaatattt tctgtcgatt       360
cgtgaatgcc tgctggatga actgaccctg atcgaagacc tgaatattgc ggaaacggcc       420
gttagtaagg caatcaagaa cgctaagaac tcaatctcga tccatatccg tcgcggtgat       480
tacgtctcta acgaaggcgc aaataagacc cacggtgtgt gtgatagtga ctatttcaaa       540
aaggctctga actactttc cgaacgcaaa ctgctggatg aacatacgga actgtttatc       600
ttctcagatg acattgaatg gtgccgtaac aacctgtcgt tcgattacaa gatgaacttc       660
gttgacggca gttccgaacg cccggaagtg gatatggttc tgatgagcca gtgtaaacac       720
caagtcatca gcaactctac cttctcttgg tggggtgcgt ggctgaacaa gaatgatgaa       780
aaagtggttg tcgccccgaa ggaatggttt aaaagtaccg atctggactc cacggacatc       840
gtgccgaacc aatggattaa actgtaa                                           867

<210> SEQ ID NO 10
<211> LENGTH: 876
<212> TYPE: DNA
<213> ORGANISM: Roseovarius nubinhibens
```

<400> SEQUENCE: 10

```
atgacggata cgccgccgcc gagccaagtg attacgagcc gcctgttcgg tggtgccggt    60
aaccaactgt tccaatacgc agccggtcgt gccctggcag atcgcctggg ctgcgatctg   120
atgattgacg cacgttatgt ggctggcagc cgtgatcgcg gtgactgttt tacccatttc   180
gctaaagcac gtctgcgtcg cgatgttgca ctgccgccgg caaaaagtga cggtccgctg   240
cgttacgcac tgtggcgtaa gtttggtcgt tccccgcgtt ccatcgtga acgcggcctg    300
ggtgtcgatc cggaattttt caacctgccg cgtggcacct atctgcacgg ttactggcag   360
tcagaacaat attttggtcc ggataccgac gcgctgcgtc gcgatctgac gctgaccacg   420
gctctggacg caccgaatgc agcaatggca gctcagattg atgcggcccc gtgcccggtt   480
tcgttccatg tccgtcgcgg cgattatatc gcagctggtg catacgcggc ctgtaccccg   540
gattattacc gtgcagctgc agaccacctg gcaaccacgc tgggtaaacc gctgacgtgc   600
tttattttca gtaacgatcc ggcctgggca cgcgataatc tggacctggg ccaggaccaa   660
gtcatcgtgg atctgaacga cgaagcgacc ggtcactttg atatggccct gatggcacgc   720
tgtgctcatc acgttattgc aaacagcacg ttctcttggt ggggtgcttg gctgaatccg   780
gatccggaca aactggtggt ggccccgcgt aactggtttg cgacccaggc cctgcataat   840
ccggatctga tcccggaaca atggcaccgc ctgtaa                            876
```

<210> SEQ ID NO 11
<211> LENGTH: 879
<212> TYPE: DNA
<213> ORGANISM: Thalassospira profundimaris

<400> SEQUENCE: 11

```
atggttattg tgaaactgct gggtggcctg ggtaatcaaa tgttccaata tgctacgggt    60
cgtgccgttg cttctcgcct ggatgttgaa ctgctgctgg acgttagcgc atttgctcat   120
tatgatctgc gtcgctacga actggatgac tggaacatta ccgcacgtct ggcaacgagc   180
gaagaactgg cacgttctgg cgttaccgca gcaccgccga gcttttttcga ccgtattgcg   240
cgcttcctgc gtatcgatct gccggtcaat tgctttcgcg aagcctcctt cacgtatgat   300
ccgcgtattc tggaagtcag ctctccggtg tatctggacg gttactggca gtctgaacgc   360
tactttctgg atatcgaaaa gaaactgcgt caggaattcc aactgaaggc atcaatcgac   420
gctaacaacc attcgttcaa aaagaaaatc gatggcctgg gtaaacaggc agttagtctg   480
catgtccgtc gcggcgatta tgtcaccaac ccgcaaacgg ctagttacca cggtgtgtgc   540
tccctggact attaccgcgc agctgtcgat tatatcgccg aacacgtgag cgatccgtgc   600
ttttctgtgt ttagcgatga cctggaatgg gttcagacca acctgaatat taaacaaccg   660
atcgtgctgg ttgatgcaaa cggcccggac aatggtgcgg ccgatatggc gctgatgatg   720
gcctgtcgtc atcacattat cgccaacagt tcctttttcat ggtggggctc gtggctgaac   780
ccgctgaatg ataaaattat cgtggcaccg aagaaatggt tcggtcgcgc taatcacgat   840
accacggacc tggtgccgga tagctgggtt cgtctgtaa                          879
```

<210> SEQ ID NO 12
<211> LENGTH: 879
<212> TYPE: DNA
<213> ORGANISM: Desulfovibrio alaskensis

<400> SEQUENCE: 12

```
atgaagttcg tgggtgtgtg gatcctgggt ggcctgggta atcaaatgtt ccaattcgca    60
```

```
gcagcctatg cactggcaaa acgtatgggc ggtgaactgc gtctggatct gtctggcttt      120
aaaaagtacc cgctgcgcag ttattccctg gacctgttta ccgttgacac gccgctgtgg      180
catggtctgc cgatgagcca gcgtcgcttt cgtattccga tggatgcttg gacccgtggt      240
agtcgtctgc cgctggtgcc gtccccgccg ttcgttatgg cgaaagaaaa gaactttgcc      300
ttctcaccga ttgtttatga actgcagcaa tcgtgctatc tgtacggcta ttggcagagc      360
taccgctatt ttcaagatgt cgaagatgac atccgtaccc tgttttcact gtcgcgtttc      420
gcaacgctgg aactggcacc ggtggttgca cagctgaacg aagtggaatc tgtcgccgtg      480
catctgcgtc gcggtgatta cattaccgac gcggccagta atgcagttca cggcgtctgt      540
ggtatcgatt attaccaacg tagcatgtct ctggtccgtc gctctaccac gaaaccgatc      600 tttatatct tcagtgacga accggaagtg gcaaaaaagc tgtttgctac ggaagatgac      660
gtcgtggtta tgccgtcccg tcgccaggaa gaagatctgc tgctgatgtc acgttgcaaa      720
catcacatta tcgcgaatag ctcttttctcg tggtgggcag cttggctggg caaacgcgca      780
agcggtctgt gtattgctcc gcgttactgg tttgcgcgcc cgaagctgga atccacctac      840
ctgtttgatc tgatcccgga cgaatggctg ctgctgtaa                             879

<210> SEQ ID NO 13
<211> LENGTH: 882
<212> TYPE: DNA
<213> ORGANISM: Thermosynechococcus elongates

<400> SEQUENCE: 13
atgattattg tccatctgtg tggtggcctg ggtaaccaaa tgttccaata tgcagcgggc       60
ctggcagcag ctcaccgtat cggtagcgaa gttaaatttg acacccattg gttcgatgca      120
acgtgcctgc accagggtct ggaactgcgt cgcgtgtttg gtctggaact gccggaaccg      180
agctctaaag atctgcgtaa ggttctgggc gcatgtgttc atccggctgt ccgtcgcctg      240
ctggcaggtc atttcctgca cggtctgcgt ccgaagtcac tggtcattca gccgcatttt      300
cactattgga ccggcttcga cacctgccg gacaacgtgt atctgaagg ttactggcaa      360 agcgaacgtt acttttctaa tatcgccgat attatccgtc agcaatttcg cttcgttgaa      420
ccgctggacc cgcataacgc ggccctgatg gatgaaatgc agagcggcgt tagtgtctcc      480
ctgcatattc gtcgcggtga ctatttcaac aatccgcaaa tgcgtcgcgt ccacggtgtg      540
gatctgtctg aatattaccc ggcagctgtg gcaaccatga tcgaaaaaac gaacgctgaa      600
cgcttttacg tgttctcaga tgacccgcag tgggttctgg aacatctgaa gctgccggtc      660
tcgtataccg tggttgacca caatcgtggc gcggccagtt accgcgatat gcaactgatg      720
tccgcgtgcc gtcatcacat tatcgccaac tcaacgtttt cgtggtgggg tgcatggctg      780
aatccgcgtc cggataaagt cgtgattgcc ccgcgccatt ggtttaatgt ggatgttttc      840
gacacgcgcg atctgtattg tccgggctgg atcgtgctgt aa                        882

<210> SEQ ID NO 14
<211> LENGTH: 996
<212> TYPE: DNA
<213> ORGANISM: Bacteroides fragilis

<400> SEQUENCE: 14
atgtgtgatt gcctgtctat tatcctgctg gtgaaaatga aaagatcta cctgaaattc        60 gtggacttct gggacggctt tgataccatc agtaacttta ttgtggatgc actgtccatc      120
```

-continued

```
cagtatgaag tggttctgtc aaatgaaccg gactacctgt tttatagctg cttcggcacc      180
tctcatctgg aatacgattg tatcaaaatc atgttcatcg gtgaaaacat cgtgccggat      240
ttcaatgttt gcgactatgc gattggcttt aactacatcg atttcggtga ccgttatctg      300
cgcctgccgc tgtatgccat ttacgatggc ttctccaacc tgcaaaacaa gaaaattgat      360
gtcaacaaag cactggaccg caaattctgt tcaattgtcg gtcgaacaa taaatgggct       420 gatccgatcc gtgaaacgtt tttcaaactg ctgagctctt acaaaaaagt tgattctggc      480
ggtcgcgcat ggaacaatat tggcggtccg gtcgataaca aactggactt catctctcag      540
tacaaattca acatcgcttt cgaaaacagt cgtgttctgg gttacaccac ggaaaaaatt      600
atggaaccga tgcaagtcaa cagcatcccg gtgtattggg gcaacccgct ggttggcaaa      660 gatttttaacg ttgactcgtt cgtcaatgcc catgattttg acagcctgga acgcctggtt      720
gaatatatta tcgaactgga tagttccaaa gacaaatacc tggaaatgct ggaaaaaccg      780
tggctgctgg ataaaaccta tctggactgg aaacagctgc tgctgaactt catcaacaac      840
atcatgatga aaagttacaa agatgcgaaa tacctggtta actacggcca cgccggtaaa      900
taccgtaatg aacaacgctt ctggggccgt tgcgaacgta aattcaaact gcaacgcatt      960
atcgaatact actcccaact gtttgatcgt aaataa                               996
```

<210> SEQ ID NO 15
<211> LENGTH: 550
<212> TYPE: DNA
<213> ORGANISM: Escherichia coli

<400> SEQUENCE: 15

```
atgagcatta ttcgtctgca gggtggtctg ggtaatcagc tgtttcagtt tagctttggt       60
tatgcgctga gcaaaattaa tggtacaccg ctgtatttcg acattagcca ttatgccgaa      120
aacgatgatc atggtggtta cgtctgaat aatctgcaga ttccggaaga atatctgcag       180
tattataccc cgaaaattaa taatatttat aaactgctgg tgcgtggcag ccgtctgtat      240
ccggatattt ttctgtttct gggcttttgc aacgaatttc atgcctatgg ctacgatttt      300
gaatatattg cccagaaatg gaaaagcaaa aaatacattg gctactgca gagcgaacac      360 tttttttcata acatattctg gacctgaaa gaatttttta ttccgaaaaa tgtgagcgaa      420
caggcaaatc tgctggcagc aaaaaattctg gaaagccaga gcagcctgag cattcatatt      480
cgtcgtggcg attatattaa aaacaaaacc gcaaccctga cacatggtgt tgtagcctg      540 gaatattata                                                             550
```

<210> SEQ ID NO 16
<211> LENGTH: 320
<212> TYPE: PRT
<213> ORGANISM: Helicobacter hepaticus

<400> SEQUENCE: 16

Met Lys Asp Asp Leu Val Ile Leu His Pro Asp Gly Gly Ile Ala Ser
1               5                   10                  15

Gln Ile Ala Phe Val Ala Leu Gly Leu Ala Phe Glu Gln Lys Gly Ala
            20                  25                  30

Lys Val Lys Tyr Asp Leu Ser Trp Phe Ala Glu Gly Ala Lys Gly Phe
        35                  40                  45

Trp Asn Pro Ser Asn Gly Tyr Asp Lys Val Tyr Asp Ile Thr Trp Asp
    50                  55                  60

Ile Ser Lys Ala Phe Pro Ala Leu His Ile Glu Ile Ala Asn Glu Glu

```
                65                  70                  75                  80
        Glu Ile Glu Arg Tyr Lys Ser Lys Tyr Leu Ile Asp Asn Asp Arg Val
                            85                  90                  95

Ile Asp Tyr Ala Pro Pro Leu Tyr Cys Tyr Gly Tyr Lys Gly Arg Ile
                        100                 105                 110

Phe His Tyr Leu Tyr Ala Pro Phe Ala Gln Ser Phe Ala Pro Lys
                    115                 120                 125

Glu Ala Gln Asp Ser His Thr Pro Phe Ala Leu Leu Gln Glu Ile
                130                 135                 140

Glu Ser Ser Pro Ser Pro Cys Gly Val His Ile Arg Arg Gly Asp Leu
        145                 150                 155                 160

Ser Gln Pro His Ile Val Tyr Gly Asn Pro Thr Ser Asn Glu Tyr Phe
                        165                 170                 175

Ala Lys Ser Ile Glu Leu Met Cys Leu Leu His Pro Gln Ser Ser Phe
                    180                 185                 190

Tyr Leu Phe Ser Asp Asp Leu Ala Phe Val Lys Glu Gln Ile Val Pro
                195                 200                 205

Leu Leu Lys Gly Lys Thr Tyr Arg Ile Cys Asp Val Asn Asn Pro Ser
        210                 215                 220

Gln Gly Tyr Leu Asp Leu Tyr Leu Leu Ser Arg Cys Arg Asn Ile Ile
        225                 230                 235                 240

Gly Ser Gln Gly Ser Met Gly Glu Phe Ala Lys Val Leu Ser Pro His
                        245                 250                 255

Asn Pro Leu Leu Ile Thr Pro Arg Tyr Arg Asn Ile Phe Lys Glu Val
                    260                 265                 270

Glu Asn Val Met Cys Val Asn Trp Gly Glu Ser Val Gln His Pro Pro
                275                 280                 285

Leu Val Cys Ser Ala Pro Pro Leu Val Ser Gln Leu Lys Arg Asn
        290                 295                 300

Ala Pro Leu Asn Ser Arg Leu Tyr Lys Glu Lys Asp Asn Ala Ser Ala
        305                 310                 315                 320

<210> SEQ ID NO 17
<211> LENGTH: 361
<212> TYPE: PRT
<213> ORGANISM: Brachyspira pilosicoli

<400> SEQUENCE: 17

Met Ala Pro Lys His Leu Ile Asn Leu Tyr Tyr Ile Asp Ile Ser Ile
        1               5                   10                  15

Leu Tyr Val Lys Ile Lys Gln Lys Ser Lys Ile Phe Ile Asn Phe Met
                        20                  25                  30

Leu Tyr Asn Asn Tyr Glu His Leu Ile Asn Lys Ile Val Arg Ile Ile
                    35                  40                  45

Pro Ile Lys Lys His Arg Asp Asn Leu Arg Asn Ile Leu Tyr Asp Ile
                50                  55                  60

Val Asn Ser Leu Tyr Lys Ile Glu Tyr Ile Ser Lys Glu Leu Asn Lys
        65                  70                  75                  80

Lys Arg Asn Asn Asn Asp Ser Gly Ile Val Ile Glu Cys Gln Gly
                        85                  90                  95

Gly Leu Ala Asp Gln Phe Trp Lys Tyr Ile Leu Gly Glu Ser Ile Lys
                    100                 105                 110

Lys His Tyr Asn Phe Thr Val Lys Tyr Asp Ile Thr Trp Phe Asp Tyr
                115                 120                 125
```

```
Lys His Lys Asp Ile Asp Gly Lys Asp Glu Arg Pro Phe Glu Leu Ile
    130                 135                 140

Lys Leu Cys Pro Asp Ile Asp Phe Lys Ile Ala Ser Tyr Asp Glu Ile
145                 150                 155                 160

Phe Phe Tyr Lys Ala Cys Phe Ser Val Ile Asn Glu Ser Tyr Phe Gly
                165                 170                 175

Tyr Asp Ile Asn Asn Tyr Leu Glu Asn Asn Lys Asn Leu Phe Leu Tyr
            180                 185                 190

Ser Tyr Pro Arg Ile Leu Asp Ile Asn Val Ser Asp Ile Thr Lys Asn
                195                 200                 205

Ile Asp Leu Asp Lys Tyr His Tyr Ser Thr Leu Lys Glu Asp Asn Leu
210                 215                 220

Val Leu Tyr Asn Glu Leu Lys Asn Ser Glu Ser Val Ala Ile His Ile
225                 230                 235                 240

Arg Leu Gly Asp Ser Tyr Val Met Ser Cys Phe Lys Glu Val Phe Asn
                245                 250                 255

Ser Ser Tyr Glu Asn Tyr Ala Asn Tyr Phe Ile Glu Ser Ile Asn Lys
                260                 265                 270

Leu Ser Asn Glu Leu Lys Asn Pro Thr Phe Phe Phe Ser Asp Asp
275                 280                 285

Ile Asp Trp Val Asn Lys Asn Ile Ile Lys Lys Leu Asn Asn Arg Ile
290                 295                 300

Ser Tyr Lys Val Ser Ser Cys Lys Asn Pro Pro Tyr Leu Asp Ile Tyr
305                 310                 315                 320

Leu Met Ser Asn Ala Lys His Tyr Ile Ile Ser Leu Gly Gly Phe Gly
                325                 330                 335

Asp Leu Ala Thr Arg Phe Asn Asn Asn Glu Asn Lys Ile Val Ile Lys
                340                 345                 350

Ala Cys Lys Phe Gln Tyr Asp Tyr Leu
                355                 360

<210> SEQ ID NO 18
<211> LENGTH: 286
<212> TYPE: PRT
<213> ORGANISM: Yersinia sp.

<400> SEQUENCE: 18

Met Phe Met Lys Ile Ser Val Leu Val Gln Gly Gly Leu Gly Asn Gln
1               5                   10                  15

Leu Phe Gln Ile Ala Trp Ala Asn Tyr Leu Val Arg Lys Tyr Gln Tyr
                20                  25                  30

Asn Val Glu Ile Asn Leu Gln Leu Leu Tyr Ser Gln Ser Gln His Ala
            35                  40                  45

Ser Ile Asn Phe Ser Gln Leu Ile Gly Lys Val Pro Leu Leu Ser Val
    50                  55                  60

Ser Lys Glu Lys Leu Ile Met Leu Asp Asp Arg Leu Ser Ser Lys Ile
65                  70                  75                  80

Ile Arg Lys Ser Leu Arg Ile Leu Gly Val His Ser Ile Pro Asn Ile
                85                  90                  95

Leu Leu His Asp Tyr Asp Ala Leu Thr Asp Phe Glu His Cys Asn Lys
                100                 105                 110

Met Ala Asn Tyr Arg Tyr Gln Phe Gly Tyr Phe Gln Phe Ile Glu Ala
            115                 120                 125

Ala Ile Phe Ser Arg Asp Ile Phe Leu Ser Asn Met Arg Ser Ile His
    130                 135                 140
```

```
Gly Glu Phe Ile Lys Lys Cys Glu Ser Glu Phe Glu Arg His Tyr
145                 150                 155                 160

Val Gly Ile His Ile Arg Arg Gly Asp Phe Ile Lys Ser Thr Asp Pro
                165                 170                 175

Leu His Leu Ala Thr Gly Ile Asp Tyr Ile Lys Lys Ser Ile Lys Lys
            180                 185                 190

Phe Asn Asn Arg Asn Phe Ile Val Phe Ser Asp Asp Ile Gly Trp Cys
                195                 200                 205

Arg Asp Lys Leu Gly Glu Ser Asp Gly Ile Val Tyr Phe Ser Gly Asn
            210                 215                 220

Ser Ala Ile Glu Asp Phe Ile Gly Leu Met Cys Cys Lys Asp Phe Ile
225                 230                 235                 240

Leu Ser Gly Ser Thr Phe Ser Trp Trp Ala Ala Ile Leu Ser Leu Asn
                245                 250                 255

Glu Asn Thr Arg Val Val Ile Pro Asn Ser Lys Ala Gln Phe Met Ser
                260                 265                 270

Ile Glu Ala Asn Thr Arg Ile Gly Trp Asp Phe Glu Val Val
                275                 280                 285

<210> SEQ ID NO 19
<211> LENGTH: 300
<212> TYPE: PRT
<213> ORGANISM: Gramella forsetii

<400> SEQUENCE: 19

Met Ser Asn Lys Asn Pro Val Ile Val Glu Ile Met Gly Gly Leu Gly
1               5                   10                  15

Asn Gln Met Phe Gln Phe Ala Val Ala Lys Leu Leu Ala Glu Lys Asn
                20                  25                  30

Ser Ser Val Leu Leu Val Asp Thr Asn Phe Tyr Lys Glu Ile Ser Gln
            35                  40                  45

Asn Leu Lys Asp Phe Pro Arg Tyr Phe Ser Leu Gly Ile Phe Asp Ile
50                  55                  60

Ser Tyr Lys Met Gly Thr Glu Asn Gly Met Val Asn Phe Lys Asn Leu
65                  70                  75                  80

Ser Phe Lys Asn Arg Val Ser Arg Lys Leu Gly Leu Asn Tyr Pro Lys
                85                  90                  95

Ile Phe Lys Glu Lys Ser Tyr Arg Phe Asp Ala Asp Leu Phe Asn Lys
                100                 105                 110

Lys Thr Pro Ile Tyr Leu Lys Gly Tyr Phe Gln Ser Tyr Lys Tyr Phe
            115                 120                 125

Ile Gly Val Glu Ser Lys Ile Arg Gln Trp Phe Glu Phe Pro Tyr Glu
130                 135                 140

Asn Leu Gly Val Gly Asn Glu Glu Ile Lys Ser Lys Ile Leu Glu Lys
145                 150                 155                 160

Thr Ser Val Ser Val His Ile Arg Arg Gly Asp Tyr Val Glu Asn Lys
                165                 170                 175

Lys Thr Lys Glu Phe His Gly Asn Cys Ser Leu Glu Tyr Tyr Lys Asn
            180                 185                 190

Ala Ile Thr Tyr Phe Leu Asp Ile Val Lys Glu Phe Asn Ile Val Phe
            195                 200                 205

Phe Ser Asp Asp Ile Ser Trp Val Arg Asp Glu Phe Lys Asp Leu Pro
210                 215                 220

Asn Glu Lys Val Phe Val Thr Gly Asn Leu His Glu Asn Ser Trp Lys
```

```
                225                 230                 235                 240

Asp Met Tyr Leu Met Ser Leu Cys Asp His Asn Ile Ile Ala Asn Ser
                245                 250                 255

Ser Phe Ser Trp Trp Ala Ala Trp Leu Asn Asn Asn Ser Glu Lys Asn
                260                 265                 270

Val Ile Ala Pro Lys Lys Trp Phe Ala Asp Ile Asp Gln Glu Gln Lys
                275                 280                 285

Ser Leu Asp Leu Leu Pro Pro Ser Trp Ile Arg Met
                290                 295                 300

<210> SEQ ID NO 20
<211> LENGTH: 281
<212> TYPE: PRT
<213> ORGANISM: Francisella philomiragia ssp. philomiragia

<400> SEQUENCE: 20

Met Lys Ile Ile Lys Ile Gln Gly Gly Leu Gly Asn Gln Met Phe Gln
1               5                   10                  15

Tyr Ala Phe Tyr Lys Ser Leu Lys Asn Asn Cys Ile Asp Cys Tyr Val
                20                  25                  30

Asp Ile Lys Asn Tyr Asp Thr Tyr Lys Leu His Tyr Gly Phe Glu Leu
            35                  40                  45

Asn Arg Ile Phe Lys Asn Ile Asp Leu Ser Phe Ala Arg Lys Tyr His
        50                  55                  60

Lys Lys Glu Val Leu Gly Lys Leu Phe Ser Ile Ile Pro Ser Lys Phe
65                  70                  75                  80

Ile Val Lys Phe Asn Lys Asn Tyr Ile Leu Gln Lys Asn Phe Ala Phe
                85                  90                  95

Asp Lys Ala Tyr Phe Glu Ile Asp Asn Cys Tyr Leu Asp Gly Tyr Trp
                100                 105                 110

Gln Ser Glu Lys Tyr Phe Lys Lys Ile Thr Lys Asp Ile Tyr Asp Ala
            115                 120                 125

Phe Thr Phe Glu Pro Leu Asp Ser Ile Asn Phe Glu Phe Leu Lys Asn
        130                 135                 140

Ile Gln Asp Tyr Asn Leu Val Ser Ile His Val Arg Arg Gly Asp Tyr
145                 150                 155                 160

Val Asn His Pro Leu His Gly Gly Ile Cys Asp Leu Glu Tyr Tyr Asn
                165                 170                 175

Lys Ala Ile Ser Phe Ile Arg Ser Lys Val Ala Asn Val His Phe Leu
                180                 185                 190

Val Phe Ser Asn Asp Ile Leu Trp Cys Lys Asp Asn Leu Lys Leu Asp
            195                 200                 205

Arg Val Thr Tyr Ile Asp His Asn Arg Trp Met Asp Ser Tyr Lys Asp
        210                 215                 220

Met His Leu Met Ser Leu Cys Lys His Asn Ile Ile Ala Asn Ser Ser
225                 230                 235                 240

Phe Ser Trp Trp Gly Ala Trp Leu Asn Gln Asn Asp Asp Lys Ile Val
                245                 250                 255

Ile Ala Pro Ser Lys Trp Phe Asn Asp Asp Lys Ile Asn Gln Lys Asp
                260                 265                 270

Ile Cys Pro Asn Ser Trp Val Arg Ile
            275                 280

<210> SEQ ID NO 21
<211> LENGTH: 294
```

```
<212> TYPE: PRT
<213> ORGANISM: Pseudogulbenkiania ferrooxidans

<400> SEQUENCE: 21

Met Ile Ile Val Arg Leu Met Gly Gly Met Gly Asn Gln Leu Phe Gln
1               5                   10                  15

Tyr Ala Thr Ala Phe Ala Leu Ser Lys Arg Lys Ser Glu Pro Leu Val
                20                  25                  30

Leu Asp Thr Arg Phe Phe Asp His Tyr Thr Leu His Gly Gly Tyr Lys
            35                  40                  45

Leu Asp His Phe Asn Ile Ser Ala Arg Ile Leu Ser Lys Glu Glu Glu
        50                  55                  60

Ser Leu Tyr Pro Asn Trp Gln Ala Asn Leu Leu Leu Arg Tyr Pro Ile
65                  70                  75                  80

Ile Asp Arg Ala Phe Lys Lys Trp His Val Glu Arg Gln Phe Thr Tyr
                85                  90                  95

Gln Asp Arg Ile Tyr Arg Met Lys Arg Gly Gln Ala Leu Leu Gly Tyr
            100                 105                 110

Trp Gln Ser Glu Leu Tyr Phe Gln Glu Tyr Arg Lys Glu Ile Ser Ala
        115                 120                 125

Glu Phe Thr Leu Lys Glu Gln Ser Ser Val Thr Ala Gln Gln Ile Ser
130                 135                 140

Val Ala Met Gln Gly Gly Asn Ser Val Ala Val His Ile Arg Arg Gly
145                 150                 155                 160

Asp Tyr Leu Ser Asn Pro Ser Ala Leu Arg Thr His Gly Ile Cys Ser
                165                 170                 175

Leu Gly Tyr Tyr Asn His Ala Met Ser Leu Leu Asn Glu Arg Ile Asn
            180                 185                 190

Asp Ala Gln Phe Tyr Ile Phe Ser Asp Ile Ala Trp Ala Lys Glu
        195                 200                 205

Asn Ile Lys Ile Gly Lys Thr Ser Lys Asn Leu Ile Phe Ile Glu Gly
210                 215                 220

Glu Ser Val Glu Thr Asp Phe Trp Leu Met Thr Gln Ser Lys His His
225                 230                 235                 240

Ile Ile Ala Asn Ser Thr Phe Ser Trp Trp Gly Ala Trp Leu Ala Asn
                245                 250                 255

Asn Thr Asp Glu Gln Leu Val Ile Cys Pro Ser Pro Trp Phe Asp Asp
            260                 265                 270

Lys Asn Leu Ser Glu Thr Asp Leu Ile Pro Lys Ser Trp Ile Arg Leu
        275                 280                 285

Asn Lys Asp Leu Pro Val
    290

<210> SEQ ID NO 22
<211> LENGTH: 292
<212> TYPE: PRT
<213> ORGANISM: Sideroxydans lithotrophicus

<400> SEQUENCE: 22

Met Val Ile Ser Asn Ile Ile Gly Gly Leu Gly Asn Gln Met Phe Gln
1               5                   10                  15

Tyr Ala Ala Ala Arg Ala Leu Ser Leu Lys Leu Glu Val Pro Leu Lys
                20                  25                  30

Leu Asp Ile Ser Gly Phe Thr Asn Tyr Ala Leu His Gln Gly Phe Glu
            35                  40                  45
```

Leu Asp Arg Ile Phe Gly Cys Lys Ile Glu Ile Ala Ser Glu Ala Asp
            50                  55                  60

Val His Glu Ile Leu Gly Trp Gln Ser Ala Ser Gly Ile Arg Arg Val
65                  70                  75                  80

Val Ser Arg Pro Gly Met Ser Ile Phe Arg Arg Lys Gly Phe Val Val
                    85                  90                  95

Glu Pro His Phe Ser Tyr Trp Asn Gly Ile Arg Lys Ile Thr Gly Asp
                100                 105                 110

Cys Tyr Leu Ala Gly Tyr Trp Gln Ser Glu Lys Tyr Phe Leu Asp Ala
            115                 120                 125

Ala Val Glu Ile Arg Lys Asp Phe Ser Phe Lys Leu Pro Leu Asp Ser
130                 135                 140

His Asn Ala Glu Leu Ala Glu Lys Ile Asp Gln Glu Asn Ala Val Ser
145                 150                 155                 160

Leu His Ile Arg Arg Gly Asp Tyr Ala Asn Asn Pro Leu Thr Ala Ala
                165                 170                 175

Thr His Gly Leu Cys Ser Leu Asp Tyr Tyr Arg Lys Ser Ile Lys His
                180                 185                 190

Ile Ala Gly Gln Val Arg Asn Pro Tyr Phe Phe Val Phe Ser Asp Asp
            195                 200                 205

Ile Ala Trp Val Lys Asp Asn Leu Glu Ile Glu Phe Pro Ser Gln Tyr
210                 215                 220

Val Asp Tyr Asn His Gly Ser Met Ser Phe Asn Asp Met Arg Leu Met
225                 230                 235                 240

Ser Leu Cys Lys His His Ile Ile Ala Asn Ser Ser Phe Ser Trp Trp
                245                 250                 255

Gly Ala Trp Leu Asn Pro Asn Pro Glu Lys Val Val Ile Ala Pro Glu
            260                 265                 270

Arg Trp Phe Ala Asn Arg Thr Asp Val Gln Asp Leu Leu Pro Pro Gly
                275                 280                 285

Trp Val Lys Leu
        290

<210> SEQ ID NO 23
<211> LENGTH: 303
<212> TYPE: PRT
<213> ORGANISM: Providencia alcalifaciens

<400> SEQUENCE: 23

Met Lys Ile Asn Gly Lys Glu Ser Ser Met Lys Ile Lys Gln Lys Lys
1               5                   10                  15

Ile Ile Ser His Leu Ile Gly Gly Leu Gly Asn Gln Leu Phe Gln Tyr
            20                  25                  30

Ala Thr Ser Tyr Ala Leu Ala Lys Glu Asn Asn Ala Lys Ile Val Ile
            35                  40                  45

Asp Asp Arg Leu Phe Lys Lys Tyr Lys Leu His Gly Gly Tyr Arg Leu
            50                  55                  60

Asp Lys Leu Asn Ile Ile Gly Glu Lys Ile Ser Ser Ile Asp Lys Leu
65                  70                  75                  80

Leu Phe Pro Leu Ile Leu Cys Lys Leu Ser Gln Lys Glu Asn Phe Ile
                85                  90                  95

Phe Lys Ser Thr Lys Lys Phe Ile Leu Glu Lys Thr Ser Ser Phe
                100                 105                 110

Lys Tyr Leu Thr Phe Ser Asp Lys Glu His Thr Lys Met Leu Ile Gly
            115                 120                 125

Tyr Trp Gln Asn Ala Ile Tyr Phe Gln Lys Tyr Phe Ser Glu Leu Lys
130                 135                 140

Glu Met Phe Val Pro Leu Asp Ile Ser Gln Glu Gln Leu Asp Leu Ser
145                 150                 155                 160

Ile Gln Ile His Ala Gln Gln Ser Val Ala Leu His Val Arg Arg Gly
                165                 170                 175

Asp Tyr Ile Ser Asn Lys Asn Ala Leu Ala Met His Gly Ile Cys Ser
                180                 185                 190

Ile Asp Tyr Tyr Lys Asn Ser Ile Gln His Ile Asn Ala Lys Leu Glu
            195                 200                 205

Lys Pro Phe Phe Tyr Ile Phe Ser Asn Asp Lys Leu Trp Cys Glu Glu
        210                 215                 220

Asn Leu Thr Pro Leu Phe Asp Gly Asn Phe His Ile Val Glu Asn Asn
225                 230                 235                 240

Ser Gln Glu Ile Asp Leu Trp Leu Ile Ser Gln Cys Gln His His Ile
                245                 250                 255

Ile Ala Asn Ser Thr Phe Ser Trp Trp Gly Ala Trp Leu Ala Asn Ser
                260                 265                 270

Asp Ser Gln Ile Val Ile Thr Pro Asp Pro Trp Phe Asn Lys Glu Ile
            275                 280                 285

Asp Ile Pro Ser Pro Val Leu Ser His Trp Leu Lys Leu Lys
        290                 295                 300

<210> SEQ ID NO 24
<211> LENGTH: 288
<212> TYPE: PRT
<213> ORGANISM: Pseudoalteromonas haloplanktis

<400> SEQUENCE: 24

Met Ile Lys Val Lys Ala Ile Gly Gly Leu Gly Asn Gln Leu Phe Gln
1               5                   10                  15

Tyr Ala Thr Ala Arg Ala Ile Ala Glu Lys Arg Gly Asp Gly Val Val
                20                  25                  30

Val Asp Met Ser Asp Phe Ser Ser Tyr Lys Thr His Pro Phe Cys Leu
            35                  40                  45

Asn Lys Phe Arg Cys Lys Ala Thr Tyr Glu Ser Lys Pro Lys Leu Ile
        50                  55                  60

Asn Lys Leu Leu Ser Asn Glu Lys Ile Arg Asn Leu Leu Gln Lys Leu
65                  70                  75                  80

Gly Phe Ile Lys Lys Tyr Tyr Phe Glu Thr Gln Leu Pro Phe Asn Glu
                85                  90                  95

Asp Val Leu Leu Asn Asn Ser Ile Asn Tyr Leu Thr Gly Tyr Phe Gln
            100                 105                 110

Ser Glu Lys Tyr Phe Leu Ser Ile Arg Glu Cys Leu Leu Asp Glu Leu
        115                 120                 125

Thr Leu Ile Glu Asp Leu Asn Ile Ala Glu Thr Ala Val Ser Lys Ala
    130                 135                 140

Ile Lys Asn Ala Lys Asn Ser Ile Ser Ile His Ile Arg Arg Gly Asp
145                 150                 155                 160

Tyr Val Ser Asn Glu Gly Ala Asn Lys Thr His Gly Val Cys Asp Ser
                165                 170                 175

Asp Tyr Phe Lys Lys Ala Leu Asn Tyr Phe Ser Glu Arg Lys Leu Leu
            180                 185                 190

Asp Glu His Thr Glu Leu Phe Ile Phe Ser Asp Asp Ile Glu Trp Cys

```
                195                 200                 205
Arg Asn Asn Leu Ser Phe Asp Tyr Lys Met Asn Phe Val Asp Gly Ser
            210                 215                 220
Ser Glu Arg Pro Glu Val Asp Met Val Leu Met Ser Gln Cys Lys His
225                 230                 235                 240
Gln Val Ile Ser Asn Ser Thr Phe Ser Trp Trp Gly Ala Trp Leu Asn
                245                 250                 255
Lys Asn Asp Glu Lys Val Val Ala Pro Lys Glu Trp Phe Lys Ser
            260                 265                 270
Thr Asp Leu Asp Ser Thr Asp Ile Val Pro Asn Gln Trp Ile Lys Leu
            275                 280                 285
```

<210> SEQ ID NO 25
<211> LENGTH: 291
<212> TYPE: PRT
<213> ORGANISM: Roseovarius nubinhibens

<400> SEQUENCE: 25

```
Met Thr Asp Thr Pro Pro Ser Gln Val Ile Thr Ser Arg Leu Phe
1               5                   10                  15
Gly Gly Ala Gly Asn Gln Leu Phe Gln Tyr Ala Ala Gly Arg Ala Leu
            20                  25                  30
Ala Asp Arg Leu Gly Cys Asp Leu Met Ile Asp Ala Arg Tyr Val Ala
            35                  40                  45
Gly Ser Arg Asp Arg Gly Asp Cys Phe Thr His Phe Ala Lys Ala Arg
        50                  55                  60
Leu Arg Arg Asp Val Ala Leu Pro Pro Ala Lys Ser Asp Gly Pro Leu
65                  70                  75                  80
Arg Tyr Ala Leu Trp Arg Lys Phe Gly Arg Ser Pro Arg Phe His Arg
                85                  90                  95
Glu Arg Gly Leu Gly Val Asp Pro Glu Phe Phe Asn Leu Pro Arg Gly
            100                 105                 110
Thr Tyr Leu His Gly Tyr Trp Gln Ser Glu Gln Tyr Phe Gly Pro Asp
            115                 120                 125
Thr Asp Ala Leu Arg Arg Asp Leu Thr Leu Thr Thr Ala Leu Asp Ala
        130                 135                 140
Pro Asn Ala Ala Met Ala Ala Gln Ile Asp Ala Ala Pro Cys Pro Val
145                 150                 155                 160
Ser Phe His Val Arg Arg Gly Asp Tyr Ile Ala Gly Ala Tyr Ala
                165                 170                 175
Ala Cys Thr Pro Asp Tyr Tyr Arg Ala Ala Asp His Leu Ala Thr
            180                 185                 190
Thr Leu Gly Lys Pro Leu Thr Cys Phe Ile Phe Ser Asn Asp Pro Ala
            195                 200                 205
Trp Ala Arg Asp Asn Leu Asp Leu Gly Gln Asp Gln Val Ile Val Asp
            210                 215                 220
Leu Asn Asp Glu Ala Thr Gly His Phe Asp Met Ala Leu Met Ala Arg
225                 230                 235                 240
Cys Ala His His Val Ile Ala Asn Ser Thr Phe Ser Trp Trp Gly Ala
                245                 250                 255
Trp Leu Asn Pro Asp Pro Asp Lys Leu Val Val Ala Pro Arg Asn Trp
            260                 265                 270
Phe Ala Thr Gln Ala Leu His Asn Pro Asp Leu Ile Pro Glu Gln Trp
            275                 280                 285
```

His Arg Leu
    290

<210> SEQ ID NO 26
<211> LENGTH: 292
<212> TYPE: PRT
<213> ORGANISM: Desulfovibrio alaskensis

<400> SEQUENCE: 26

Met Lys Phe Val Gly Val Trp Ile Leu Gly Gly Leu Gly Asn Gln Met
1               5                   10                  15

Phe Gln Phe Ala Ala Ala Tyr Ala Leu Ala Lys Arg Met Gly Gly Glu
                20                  25                  30

Leu Arg Leu Asp Leu Ser Gly Phe Lys Lys Tyr Pro Leu Arg Ser Tyr
            35                  40                  45

Ser Leu Asp Leu Phe Thr Val Asp Thr Pro Leu Trp His Gly Leu Pro
        50                  55                  60

Met Ser Gln Arg Arg Phe Arg Ile Pro Met Asp Ala Trp Thr Arg Gly
65                  70                  75                  80

Ser Arg Leu Pro Leu Val Pro Ser Pro Pro Phe Val Met Ala Lys Glu
                85                  90                  95

Lys Asn Phe Ala Phe Ser Pro Ile Val Tyr Glu Leu Gln Gln Ser Cys
            100                 105                 110

Tyr Leu Tyr Gly Tyr Trp Gln Ser Tyr Arg Tyr Phe Gln Asp Val Glu
        115                 120                 125

Asp Asp Ile Arg Thr Leu Phe Ser Leu Ser Arg Phe Ala Thr Leu Glu
    130                 135                 140

Leu Ala Pro Val Val Ala Gln Leu Asn Glu Val Glu Ser Val Ala Val
145                 150                 155                 160

His Leu Arg Arg Gly Asp Tyr Ile Thr Asp Ala Ala Ser Asn Ala Val
                165                 170                 175

His Gly Val Cys Gly Ile Asp Tyr Tyr Gln Arg Ser Met Ser Leu Val
            180                 185                 190

Arg Arg Ser Thr Thr Lys Pro Ile Phe Tyr Ile Phe Ser Asp Glu Pro
        195                 200                 205

Glu Val Ala Lys Lys Leu Phe Ala Thr Glu Asp Asp Val Val Val Met
    210                 215                 220

Pro Ser Arg Arg Gln Glu Glu Asp Leu Leu Leu Met Ser Arg Cys Lys
225                 230                 235                 240

His His Ile Ile Ala Asn Ser Ser Phe Ser Trp Trp Ala Ala Trp Leu
                245                 250                 255

Gly Lys Arg Ala Ser Gly Leu Cys Ile Ala Pro Arg Tyr Trp Phe Ala
            260                 265                 270

Arg Pro Lys Leu Glu Ser Thr Tyr Leu Phe Asp Leu Ile Pro Asp Glu
        275                 280                 285

Trp Leu Leu Leu
    290

<210> SEQ ID NO 27
<211> LENGTH: 293
<212> TYPE: PRT
<213> ORGANISM: Thermosynechococcus elongates

<400> SEQUENCE: 27

Met Ile Ile Val His Leu Cys Gly Gly Leu Gly Asn Gln Met Phe Gln
1               5                   10                  15

```
Tyr Ala Ala Gly Leu Ala Ala Ala His Arg Ile Gly Ser Glu Val Lys
             20                  25                  30

Phe Asp Thr His Trp Phe Asp Ala Thr Cys Leu His Gln Gly Leu Glu
         35                  40                  45

Leu Arg Arg Val Phe Gly Leu Glu Leu Pro Glu Pro Ser Ser Lys Asp
 50                  55                  60

Leu Arg Lys Val Leu Gly Ala Cys Val His Pro Ala Val Arg Arg Leu
 65                  70                  75                  80

Leu Ala Gly His Phe Leu His Gly Leu Arg Pro Lys Ser Leu Val Ile
             85                  90                  95

Gln Pro His Phe His Tyr Trp Thr Gly Phe Glu His Leu Pro Asp Asn
            100                 105                 110

Val Tyr Leu Glu Gly Tyr Trp Gln Ser Glu Arg Tyr Phe Ser Asn Ile
            115                 120                 125

Ala Asp Ile Ile Arg Gln Gln Phe Arg Phe Val Glu Pro Leu Asp Pro
        130                 135                 140

His Asn Ala Ala Leu Met Asp Glu Met Gln Ser Gly Val Ser Val Ser
145                 150                 155                 160

Leu His Ile Arg Arg Gly Asp Tyr Phe Asn Asn Pro Gln Met Arg Arg
                165                 170                 175

Val His Gly Val Asp Leu Ser Glu Tyr Tyr Pro Ala Ala Val Ala Thr
            180                 185                 190

Met Ile Glu Lys Thr Asn Ala Glu Arg Phe Tyr Val Phe Ser Asp Asp
        195                 200                 205

Pro Gln Trp Val Leu Glu His Leu Lys Leu Pro Val Ser Tyr Thr Val
210                 215                 220

Val Asp His Asn Arg Gly Ala Ala Ser Tyr Arg Asp Met Gln Leu Met
225                 230                 235                 240

Ser Ala Cys Arg His His Ile Ile Ala Asn Ser Thr Phe Ser Trp Trp
                245                 250                 255

Gly Ala Trp Leu Asn Pro Arg Pro Asp Lys Val Val Ile Ala Pro Arg
            260                 265                 270

His Trp Phe Asn Val Asp Val Phe Asp Thr Arg Asp Leu Tyr Cys Pro
        275                 280                 285

Gly Trp Ile Val Leu
        290

<210> SEQ ID NO 28
<211> LENGTH: 331
<212> TYPE: PRT
<213> ORGANISM: Bacteroides fragilis

<400> SEQUENCE: 28

Met Cys Asp Cys Leu Ser Ile Ile Leu Leu Val Lys Met Lys Lys Ile
1               5                  10                  15

Tyr Leu Lys Phe Val Asp Phe Trp Asp Gly Phe Asp Thr Ile Ser Asn
             20                  25                  30

Phe Ile Val Asp Ala Leu Ser Ile Gln Tyr Glu Val Val Leu Ser Asn
         35                  40                  45

Glu Pro Asp Tyr Leu Phe Tyr Ser Cys Phe Gly Thr Ser His Leu Glu
 50                  55                  60

Tyr Asp Cys Ile Lys Ile Met Phe Ile Gly Glu Asn Ile Val Pro Asp
 65                  70                  75                  80

Phe Asn Val Cys Asp Tyr Ala Ile Gly Phe Asn Tyr Ile Asp Phe Gly
             85                  90                  95
```

Asp Arg Tyr Leu Arg Leu Pro Leu Tyr Ala Ile Tyr Asp Gly Phe Ser
            100                 105                 110

Asn Leu Gln Asn Lys Lys Ile Asp Val Asn Lys Ala Leu Asp Arg Lys
        115                 120                 125

Phe Cys Ser Ile Val Val Ser Asn Asn Lys Trp Ala Asp Pro Ile Arg
130                 135                 140

Glu Thr Phe Phe Lys Leu Leu Ser Ser Tyr Lys Lys Val Asp Ser Gly
145                 150                 155                 160

Gly Arg Ala Trp Asn Asn Ile Gly Gly Pro Val Asp Asn Lys Leu Asp
                165                 170                 175

Phe Ile Ser Gln Tyr Lys Phe Asn Ile Ala Phe Glu Asn Ser Arg Val
            180                 185                 190

Leu Gly Tyr Thr Thr Glu Lys Ile Met Glu Pro Met Gln Val Asn Ser
        195                 200                 205

Ile Pro Val Tyr Trp Gly Asn Pro Leu Val Gly Lys Asp Phe Asn Val
210                 215                 220

Asp Ser Phe Val Asn Ala His Asp Phe Asp Ser Leu Glu Arg Leu Val
225                 230                 235                 240

Glu Tyr Ile Ile Glu Leu Asp Ser Ser Lys Asp Lys Tyr Leu Glu Met
                245                 250                 255

Leu Glu Lys Pro Trp Leu Leu Asp Lys Thr Tyr Leu Asp Trp Lys Gln
            260                 265                 270

Leu Leu Leu Asn Phe Ile Asn Asn Ile Met Met Lys Ser Tyr Lys Asp
        275                 280                 285

Ala Lys Tyr Leu Val Asn Tyr Gly His Ala Gly Lys Tyr Arg Asn Glu
290                 295                 300

Gln Arg Phe Trp Gly Arg Cys Glu Arg Lys Phe Lys Leu Gln Arg Ile
305                 310                 315                 320

Ile Glu Tyr Tyr Ser Gln Leu Phe Asp Arg Lys
                325                 330

<210> SEQ ID NO 29
<211> LENGTH: 297
<212> TYPE: PRT
<213> ORGANISM: Escherichia coli

<400> SEQUENCE: 29

Met Ser Ile Ile Arg Leu Gln Gly Gly Leu Gly Asn Gln Leu Phe Gln
1               5                   10                  15

Phe Ser Phe Gly Tyr Ala Leu Ser Lys Ile Asn Gly Thr Pro Leu Tyr
            20                  25                  30

Phe Asp Ile Ser His Tyr Ala Glu Asn Asp Asp His Gly Gly Tyr Arg
        35                  40                  45

Leu Asn Asn Leu Gln Ile Pro Glu Glu Tyr Leu Gln Tyr Tyr Thr Pro
    50                  55                  60

Lys Ile Asn Asn Ile Tyr Lys Leu Leu Val Arg Gly Ser Arg Leu Tyr
65                  70                  75                  80

Pro Asp Ile Phe Leu Phe Leu Gly Phe Cys Asn Glu Phe His Ala Tyr
                85                  90                  95

Gly Tyr Asp Phe Glu Tyr Ile Ala Gln Lys Trp Lys Ser Lys Lys Tyr
            100                 105                 110

Ile Gly Tyr Trp Gln Ser Glu His Phe Phe His Lys His Ile Leu Asp
        115                 120                 125

Leu Lys Glu Phe Phe Ile Pro Lys Asn Val Ser Glu Gln Ala Asn Leu

```
                130             135             140
Leu Ala Ala Lys Ile Leu Glu Ser Gln Ser Ser Leu Ser Ile His Ile
145                 150                 155                 160

Arg Arg Gly Asp Tyr Ile Lys Asn Lys Thr Ala Thr Leu Thr His Gly
                165                 170                 175

Val Cys Ser Leu Glu Tyr Tyr Lys Lys Ala Leu Asn Lys Ile Arg Asp
                180                 185                 190

Leu Ala Met Ile Arg Asp Val Phe Ile Phe Ser Asp Asp Ile Phe Trp
                195                 200                 205

Cys Lys Glu Asn Ile Glu Thr Leu Leu Ser Lys Lys Tyr Asn Ile Tyr
                210                 215                 220

Tyr Ser Glu Asp Leu Ser Gln Glu Glu Asp Leu Trp Leu Met Ser Leu
225                 230                 235                 240

Ala Asn His His Ile Ile Ala Asn Ser Ser Phe Ser Trp Trp Gly Ala
                245                 250                 255

Tyr Leu Gly Ser Ser Ala Ser Gln Ile Val Ile Tyr Pro Thr Pro Trp
                260                 265                 270

Tyr Asp Ile Thr Pro Lys Asn Thr Tyr Ile Pro Ile Val Asn His Trp
                275                 280                 285

Ile Asn Val Asp Lys His Ser Ser Cys
                290                 295

<210> SEQ ID NO 30
<211> LENGTH: 292
<212> TYPE: PRT
<213> ORGANISM: Thalassospira profundimaris

<400> SEQUENCE: 30

Met Val Ile Val Lys Leu Leu Gly Gly Leu Gly Asn Gln Met Phe Gln
1               5                   10                  15

Tyr Ala Thr Gly Arg Ala Val Ala Ser Arg Leu Asp Val Glu Leu Leu
                20                  25                  30

Leu Asp Val Ser Ala Phe Ala His Tyr Asp Leu Arg Arg Tyr Glu Leu
                35                  40                  45

Asp Asp Trp Asn Ile Thr Ala Arg Leu Ala Thr Ser Glu Glu Leu Ala
                50                  55                  60

Arg Ser Gly Val Thr Ala Ala Pro Pro Ser Phe Phe Asp Arg Ile Ala
65              70                  75                  80

Arg Phe Leu Arg Ile Asp Leu Pro Val Asn Cys Phe Arg Glu Ala Ser
                85                  90                  95

Phe Thr Tyr Asp Pro Arg Ile Leu Glu Val Ser Ser Pro Val Tyr Leu
                100                 105                 110

Asp Gly Tyr Trp Gln Ser Glu Arg Tyr Phe Leu Asp Ile Glu Lys Lys
                115                 120                 125

Leu Arg Gln Glu Phe Gln Leu Lys Ala Ser Ile Asp Ala Asn Asn His
                130                 135                 140

Ser Phe Lys Lys Lys Ile Asp Gly Leu Gly Lys Gln Ala Val Ser Leu
145                 150                 155                 160

His Val Arg Arg Gly Asp Tyr Val Thr Asn Pro Gln Thr Ala Ser Tyr
                165                 170                 175

His Gly Val Cys Ser Leu Asp Tyr Tyr Arg Ala Ala Val Asp Tyr Ile
                180                 185                 190

Ala Glu His Val Ser Asp Pro Cys Phe Phe Val Phe Ser Asp Asp Leu
                195                 200                 205
```

```
Glu Trp Val Gln Thr Asn Leu Asn Ile Lys Gln Pro Ile Val Leu Val
    210                 215                 220

Asp Ala Asn Gly Pro Asp Asn Gly Ala Ala Asp Met Ala Leu Met Met
225                 230                 235                 240

Ala Cys Arg His His Ile Ile Ala Asn Ser Ser Phe Ser Trp Trp Gly
                245                 250                 255

Ser Trp Leu Asn Pro Leu Asn Asp Lys Ile Ile Val Ala Pro Lys Lys
            260                 265                 270

Trp Phe Gly Arg Ala Asn His Asp Thr Thr Asp Leu Val Pro Asp Ser
        275                 280                 285

Trp Val Arg Leu
    290

<210> SEQ ID NO 31
<211> LENGTH: 2851
<212> TYPE: DNA
<213> ORGANISM: Unknown
<220> FEATURE:
<223> OTHER INFORMATION: Expression fragment for integration into E.
      coli genome.

<400> SEQUENCE: 31
tggccagatg attaattcct aattttgtt gacactctat cattgataga gttatttac       60 cactccctat cagtgataga gaaaagtgaa atgaatagtt cgacaaaaat ctagaaataa    120
ttttgtttaa ctttaagaag gagatataca aatgtactat ttaaaaaaca caaacttttg    180
gatgttcggt ttattctttt tcttttactt ttttatcatg ggagcctact tcccgttttt    240
cccgatttgg ctacatgaca tcaaccatat cagcaaaagt gatacgggta ttatttttgc    300
cgctatttct ctgttctcgc tattattcca accgctgttt ggtctgcttt ctgacaaact    360
cgggctgcgc aaatacctgc tgtggattat taccggcatg ttagtgatgt ttgcgccgtt    420
cttatttttt atcttcgggc cactgttaca atacaacatt ttagtaggat cgattgttgg    480
tggtatttat ctaggctttt gttttaacgc cggtgcgcca gcagtagagg catttattga    540
gaaagtcagc cgtcgcagta atttcgaatt tggtcgcgcg cggatgtttg gctgtgttgg    600
ctgggcgctg tgtgcctcga ttgtcggcat catgttcacc atcaataatc agtttgtttt    660
ctggctgggc tctggctgtg cactcatcct cgccgtttta ctctttttcg ccaaaacgga    720
tgcgccctct tctgccacgg ttgccaatgc ggtaggtgcc aaccattcgg catttagcct    780
taagctggca ctggaactgt tcagacagcc aaaactgtgg ttttgtcac tgtatgttat     840 tggcgttttcc tgcacctacg atgttttttga ccaacagttt gctaatttct ttacttcgtt    900
ctttgctacc ggtgaacagg gtacgcgggt atttggctac gtaacgacaa tgggcgaatt    960
acttaacgcc tcgattatgt tctttgcgcc actgatcatt aatcgcatcg gtgggaaaaa    1020
cgccctgctg ctggctggca ctattatgtc tgtacgtatt attggctcat cgttcgccac    1080
ctcagcgctg gaagtggtta ttctgaaaac gctgcatatg tttgaagtac gttcctgct     1140 ggtgggctgc tttaaatata ttaccagcca gtttgaagtg cgttttcag cgacgattta     1200 tctggtctgt ttctgcttct taagcaact ggcgatgatt tttatgtctg tactggcggg     1260
caatatgtat gaaagcatcg gtttccaggg cgcttatctg gtgctgggtc tggtggcgct    1320
gggcttcacc ttaatttccg tgttcacgct tagcggcccc ggcccgcttt cctgctgcg     1380 tcgtcaggtg aatgaagtcg ctgggagcta agcggccgcg tcgacacgca aaaaggccat    1440
ccgtcaggat ggccttctgc ttaatttgat gcctggcagt ttatggcggg cgtcctgccc    1500
```

```
gccaccctcc gggccgttgc ttcgcaacgt tcaaatccgc tcccggcgga tttgtcctac    1560
tcaggagagc gttcaccgac aaacaacaga taaaacgaaa ggcccagtct ttcgactgag    1620
cctttcgttt tatttgatgc ctggcagttc cctactctcg catggggaga ccccacacta    1680
ccatcatgta tgaatatcct ccttagttcc tattccgaag ttcctattct ctagaaagta    1740
taggaacttc ggcgcgtcct acctgtgaca cgcgtgccgc agtctcacgc ccggagcgta    1800
gcgaccgagt gagctagcta tttgtttatt tttctaaata cattcaaata tgtatccgct    1860
catgagacaa taaccctgat aaatgcttca ataatattga aaaggaaga gtatgaggga    1920 agcggtgatc gccgaagtat cgactcaact atcagaggta gttggcgtca tcgagcgcca    1980
tctcgaaccg acgttgctgg ccgtacattt gtacggctcc gcagtggatg gcggcctgaa    2040
gccacacagt gatattgatt tgctggttac ggtgaccgta aggcttgatg aaacaacgcg    2100
gcgagctttg atcaacgacc ttttggaaac ttcggcttcc cctggagaga gcgagattct    2160
ccgcgctgta gaagtcacca ttgttgtgca cgacgacatc attccgtggc gttatccagc    2220
taagcgcgaa ctgcaatttg agaatggca gcgcaatgac attcttgcag gtatcttcga    2280
gccagccacg atcgacattg atctggctat cttgctgaca aaagcaagag aacatagcgt    2340
tgccttggta ggtccagcgg cggaggaact ctttgatccg gttcctgaac aggatctatt    2400
tgaggcgcta aatgaaacct aacgctatg gaactcgccg cccgactggg ctggcgatga    2460
gcgaaatgta gtgcttacgt tgtcccgcat ttggtacagc gcagtaaccg gcaaaatcgc    2520
gccgaaggat gtcgctgccg actgggcaat ggagcgcctg ccggcccagt atcagcccgt    2580
catacttgaa gctagacagg cttatcttgg acaagaagaa gatcgcttgg cctcgcgcgc    2640
agatcagttg gaagaatttg tccactacgt gaaaggcgag atcaccaagg tagtcggcaa    2700
ataatgtcta acaattcgtt caagccgagg ggccgcaaga tccggccacg atgacccggt    2760
cgtcgggtac cggcagggcg gggcgtaagg cgcgccattt aaatgaagtt cctattccga    2820
agttcctatt ctctagaaag tataggaact t                                    2851
```

<210> SEQ ID NO 32
<211> LENGTH: 4568
<212> TYPE: DNA
<213> ORGANISM: Unknown
<220> FEATURE:
<223> OTHER INFORMATION: Expression construct for integration into E.
      coli genome.

<400> SEQUENCE: 32

```
acaggttggc tgataagtcc ccggtctagc ttgcatgcag attgcagcat tacacgtctt      60
gagcgattgt gtaggctgga gctgcttcga agttcctata ctttctagag aataggaact    120
tcggaatagg aacttcattt aaatggcgcg ccttacgccc cgccctgccg gtaccgagag    180
cgcttttgaa gctggggtgg gcgaagaact ccagcatgag atccccgcgc tggaggatca    240
tccagccggc gtcccggaaa acgattccga agcccaacct ttcatagaag gcggcggtgg    300
aatcgaaatc tcgtgatggc aggttgggcg tcgcttggtc ggtcatttcg aaccccagag    360
tcccgctcag aagaactcgt caagaaggcg atagaaggcg atgcgctgcg aatcgggagc    420 ggcgatacog taaagcacga ggaagcggtc agcccattcg ccgccaagct cttcagcaat    480
atcacgggta gccaacgcta tgtcctgata gcggtccgcc acacccagcc ggccacagtc    540
gatgaatcca gaaaagcggc catttccac catgatattc ggcaagcagg catcgccatg    600
ggtcacgacg agatcctcgc cgtcgggcat gcgcgccttg agcctggcga acagttcggc    660
```

```
tggcgcgagc ccctgatgct cttcgtccag atcatcctga tcgacaagac cggcttccat      720
ccgagtacgt gctcgctcga tgcgatgttt cgcttggtgg tcgaatgggc aggtagccgg      780
atcaagcgta tgcagccgcc gcattgcatc agccatgatg gatactttct cggcaggagc     840
aaggtgagat gacaggagat cctgccccgg cacttcgccc aatagcagcc agtcccttcc      900
cgcttcagtg acaacgtcga gcacagctgc gcaaggaacg cccgtcgtgg ccagccacga      960
tagccgcgct gcctcgtcct gcagttcatt cagggcaccg gacaggtcgg tcttgacaaa     1020
aagaaccggg cgcccctgcg ctgacagccg gaacacggcg gcatcagagc agccgattgt     1080
ctgttgtgcc cagtcatagc cgaatagcct ctccacccaa gcggccggag aacctgcgtg     1140
caatccatct tgttcaatca tgcgaaacga tcctcatcct gtctcttgat cagatcttga     1200 tccctgcgc catcagatcc ttggcggcaa gaaagccatc cagtttactt tgcagggctt      1260
cccaacctta ccagagggcg ccccagctgg caattccggt tcgcttgctg tccataaaac     1320
cgcccagtct agctatcgcc atgtaagccc actgcaagct acctgctttc tctttgcgct     1380
tgcgttttcc cttgtccaga tagcccagta gctgacattc atccggggtc agcaccgttt     1440
ctgcggactg gctttctacg tgttccgctt cctttagcag cccttgcgcc ctgagtgctt     1500
gcggcagcgt gaggggatct tgacgcgtgt cacaggtagg acgcgccgaa gttcctatac     1560
tttctagaga ataggaactt cggaatagga actaaggagg atattcatac atgatggtag     1620
tgttcgaaat taatacgact cactataggg gaattgattc tggtaccaaa tgagtcgacc     1680
ggccagatga ttaattccta attttgttg acactctatc attgatagag ttatttacc      1740 actccctatc agtgatagag aaaagtgaaa tgaatagttc gacaaaaatc tagaaataat     1800
tttgtttaac tttaagaagg agatatacaa atgccgtccg aagcattccg tcgtcaccgt     1860
gcttatcgcg aaaacaaact gcagccactg gtctctgtcc tgatctgcgc atacaacgtt     1920
gagaaatact tcgcacagtc tctggcagct gtagttaacc agacctggcg taacctggat     1980
atcctgatcg tagatgacgg ctctacggat ggtacgctgg cgatcgcaca gcgtttccag     2040
gaacaggacg gtcgtatccg cattctcgct cagccgcgta actctggtct gatcccgtct     2100
ctgaacatcg gtcggacga actggccaaa tctggtggtg gtggcgaata catcgcccgt      2160
actgacgccg acgacattgc ggccccggat tggatcgaaa aaatcgtagg tgaaatggag     2220
aaagaccgct ctatcatcgc gatgggtgct tggctggaag ttctgtccga agagaaagac     2280
ggtaaccgtc tggcccgtca ccatgaacac ggcaaaatct ggaaaaaacc gacccgtcac     2340
gaagatatcg cggacttctt cccgttcggt aacccgatcc ataacaacac catgatcatg     2400
cgtcgtagcg taatcgacgg tggtctgcgt tacaacaccg aacgtgattg ggcagaagac     2460
taccagtttt ggtatgacgt gtctaaactg ggtcgtctgg cttactaccc agaagcgctg     2520
gttaaatacc gtctgcacgc caaccaggtt agctccaaat actccatccg tcagcacgaa     2580
atcgcacagg gtatccagaa aacggctcgt aacgacttcc tgcagtccat gggttcaaa      2640 accgtttcg actctctgga gtaccgtcag atcaaagcgg ttgcgtatga gctgctggag     2700
aaacacctgc cggaagagga ctttgaacgt gcgcgtcgtt tcctgtacca gtgcttcaaa     2760
cgtaccgaca ctctgccggc gggtgcatgg ctcgactttg cagcggatgg tcgtatgcgt     2820
cgtctgttta ccctgcgtca gtacttcggt atcctgcatc gtcctgaa aaaccgctaa      2880 tgatttcgtc gacacacagg aaacatatta aaaattaaaa cctgcaggag tttaaacgcg     2940
gccgcgatat cgttgtaaaa cgacggccag tgcaagaatc ataaaaaatt tatttgcttt     3000
caggaaaatt tttctgtata atagattcat aaatttgaga gaggagtttt tgtgagcgga     3060
```

| | |
|---|---|
| taacaattcc ccatcttagt atattagtta agtataaata cacaaggaga tataccatga | 3120 |
| cgcaatttaa tcccgttgat catccacatc gccgctacaa cccgctcacc gggcaatgga | 3180 |
| ttctggtttc accgcaccgc gctaagcgcc cctggcaggg ggcgcaggaa acgccagcca | 3240 |
| aacaggtgtt acctgcgcac gatccagatt gcttcctctg cgcaggtaat gtgcgggtga | 3300 |
| caggcgataa aaaccccgat tacaccggga cttacgtttt cactaatgac tttgcggctt | 3360 |
| tgatgtctga cacgccagat gcgccagaaa gtcacgatcc gctgatgcgt tgccagagcg | 3420 |
| cgcgcggcac cagccgggtg atctgctttt caccggatca cagtaaaacg ctgccagagc | 3480 |
| tcagcgttgc agcattgacg gaaatcgtca aaacctggca ggagcaaacc gcagaactgg | 3540 |
| ggaaaacgta cccatggggtg caggttttg aaaacaaagg cgcggcgatg ggctgctcta | 3600 |
| acccgcatcc gcacggtcag atttgggcaa atagcttcct gcctaacgaa gctgagcgcg | 3660 |
| aagaccgcct gcaaaaagaa tattttgccg aacagaaatc accaatgctg gtggattatg | 3720 |
| ttcagcgcga gctggcagac ggtagccgta ccgttgtcga aaccgaacac tggttagccg | 3780 |
| tcgtgcctta ctgggctgcc tggccgttcg aaacgctact gctgcccaaa gcccacgttt | 3840 |
| tacggatcac cgatttgacc gacgcccagc gcagcgatct ggcgctggcg ttgaaaaagc | 3900 |
| tgaccagtcg ttatgacaac ctcttccagt gctccttccc ctactctatg ggctggcacg | 3960 |
| gcgcgccatt taatggcgaa gagaatcaac actggcagct gcacgcgcac ttttatccgc | 4020 |
| ctctgctgcg ctccgccacc gtacgtaaat ttatggttgg ttatgaaatg ctggcagaga | 4080 |
| cccagcgaga cctgaccgca gaacaggcag cagagcgttt gcgcgcagtc agcgatatcc | 4140 |
| attttcgcga atccggagtg taacgcggag gcgcgccatt taaatcaacc tcagcggtca | 4200 |
| tagctgtttc ctgtgactga gcaataacta gcataacccc ttggggcctc taaacgggtc | 4260 |
| ttgaggggtt ttttgctgaa accaatttgc ctggcggcag tagcgcggtg gtcccacctg | 4320 |
| acccccatgcc gaactcagaa gtgaaacgcc gtagcgccga tggtagtgtg ggtctcccc | 4380 |
| atgcgagagt agggaactgc caggcatcaa ataaaacgaa aggctcagtc gaaagactgg | 4440 |
| gcctttcggg atccaggccg gcctgttaac gaattaatct tccgcggcaa caaaaattag | 4500 |
| gaattaatca tctggccaat ttcaggtggc acttttcggg cagaccgggg acttatcagc | 4560 |
| caacctgt | 4568 |

<210> SEQ ID NO 33
<211> LENGTH: 6521
<212> TYPE: DNA
<213> ORGANISM: Unknown
<220> FEATURE:
<223> OTHER INFORMATION: Transposon cassette.

<400> SEQUENCE: 33

| | |
|---|---|
| acaggttggc tgataagtcc ccggtctagc ttgcatgcag attgcagcat tacacgtctt | 60 |
| gagcgattgt gtaggctgga gctgcttcga aattaatacg actcactata ggggaattga | 120 |
| ttctggtacc aaatgagtcg accggccaga tgattaattc ctaattttg ttgacactct | 180 |
| atcattgata gagttatttt accactccct atcagtgata gagaaaagtg aaatgaatag | 240 |
| ttcgacaaaa atctagaaat aattttgttt aactttaaga aggagatata caaatgctga | 300 |
| acaacgcgat gtctgttgtt atcctggcgg cgggtaaagg tacccgtatg tactctgacc | 360 |
| tgccgaaagt tctgcacacc ctggcgggta agcgatggt tcagcacgtt atcgacgcgg | 420 |
| cgaacgaact gggtgcggcg cacgttcacc tggtttacgg tcacggtggt gacctgctga | 480 |

```
aacaggcgct gaaagacgac aacctgaact gggttctgca ggcggaacag ctgggtaccg    540
gtcacgcgat gcagcaggcg gcgccgttct tcgcggacga cgaagacatc ctgatgctgt    600
acggtgacgt tccgctgatc tctgttgaaa ccctgcagcg tctgcgtgac gcgaaaccgc    660
agggtggtat cggtctgctg accgttaaac tggacgaccc gaccggttac ggtcgtatca    720
cccgtgaaaa cggtaaagta accggtatcg ttgaacacaa agacgcgacc gacgaacagc    780
gtcagatcca ggagatcaac accggtatcc tgatcgcgaa cggtgcagac atgaaacgtt    840
ggctggcgaa actgaccaac aacaacgcgc agggtgaata ctacatcacc gacatcatcg    900
cgctggcgta ccaggaaggt cgtgaaatcg ttgcggttca cccgcagcgt ctgtctgaag    960
ttgaaggtgt taacaaccgt ctgcagctgt ctcgtctgga acgtgtttac cagtctgaac   1020
aggcggaaaa actgctgctg gcgggtgtta tgctgcgtga cccggcgcgt ttcgacctgc   1080
gtggtaccct gacccacggt cgtgacgttg aaatcgacac caacgttatc atcgaaggta   1140
acgttaccct gggtcaccgt gtaaaaatcg gcaccggttg cgttatcaaa aactctgtta   1200
tcggtgacga ctgcgaaatc tctccgtaca ccgttgttga agacgcgaac ctggcggcgg   1260
cgtgcaccat cggtccgttc gcgcgtctgc gtccgggtgc ggaactgctg aaggtgcgc    1320 acgttggtaa cttcgttgaa atgaaaaaag cgcgtctggg taaaggttct aaagcgggtc   1380
acctgaccta cctgggtgac gcggaaatcg gtgacaacgt taacatcggt gcgggtacca   1440
tcacctgcaa ctacgacggt gcgaacaaat tcaaaaccat catcggtgac gacgttttcg   1500
ttggttctga cacccagctg gttgcgccgg ttaccgttgg taaaggtgcg accatcgcgg   1560
cgggtaccac cgttacccgt aacgttggtg aaaacgcgct ggcgatctct cgtgttccgc   1620
agacccagaa agaaggttgg cgtcgtccgg ttaaaaaaaa ataacgaagg agatagaacc   1680
atgtccaacc gtaaatactt cggtacggac ggtatccgtg gtcgtgtagg tgatgctccg   1740
attacgccgg atttcgtcct gaaactcggt tgggcagcgg gtaaagttct cgcacgtcac   1800
ggctctcgta aaatcatcat cggtaaagac accgtatct ctggttacat gctcgaatct   1860
gcactggaag cgggtctggc tgcagctggt ctgtctgcac tgttcacggg tccgatgcca   1920
accccagctg tagcgtacct gactcgcact ttccgtgcag aagcaggtat cgtgatctct   1980
gcctctcaca cccgttcta cgacaacggt atcaaattct tcagcatcga tggtaccaaa   2040
ctcccagacg cggttgaaga ggctatcgaa gcggaaatgg agaaagaaat ctcttgtgta   2100
gactctgccg aactcggtaa agcgtctcgt atcgttgatg cagcgggtcg ttacatcgag   2160
ttctgcaaag ccaccttccc gaacgaactg agcctgtctg agctgaaaat cgtcgtagac   2220
tgtgccaacg gtgcgactta ccacattgcc ccaaacgtac tgcgtgagct gggtgctaac   2280
gtcatcgcga tcgttgtga accgaacggt gtcaacatca cgcggaagt aggtgcgacc    2340 gatgttcgtg cactgcaggc tcgtgtactc gcggagaaag cggatctcgg tatcgccttt   2400
gacggtgatg tgaccgtgt tatcatggtt gaccacgaag gtaacaaagt ggatggtgac    2460
cagatcatgt acatcattgc ccgtgaaggt ctgcgtcagg gtcagctgcg tggtggtgca   2520
gtaggtaccc tcatgagcaa catgggtctg gaactggccc tgaaacagct gggtatccca   2580
ttcgctcgtc taaagtaggc gaccgttac gttctgagaa aaatgcagga gaaaggttgg    2640
cgtatcggtg ccgaaaactc tggtcacgtc atcctgctgg acaaaaccac taccggtgac   2700
ggtatcgtag caggtctgca ggtactcgcc gctatggccc gtaaccacat gtccctccat   2760
gacctctgct ctggtatgaa aatgttcccg cagatcctgg ttaacgttcg ttacaccgca   2820
ggttctggtg atccgctgga acacgagtct gtgaaagccg ttaccgcaga agtggaagcg   2880
```

```
gccctgggta accgtggtcg tgtactgctg cgtaaatccg gtactgagcc actgatccgt    2940
gttatggttg agggcgaaga tgaagcccag gtcaccgaat tgcgcaccg tattgccgac     3000 gcagtcaaag cggtttaatt tcgtcgacac acaggaaaca tattaaaaat taaaacctgc    3060
aggagtttaa acgcggccgc gatatcgttg taaaacgacg gccagtgcaa gaatcataaa    3120
aaatttattt gctttcagga aaattttttct gtataataga ttcataaatt tgagagagga   3180 gttttttgtga gcggataaca attccccatc ttagtatatt agttaagtat aaatacacaa   3240
ggagatatac atatgtgcgg tatcgttggt gctatcgcac agcgtgatgt agcggagatc    3300
ctcctggaag gtctgcgtcg tctcgaatac cgtggttacg actctgccgg tctggcagta    3360
gtggatgcag aaggtcacat gactcgtctg cgtcgtctgg gtaaagtgca gatgctcgcg    3420 caggcggcg aagaacaccc actccacggt ggtacgggta tcgcacacac tcgttgggca    3480
acccacggtg aaccgtctga ggtcaacgca caccgcatg ttagcgagca catcgtagtc    3540
gttcacaacg gtatcatcga gaaccacgaa ccactccgtg aggaactcaa agcccgtggt   3600
tacaccttcg taagcgaaac cgacacggaa gttatcgccc acctcgttaa ctgggaactc   3660
aaacagggtg gtactctgcg tgaagcagtt ctgcgtgcca ttccacagct gcgtggtgca   3720
tacggtaccg tgatcatgga ctctcgtcat ccggataccc tgctcgccgc acgttctggt   3780
tctccactcg ttatcggtct gggtatgggt gagaacttca tcgcctctga tcagctggcc   3840
ctgctcccag ttacccgtcg cttcatcttc ctggaagagg gtgacatcgc cgaaatcacc   3900
cgtcgttccg ttaacatctt cgacaaaacg ggtgcggaag ttaaacgtca ggacatcgag   3960
tctaacctgc agtatgacgc tggtgacaaa ggcatctacc gtcactacat gcagaaagag   4020
atctacgaac agccgaacgc gatcaaaaac accctgaccg gtcgtatctc tcacggtcag   4080
gttgacctgt ctgagctggg tccaaacgcg gacgaactcc tgtccaaagt cgagcacatc   4140
cagatcctgg cttgtggtac ctcttacaac tccggtatgg tttctcgtta ctggttcgaa   4200
tctctggcag gtatcccatg cgacgttgaa atcgcctccg aattccgtta tcgtaaatct   4260
gcggtacgtc gtaactccct catgatcacc ctgtctcagt ctggtgaaac cgctgatact   4320
ctggcaggtc tgcgtctcag caaagaactg ggttacctgg gttctctggc catctgcaac   4380
gttccgggtt ctagcctggt tcgtgagtct gacctggctc tgatgaccaa cgcgggtacg   4440
gagatcggtg ttgcctctac caaagcgttc actacccagc tcactgtcct gctgatgctg   4500
gttgccaaac tgtctcgtct caaaggcctc gacgctagca tcgaacacga catcgtacac   4560
ggtctgcagg ccctcccatc tcgtatcgag cagatgctgt ctcaggacaa acgtatcgaa   4620
gcactggcag aagacttcag cgacaaacac cacgcgctgt ttctgggtcg tggtgaccag   4680
tacccaattg cgctggaagg tgccctgaaa ctgaaagaga tcagctacat ccatgcagag   4740
gcatacgcag cgggtgagct gaaacatggt ccactggccc tgatcgacgc agatatgccg   4800
gttattgtgg ttgctccgaa caacgaactg ctggagaaac tgaaatccaa catcgaggaa   4860
gtacgtgcgc gtggtggtca gctgtacgtg tttgctgacc aggacgcggg tttcgtttcc   4920
agcgacaaca tgcacatcat cgaaatgccg catgttgaag aggtaatcgc gccaatcttc   4980
tacaccgtac cgctgcagct gctggcgtac catgtagccc tgatcaaagg tacgacgtt   5040 gaccagccgc gtaacctggc gaaatccgtg accgtggaat aacgcggagg cgcgccattt   5100
aaatcaacct cagcggtcat agctgttttcc tgtgactgag caataactag cataaccccct   5160 tggggcctct aaacgggtct tgaggggttt tttgctgaaa ccaatttgcc tggcggcagt   5220
```

| | | |
|---|---|---|
| agcgcggtgg tcccacctga ccccatgccg aactcagaag tgaaacgccg tagcgccgat | 5280 |
| ggtagtgtgg ggtctcccca tgcgagagta gggaactgcc aggcatcaaa taaaacgaaa | 5340 |
| ggctcagtcg aaagactggg cctttcggga tccaggccgg cctgttaacg aattaatctt | 5400 |
| ccgcggcggt atcgataagc ttgatatcga attccgaagt tcctattctc tagaaagtat | 5460 |
| aggaacttca ggtctgaaga ggagtttacg tccagccaag ctagcttggc tgcaggtcgt | 5520 |
| cgaaattcta ccgggtaggg gaggcgcttt tcccaaggca gtctggagca tgcgctttag | 5580 |
| cagccccgct gggcacttgg cgctacacaa gtggcctctg gcctcgcaca cattccacat | 5640 |
| ccaccggtag gcgccaaccg gctccgttct ttggtggccc cttcgcgcca ccttctactc | 5700 |
| ctccctagt caggaagttc cccccgccc cgcagctcgc gtcgtgcagg acgtgacaaa | 5760 |
| tggaagtagc acgtctcact agtctcgtgc agatggacag caccgctgag caatggaagc | 5820 |
| gggtaggcct ttggggcagc ggccaatagc agctttgctc cttcgctttc tgggctcaga | 5880 |
| ggctgggaag gggtgggtcc ggggcgggc tcagggcgg gctcagggc ggggcgggcg | 5940 |
| cccgaaggtc ctccggaggc ccggcattct gcacgcttca aaagcgcacg tctgccgcgc | 6000 |
| tgttctcctc ttcctcatct ccgggccttt cgacctgcag cctgttgaca attaatcatc | 6060 |
| ggcatagtat atcggcatag tataatacga caaggtgagg aactaaacca tgggtcaaag | 6120 |
| tagcgatgaa gccaacgctc ccgttgcagg gcagtttgcg cttcccctga gtgccacctt | 6180 |
| tggcttaggg gatcgcgtac gcaagaaatc tggtgccgct tggcagggtc aagtcgtcgg | 6240 |
| ttggtattgc acaaaactca ctcctgaagg ctatgcggtc gagtccgaat cccacccagg | 6300 |
| ctcagtgcaa atttatcctg tggctgcact tgaacgtgtg gcctaatgag gggatcaatt | 6360 |
| ctctagagct cgctgatcag aagttcctat tctctagaaa gtataggaac ttcgatggcg | 6420 |
| cctcatccct gaagccaata caacaaaaat taggaattaa tcatctggcc aatttcaggt | 6480 |
| ggcacttttc gggcagaccg gggacttatc agccaacctg t | 6521 |

<210> SEQ ID NO 34
<211> LENGTH: 3856
<212> TYPE: DNA
<213> ORGANISM: Unknown
<220> FEATURE:
<223> OTHER INFORMATION: Transposon cassette.

<400> SEQUENCE: 34

| | | |
|---|---|---|
| acaggttggc tgataagtcc ccggtctgcc cgaaaagtgc cacctgaaat tggccagatg | 60 |
| attaattcct aattttttgtt gattctggta ccaaatgagt cgaccggcca gatgattaat | 120 |
| tcctaatttt tgttgacact ctatcattga tagagttatt ttaccactcc ctatcagtga | 180 |
| tagagaaaag tgaaatgaat agttcgacaa aaatctagaa ataattttgt ttaacttttaa | 240 |
| gaaggagata tacaaatgct gacggaagtg cgcccggtct ctacgacgaa accgctggtg | 300 |
| tctgtgattc tgccggtgaa caaattcaac ccgtatctgg atcgtgcaat tcattcaatc | 360 |
| ctgagtcagt cctatccgtc gattgaactg attatcattg caaacaattg caccaatgac | 420 |
| tttttcgatg ctctgaaaaa acgtgaatgt gaaaccatta agtgctgcg cacgaacatc | 480 |
| gcgtatctgc cgtactgcct gaataaaggc ctggatctgt gtaacggtga ctttgttgcc | 540 |
| cgcatggatt cagatgacat ttcgcacccg gaacgtatcg atcgccaggt cgacttcctg | 600 |
| attaacaatc cggacatcga tgtggttggc accaatgcag tctatattga tgaagatgac | 660 |
| atcgaactgg aaaaaagcaa cctgccggtg aacaataacg ctattcgtaa aatgctgccg | 720 |
| tataaatgct gtctggtgca tccgtctgtt atgtttcgca aaaatgtcgt gatcaccagc | 780 |

```
ggcggttaca tgttcgcgaa ttattctgaa gattacgaac tgtggaaccg tctggccgtt    840
gaaggccgca attttttataa cctgagcgaa tacctgctgt attaccgtct gcacaataac    900
caatcaacgt cgaaaaataa cctgtttatg gtgatggcga acgatgtcgc cattaaagtg    960
aaatatttcc tgctgaccaa gaaaattagc tacctgctgg gtatcattcg cacggtcttt   1020
tctgtgttct attgcaaata catcaaatga tttcgtcgac acacaggaaa catattaaaa   1080
attaaaacct gcaggagttt aaacgcggcc gcgatatcgt tgtaaaacga cggccagtgc   1140
aagaatcata aaaaatttat ttgctttcag gaaaattttt ctgtataata gattcataaa   1200
tttgagagag gagttttttgt gagcggataa caattcccca tcttagtata ttagttaagt   1260
ataaatacac cgcggaggcg tcgaaggaga tacaaccatg agagttctgg ttaccggtgg   1320
tagcggttac attggaagtc atacctgtgt gcaattactg caaaacggtc atgatgtcat   1380
cattcttgat aacctctgta acagtaagcg cagcgtactg cctgttatcg agcgtttagg   1440
cggcaaacat ccaacgtttg ttgaaggcga tattcgtaac gaagcgttga tgaccgagat   1500
cctgcacgat cacgctatcg acaccgtgat ccacttcgcc gggctgaaag ccgtgggcga   1560
atcggtacaa aaaccgctgg aatattacga caacaatgtc aacggcactc tgcgcctgat   1620
tagcgccatg cgcgccgcta acgtcaaaaa ctttattttt agctcctccg ccaccgttta   1680
tggcgatcag cccaaaattc catacgttga aagcttcccg accggcacac cgcaaagccc   1740
ttacggcaaa agcaagctga tggtggaaca gatcctcacc gatctgcaaa aagcccagcc   1800
ggactggagc attgccctgc tgcgctactt caacccggtt ggcgcgcatc cgtcgggcga   1860
tatgggcgaa gatccgcaag gcattccgaa taacctgatg ccatacatcg cccaggttgc   1920
tgtaggccgt cgcgactcgc tggcgatttt tggtaacgat tatccgaccg aagatggtac   1980
tggcgtacgc gattacatcc acgtaatgga tctggcggac ggtcacgtcg tggcgatgga   2040
aaaactggcg aacaagccag gcgtacacat ctacaacctc ggcgctggcg taggcaacag   2100
cgtgctggac gtggttaatg ccttcagcaa agcctgcggc aaaccggtta attatcattt   2160
tgcaccgcgt cgcgagggcg accttccggc ctactgggcg gacgccagca agccgaccg    2220 tgaactgaac tggcgcgtaa cgcgcacact cgatgaaatg gcgcaggaca cctggcactg   2280
gcagtcacgc catccacagg gatatcccga ttaacgccat ttaaatcaac ctcagcggtc   2340
atagctgttt cctgtgactg agcaataact agcataaccc cttggggcct ctaaacgggt   2400
cttgaggggt ttttttgctga aaccaatttg cctggcggca gtagcgcggt ggtcccacct   2460
gaccccatgc cgaactcaga agtgaaacgc cgtagcgccg atggtagtgt ggggtctccc   2520
catgcgagag tagggaactg ccaggcatca aataaaacga aaggctcagt cgaaagactg   2580
ggcctttcgg gatccaggcc ggcctgttaa cgaattaatc ttccgcggcg gtatcgataa   2640
gcttgatatc gaggctgaca tgggaattag ccatggtcca tatgaatatc ctccttagtt   2700
cctattccga agttcctatt ctctagaaag tataggaact cggcgcgcc tacctgtgac    2760 ggaagatcac ttcgcagaat aaataaatcc tggtgtccct gttgataccg ggaagccctg   2820
ggccaacttt tggcgaaaat gagacgttga tcggcacgta agaggttcca actttcacca   2880
taatgaaata agatcactac cgggcgtatt ttttgagttg tcgagatttt caggagctaa   2940
ggaagctaaa atggagaaaa aaatcactgg atataccacc gttgatatat cccaatggca   3000
tcgtaaagaa cattttgagg catttcagtc agttgctcaa tgtacctata accagaccgt   3060
tcagctggat attacggcct ttttaaagac cgtaaagaaa aataagcaca gtttttatcc   3120
```

-continued

```
ggcctttatt cacattcttg cccgcctgat gaatgctcat ccggaattac gtatggcaat    3180
gaaagacggt gagctggtga tatgggatag tgttcaccct tgttacaccg ttttccatga    3240
gcaaactgaa acgttttcat cgctctggag tgaataccac gacgatttcc ggcagtttct    3300
acacatatat tcgcaagatg tggcgtgtta cggtgaaaac ctggcctatt tccctaaagg    3360
gtttattgag aatatgtttt tcgtctcagc caatccctgg gtgagtttca ccagttttga    3420
tttaaacgtg gccaatatgg acaacttctt cgcccccgtt ttcaccatgg caaatatta     3480 tacgcaaggc gacaaggtgc tgatgccgct ggcgattcag gttcatcatg ccgtttgtga    3540
tggcttccat gtcggcagat gcttaatgaa tacaacagta ctgcgatgag tggcagggcg    3600
gggcgtaagg cgcgccattt aaatgaagtt cctattccga agttcctatt ctctagaaag    3660
tataggaact tcgaagcagc tccagcctac acaatcgctc aagacgtgta atgctgcaat    3720
ctgcatgcaa gcttggcact ggcgatggcg cctcatccct gaagccaata agcagctcca    3780
gcctacacaa tcgctcaaga cgtgtaatgc tgcaatctgc atgcaagcta gaccggggac    3840
ttatcagcca acctgt                                                    3856
```

<210> SEQ ID NO 35
<211> LENGTH: 3955
<212> TYPE: DNA
<213> ORGANISM: Unknown
<220> FEATURE:
<223> OTHER INFORMATION: EZ-Tn5 Transposon

<400> SEQUENCE: 35

```
tggccagatg attaattcct aattttttgtt gacactctat cattgataga gttatttttac     60 cactccctat cagtgataga gaaaagtgaa atgaatagtt cgacaaaaat ctagaaataa    120
ttttgtttaa cttaagaag gagatataca acatgcaaaa actactatct ttaccgtcca     180
atctggttca gtcttttcat gaactggaga gggtgaatcg taccgattgg ttttgtactt    240
ccgacccggt aggtaagaaa cttggttccg gtggtggaac atcctggctg cttgaagaat    300
gttataatga atattcagat ggtgctactt ttggagagtg gcttgaaaaa gaaaaaagaa    360
ttcttcttca tgcgggtggg caaagccgtc gtttacccgg ctatgcacct tctggaagaa    420
ttctcactcc ggttcctgtg ttccggtggg agagagggca acatctggga caaaatctgc    480
tttctctgca acttccccta tatgaaaaaa tcatgtcttt ggctccggat aaactccata    540
cactgattgc gagtggtgat gtctatattc gttcggagaa accttttgcag agtattcccg    600 aagcggatgt ggtttgttat ggactgtggg tagatccgtc tctggctacc catcatggcg    660
tgtttgcttc cgatcgcaaa catcccgaac aactcgactt tatgcttcag aagccttcgt    720
tggcagaatt ggaatcttta tcgaagaccc atttgttcct gatggacatc ggtatatggc    780
ttttgagtga ccgtgccgta gaaatcttga tgaaacgttc tcataaagaa agctctgaag    840
aactaaagta ttatgatctt tattccgatt tggattagc  tttgggaact catccccgta    900
ttgaagacga agaggtcaat acgctatccg ttgctattct gcctttgccg ggaggagagt    960
tctatcatta cgggaccagt aaagaactga tttcttcaac tctttccgta cagaataagg   1020
tttacgatca gcgtcgtatc atgcaccgta agtaaagcc caatccggct atgtttgtcc    1080
aaaatgctgt cgtgcggata cctctttgtg ccgagaatgc tgatttatgg atcgagaaca   1140
gtcatatcgg accaaagtgg aagattgctt cacgacatat tattaccggg gttccggaaa   1200
atgactggtc attggctgtg cctgccgag tgtgtagta tgtggttccg atgggtgata    1260
agggctttgt tgcccgtcca tacggtctgg acgatgtttt caaggagat ttgagagatt    1320
```

```
ccaaaacaac cctgacgggt attccttttg gtgaatggat gtccaaacgc ggtttgtcat    1380
atacagattt gaaaggacgt acggacgatt tacaggcagt ttccgtattc cctatggtta    1440
attctgtaga agagttggga ttggtgttga ggtggatgtt gtccgaaccc gaactggagg    1500
aaggaaagaa tatctggtta cgttccgaac attttctgc ggacgaaatt tcggcaggtg     1560
ccaatctgaa gcgtttgtat gcacaacgtg aagagttcag aaaaggaaac tggaaagcat    1620
tggccgttaa tcatgaaaaa agtgttttt atcaacttga tttggccgat gcagctgaag     1680
attttgtacg tcttggtttg gatatgcctg aattattgcc tgaggatgct ctgcagatgt    1740
cacgcatcca taaccggatg ttgcgtgcgc gtattttgaa attagacggg aaagattatc    1800
gtccggaaga acaggctgct tttgatttgc ttcgtgacgg cttgctggac gggatcagta    1860
atcgtaagag taccccaaaa ttggatgtat attccgatca gattgtttgg ggacgtagcc    1920
ccgtgcgcat cgatatggca ggtggatgga ccgatactcc tccttattca ctttattcgg    1980
gaggaaatgt ggtgaatcta gccattgagt tgaacggaca acctcccta caggtctatg     2040 tgaagccgtg taaagacttc catatcgtcc tgcgttctat cgatatgggt gctatggaaa    2100
tagtatctac gtttgatgaa ttgcaagatt ataagaagat cggttcacct ttctctattc    2160
cgaaagccgc tctgtcattg gcaggctttg cacctgcgtt ttctgctgta tcttatgctt    2220
cattagagga acagcttaaa gatttcggtg caggtattga agtgacttta ttggctgcta    2280
ttcctgccgg ttccggtttg ggcaccagtt ccattctggc ttctaccgta cttggtgcca    2340
ttaacgattt ctgtggttta gcctgggata aaaatgagat ttgtcaacgt actcttgttc    2400
ttgaacaatt gctgactacc ggaggtggat ggcaggatca gtatggaggt gtgttgcagg    2460
gtgtgaagct tcttcagacc gaggccggct ttgctcaaag tccattggtg cgttggctac    2520
ccgatcattt atttacgcat cctgaataca aagactgtca cttgctttat tataccggta    2580
taactcgtac ggcaaaaggg atcttggcag aaatagtcag ttccatgttc ctcaattcat    2640
cgttgcatct caatttactt tcggaaatga aggcgcatgc attggatatg aatgaagcta    2700
tacagcgtgg aagttttgtt gagtttggcc gtttggtagg aaaaacctgg gaacaaaaca    2760
aagcattgga tagcggaaca aatcctccgg ctgtggaggc aattatcgat ctgataaaag    2820
attataccct gggatataaa ttgccgggag ccggtggtgg cgggtactta tatatggtag    2880
cgaaagatcc gcaagctgct gttcgtattc gtaagatact gacagaaaac gctccgaatc    2940
cgcgggcacg ttttgtcgaa atgacgttat ctgataaggg attccaagta tcacgatcat    3000
aataccgttc gtataatgta tgctatacga agttatcgag ctctagagaa tgatcccctc    3060
attaggccac acgttcaagt gcagcgcaca ccgtggaaac ggatgaaggc acgaacccag    3120
ttgacataag cctgttcggt tcgtaaactg taatgcaagt agcgtatgcg ctcacgcaac    3180
tggtccagaa ccttgaccga acgcagcggt ggtaacggcg cagtggcggt tttcatggct    3240
tgttatgact gttttttgt acagtctatg cctcgggcat ccaagcagca agcgcgttac     3300
gccgtgggtc gatgtttgat gttatggagc agcaacgatg ttacgcagca gcaacgatgt    3360
tacgcagcag ggcagtcgcc ctaaaacaaa gttaggtggc tcaagtatgg gcatcattcg    3420
cacatgtagg ctcggccctg accaagtcaa atccatgcgg gctgctcttg atctttcgg    3480 tcgtgagttc ggagacgtag ccacctactc ccaacatcag ccggactccg attacctcgg    3540
gaacttgctc cgtagtaaga cattcatcgc gcttgctgcc ttcgaccaag aagcggttgt    3600
tggcgctctc gcggcttacg ttctgcccag gtttgagcag ccgcgtagtg agatctatat    3660
```

```
ctatgatctc gcagtctccg gcgagcaccg gaggcagggc attgccaccg cgctcatcaa    3720
tctcctcaag catgaggcca acgcgcttgg tgcttatgtg atctacgtgc aagcagatta    3780
cggtgacgat cccgcagtgg ctctctatac aaagttgggc atacgggaag aagtgatgca    3840
ctttgatatc gacccaagta ccgccaccta acaattcgtt caagccgaga tcgtagaatt    3900
tcgacgacct gcagccaagc ataacttcgt ataatgtatg ctatacgaac ggtag         3955

<210> SEQ ID NO 36
<211> LENGTH: 7061
<212> TYPE: DNA
<213> ORGANISM: Unknown
<220> FEATURE:
<223> OTHER INFORMATION: Transposon cassette.

<400> SEQUENCE: 36
ggccagatga ttaattccta attttgttg acactctatc attgatagag ttattttacc       60
actccctatc agtgatagag aaaagtgaaa tgaatagttc gacaaaaatc tagaaataat     120
tttgtttaac tttaagaagg agatatacaa tttcgtcgac acacaggaaa catattaaaa     180
attaaaacct gcaggagttt gaaggagata gaaccatggc gcagtcgaaa ctctatccag     240
ttgtgatggc aggtggctcc ggtagccgct tatggccgct ttcccgcgta ctttatccca     300
agcagttttt atgcctgaaa ggcgatctca ccatgctgca aaccaccatc tgccgcctga     360
acggcgtgga gtgcgaaagc ccggtggtga tttgcaatga gcagcaccgc tttattgtcg     420
cggaacagct gcgtcaactg aacaaactta ccgagaacat tattctcgaa ccggcagggc     480
gaaacacggc acctgccatt gcgctggcgg cgctggcggc aaaacgtcat agcccggaga     540
gcgacccgtt aatgctggta ttggcggcgg atcatgtgat tgccgatgaa gacgcgttcc     600
gtgccgccgt gcgtaatgcc atgccatatg ccgaagcggg caagctggtg accttcggca     660
ttgtgccgga tctaccagaa accggttatg ctatattcg tcgcggtgaa gtgtctgcgg     720
gtgagcagga tatggtggcc tttgaagtgg cgcagtttgt cgaaaaaccg aatctggaaa     780
ccgctcaggc ctatgtggca agcggcgaat attactggaa cagcggtatg ttcctgttcc     840
gcgccggacg ctatctcgaa gaactgaaaa aatatcgccc ggatatcctc gatgcctgtg     900
aaaaagcgat gagcgccgtc gatccggatc tcaatttat tcgcgtggat gaagaagcgt     960
ttctcgcctg cccggaagag tcggtggatt acgcggtcat ggaacgtacg gcagatgctg    1020
ttgtggtgcc gatggatgcg ggctggagcg atgttggctc ctggtcttca ttatgggaga    1080
tcagcgccca caccgccgag gcaacgtttt gccacggcga tgtgattaat cacaaaactg    1140
aaaacagcta tgtgtatgct gaatctggcc tggtcaccac cgtcggggtg aaagatctgg    1200
tagtggtgca gaccaaagat gcggtgctga ttgccgaccg taacgcgta caggatgtga    1260 aaaaagtggt cgagcagatc aaagccgatg tcgccatga gcatcgggtg catcgcgaag    1320
tgtatcgtcc gtggggcaaa tatgactcta tcgacgcggg cgaccgctac caggtgaaac    1380
gcatcaccgt gaaaccgggc gagggcttgt cggtacagat gcaccatcac gcgcggaac    1440 actgggtggt tgtcgcggga acggcaaaag tcaccattga tggtgatatc aaactgcttg    1500
gtgaaaacga gtccatttat attccgctgg ggcgacgca ttgcctggaa aacccggga    1560 aaattccgct cgatttaatt gaagtgcgct ccggctctta tctcgaagag gatgatgtgg    1620
tgcgtttcgc ggatcgctac ggacgggtgt aaacgtcgca tcaggcaatg aatgcgaaac    1680
cgcggtgtaa ataacgacaa aaataaaatt ggccgcttcg gtcagggcca actattgcct    1740
gaaaaagggt aacgatatga aaaattaac ctgctttaaa gcctatgata ttcgcgggaa    1800
```

```
attaggcgaa gaactgaatg aagatatcgc ctggcgcatt ggtcgcgcct atggcgaatt   1860
tctcaaaccg aaaaccattg tgttaggcgg tgatgtccgc ctcaccagcg aaaccttaaa   1920
actggcgctg gcgaaaggtt tacaggatgc gggcgttgac gtgctggata ttggtatgtc   1980
cggcaccgaa gagatctatt tcgccacgtt ccatctcggc gtggatggcg gcattgaagt   2040
taccgccagc cataatccga tggattataa cggcatgaag ctggttcgcg aggggctcg    2100
cccgatcagc ggagataccg gactgcgcga cgtccagcgt ctggctgaag ccaacgactt   2160
tcctcccgtc gatgaaacca acgcggtcg ctatcagcaa atcaacctgc gtgacgctta    2220
cgttgatcac ctgttcggtt atatcaatgt caaaaacctc acgccgctca agctggtgat   2280
caactccggg aacggcgcag cgggtccggt ggtggacgcc attgaagccc gctttaaagc   2340
cctcggcgcg cccgtggaat taatcaaagt gcacaacacg ccggacggca atttccccaa   2400
cggtattcct aacccactac tgccggaatg ccgcgacgac acccgcaatg cggtcatcaa   2460
acacggcgcg gatatgggca ttgcttttga tggcgatttt gaccgctgtt tcctgtttga   2520
cgaaaagggg cagtttattg agggctacta cattgtcggc ctgttggcag aagcattcct   2580
cgaaaaaaat cccggcgcga agatcatcca cgatccacgt ctctcctgga acaccgttga   2640
tgtggtgact gccgcaggtg gcacgccggt aatgtcgaaa accggacacg ccttattaa    2700
agaacgtatg cgcaaggaag acgccatcta tggtggcgaa atgagcgccc accattactt   2760
ccgtgatttc gcttactgcg acagcggcat gatcccgtgg ctgctggtcg ccgaactggt   2820
gtgcctgaaa gataaaacgc tgggcgaact ggtacgcgac cggatggcgg cgtttccggc   2880
aagcggtgag atcaacagca aactggcgca acccgttgag gcgattaacc gcgtggaaca   2940
gcattttagc cgtgaggcgc tggcggtgga tcgcaccgat ggcatcagca tgaccttgc    3000
cgactggcgc tttaacctgc gcacctccaa taccgaaccg gtggtgcgcc tgaatgtgga   3060
atcgcgcgt gatgtgccgc tgatggaagc gcgaacgcga actctgctga cgttgctgaa    3120
cgagtaaaaa cgcggccgcg atatcgttgt aaaacgacgg ccagtgcaag aatcataaaa   3180
aatttatttg ctttcaggaa aattttttctg tataatagat tcataaattt gagagaggag   3240
tttttgtgag cggataacaa ttccccatct tagtatatta gttaagtata aatacaccgc   3300
ggaggacgaa ggagatagaa ccatgtcaaa agtcgctctc atcaccggtg taaccggaca   3360
agacggttct tacctggcag agtttctgct ggaaaaaggt tacagaggtgc atggtattaa   3420
gcgtcgcgca tcgtcattca acaccgagcg cgtggatcac atttatcagg atccgcacac   3480
ctgcaacccg aaattccatc tgcattatgg cgacctgagt gatacctcta acctgacgcg   3540
cattttgcgt gaagtacagc cggatgaagt gtacaacctg ggcgcaatga gccacgttgc   3600
ggtctcttttt gagtcaccag aatataccgc tgacgtcgac gcgatgggta cgctgcgcct   3660
gctggaggcg atccgcttcc tcggtctgga aaagaaaact cgtttctatc aggcttccac   3720
ctctgaactg tatggtctgg tgcaggaaat tccgcagaaa gagaccacgc cgttctaccc   3780
gcgatctccg tatgcggtcg ccaaactgta cgcctactgg atcaccgtta actaccgtga   3840
atcctacggc atgtacgcct gtaacggaat tctcttcaac catgaatccc gcgccgcgg    3900
cgaaaccttc gttacccgca aaatcacccg cgcaatcgcc aacatcgccc aggggctgga   3960
gtcgtgcctg tacctcggca atatggatc cctgcgtgac tggggccacg ccaaagacta    4020
cgtaaaaatg cagtggatga tgctgcagca ggaacagccg gaagatttcg ttatcgcgac   4080
cggcgttcag tactccgtgc gtcagttcgt ggaaatggcg gcagcacagc tgggcatcaa   4140
```

```
actgcgcttt gaaggcacgg gcgttgaaga aagggcatt gtggtttccg tcaccgggca    4200
tgacgcgccg ggcgttaaac cgggtgatgt gattatcgct gttgacccgc gttacttccg    4260
tccggctgaa gttgaaacgc tgctcggcga cccgaccaaa gcgcacgaaa aactgggctg    4320
gaaaccggaa atcaccctca gagagatggt gtctgaaatg gtggctaatg acctcgaagc    4380
ggcgaaaaaa cactctctgc tgaaatctca cggctacgac gtggcgatcg cgctggagtc    4440
ataagcatga gtaaacaacg agttttatt gctggtcatc gcgggatggt cggttccgcc    4500
atcaggcggc agctcgaaca gcgcggtgat gtggaactgg tattacgcac ccgcgacgag    4560
ctgaacctgc tggacagccg cgccgtgcat gatttctttg ccagcgaacg tattgaccag    4620
gtctatctgg cggcggcgaa agtgggcggc attgttgcca caacaccta tccggcggat    4680
ttcatctacc agaacatgat gattgagagc aacatcattc acgccgcgca tcagaacgac    4740
gtgaacaaac tgctgtttct cggatcgtcc tgcatctacc cgaaactggc aaaacagccg    4800
atggcagaaa gcgagttgtt gcagggcacg ctggagccga ctaacgagcc ttatgctatt    4860
gccaaaatcg ccgggatcaa actgtgcgaa tcatacaacc gccagtacgg acgcgattac    4920
cgctcagtca tgccgaccaa cctgtacggg ccacacgaca acttccaccc gagtaattcg    4980
catgtgatcc cagcattgct gcgtcgcttc acgaggcga cggcacagaa tgcgccggac    5040
gtggtggtat gggcagcgg tacaccgatg cgcgaatttc tgcacgtcga tgatatggcg    5100
gcggcgagca ttcatgtcat ggagctggcg catgaagtct ggctggagaa cacccagccg    5160
atgttgtcgc acattaacgt cggcacgggc gttgactgca ctatccgcga gctggcgcaa    5220
accatcgcca aagtggtggg ttacaaaggc cgggtggttt tgatgccag caaaccggat    5280
ggcacgccgc gcaaactgct ggatgtgacg cgcctgcatc agcttggctg gtatcacgaa    5340
atctcactgg aagcgggct tgccagcact taccagtggt tccttgagaa tcaagaccgc    5400
tttcgggggg ggagctaacg cgccatttaa atcaacctca gcggtcatag ctgttccctg    5460
tgactgagca ataactagca taccccttg gggcctctaa acgggtcttg aggggtttt    5520
tgctgaaacc aatttgcctg cggcagtag cgcggtggtc ccacctgacc ccatgccgaa    5580
ctcagaagtg aaacgccgta gcgccgatgg tagtgtgggg tctccccatg cgagagtagg    5640
gaactgccag gcatcaaata aaacgaaagg ctcagtcgaa agactgggcc tttcgggatc    5700
caggccggcc tgttaacgaa ttaatcttcc gcggcgctga aaccaatttg cctggcggca    5760
gtagcgcggt ggtcccacct gacccatgc cgaactcaga agtgaaacgc cgtagcgccg    5820
atggtagtgt ggggtctccc catgcgagag tagggaactg ccaggcatca aataaaacga    5880
aaggctcagt cgaaagactg ggcctttcgg gatccaggcc ggcctgttaa cgaattaatc    5940
ttccgcggcg gtatcgataa gcttgatatc gaattccgaa gttcctattc tctagaaagt    6000
ataggaactt caggtctgaa gaggagttta cgtccagcca agctagcttg gctgcaggtc    6060
gtcgaaattc tacgatctcg gcttgaacga attgttaggt ggcggtactt gggtcgatat    6120
caaagtgcat cacttcttcc cgtatgccca actttgtata gagagccact gcgggatcgt    6180
caccgtaatc tgcttgcacg tagatcacat aagcaccaag cgcgttggcc tcatgcttga    6240
ggagattgat gagcgcggtg gcaatgccct gcctccggtg ctcgccggag actgcgagat    6300
catagatata gatctcacta cgcggctgct caaacctggg cagaacgtaa gccgcgagag    6360
cgccaacaac cgcttcttgg tcgaaggcag caagcgcgat gaatgtctta ctacggagca    6420
agttcccgag gtaatcggag tccggctgat gttgggagta ggtggctacg tctccgaact    6480
cacgaccgaa aagatcaaga gcagcccgca tggatttgac ttggtcaggg ccgagcctac    6540
```

```
atgtgcgaat gatgcccata cttgagccac ctaactttgt tttagggcga ctgccctgct   6600
gcgtaacatc gttgctgctg cgtaacatcg ttgctgctcc ataacatcaa acatcgaccc   6660
acggcgtaac gcgcttgctg cttggatgcc cgaggcatag actgtacaaa aaaacagtca   6720
taacaagcca tgaaaaccgc cactgcgccg ttaccaccgc tgcgttcggt caaggttctg   6780
gaccagttgc gtgagcgcat acgctacttg cattacagtt tacgaaccga acaggcttat   6840
gtcaactggg ttcgtgcctt catccgtttc cacggtgtgc gctgcacttg aacgtgtggc   6900
ctaatgaggg gatcaattct ctagagctcg ctgatcagaa gttcctattc tctagaaagt   6960
ataggaactt cgatggcgcc tcatccctga agccaatagg gataacaggg taatgatcgg   7020
atcccgggcc cgtcgactgc agaggcctgc atgcaagctt g   7061

<210> SEQ ID NO 37
<211> LENGTH: 4187
<212> TYPE: DNA
<213> ORGANISM: Unknown
<220> FEATURE:
<223> OTHER INFORMATION: Transposon.

<400> SEQUENCE: 37
cacaggttgg ctgataagtc cccggtctag cttgcatgca gattgcagca ttacacgtct     60
tgagcgattg tgtaggctgg agctgctcaa gcccgtcagg gcgcgtcagc gggtgttggc    120
gggtgtcggg gctggcttaa ctatgcggca tcagagcaga ttgtactgag agtgcaccat    180
atgcggtgtg aaataccgca cagatgcgta aggagaaaat accgcatcag gcgccattcg    240
ccattcaggc tgcgcaactg ttgggaaggg cgatcggtgc gggcctcttc gctattacgc    300
cagctggcga aagggggatg tgctgcaagg cgattaagtt gggtaacgcc agggttttcc    360
cagtcacgac gttgtaaaac gacggccagt gaattcgagc tcggtacctc gcgaatgcat    420
ctagattgta aaacgacggc cagtgaattc ccttagggat aacagggtaa ttacggcccc    480
aaggtccaaa cggtgaaggt accgggcccc ccctcgaggt cgaggtaccc aaatatgcat    540
aatcgaaatt aatacgactc actatagggg aattgattct ggtaccaaat gagtcgaccg    600
gccagatgat taattcctaa ttttttgttga cactctatca ttgatagagt tattttacca    660
ctccctatca gtgatagaga aaagtgaaat gaatagttcg acaaaaatct agaataatt    720 tgtttaact ttaagaagga gatatacaat ttcgtcgaca cacaggaaac atattaaaaa    780
ttaaaacctg caggagttta aacgcggccg cgatatcgtt gtaaaacgac ggccagtgca    840
agaatcataa aaaatttatt tgctttcagg aaaattttc tgtataatag attcataaat    900
ttgagagagg agttttttgtg agcggataac aattccccat cttagtatat tagttaagta    960
taaatacacc gcggaggcgt cgaaggagat acaaccatgc aaaaccacgt tatcagctta   1020
gcttccgccg cagaacgcag ggcgcacatt gccgatacct tcggcaggca cggcatcccg   1080
tttcagtttt tcgacgcact gatgccgtct gaaaggctgg aacaggcaat ggcggaactc   1140
gtccccggct tgtcggcgca cccctatttg agcggagtgg aaaaagcctg ctttatgagc   1200
cacgccgtat tgtggaagca ggcattggac gaaggtctgc cgtatatcac cgtatttgag   1260
gacgacgttt tactcggcga aggtgcggaa aaattccttg ccgaagacgc ttggctgcaa   1320
gaacgctttg accccggatac cgcctttatc gtccgcttgg aaacgatgtt tatgcacgtc   1380
ctgacctcgc cctccggcgt ggcggattac tgcgggcgcg cctttccgct gttgaaagc   1440 gaacactggg ggacggcggg ctatatcatt tcccgaaaag cgatgcggtt tttcctggac   1500
```

```
aggtttgccg ccctgccgcc cgaagggctg caccccgtcg atctgatgat gttcagcgat   1560
tttttcgaca gggaaggaat gccggtttgc cagctcaatc ccgccttgtg cgcccaagag   1620
ctgcattatg ccaagtttca cgaccaaaac agcgcattgg gcagcctgat cgaacacgac   1680
cgcctcctga accgcaaaca gcaaaggcgc gattcccccg ccaacacatt caaacaccgc   1740
ctgatccgcg ccttgaccga tatcagcagg gaaagggaaa aacgccggca aaggcgcgaa   1800
cagttcattg tgccttttcca ataacgccat ttaaatcaac ctcagcggtc atagctgttt   1860
cctgtgactg agcataaact agcataaccc cttggggcct ctaaacgggt cttgaggggt   1920
tttttgctga aaccaatttg cctggcggca gtagcgcggt ggtcccacct gaccccatgc   1980
cgaactcaga agtgaaacgc cgtagcgccg atggtagtgt ggggtctccc catgcgagag   2040
tagggaactg ccaggcatca aataaaacga aaggctcagt cgaaagactg gcctttcgg   2100 gatccaggcc ggcctgttaa cgaattaatc ttccgcggcg gtatcgataa gcttgatatc   2160
gacactacca tcatgtatga atatcctcct tagttcctat tccgaagttc ctattctcta   2220
gaaagtatag gaacttcggc gacgtctaag aaaccattat tatcatgaca ttaacctata   2280
aaaataggcg tatcacgagg ccctttcgtc ttcaagaatt ctcatgtttg acagcttatc   2340
atcgataagc tttaatgcgg tagtttatca cagttaaatt gctaacgcag tcaggcaccg   2400
tgtatgaaat ctaacaatgc gctcatcgtc atcctcggca ccgtcaccct ggatgctgta   2460
ggcataggct tggttatgcc ggtactgccg ggcctcttgc gggatatcgt ccattccgac   2520
agcatcgcca gtcactatgg cgtgctgcta gcgctatatg cgttgatgca atttctatgc   2580
gcacccgttc tcggagcact gtccgaccgc tttggccgcc gcccagtcct gctcgcttcg   2640
ctacttggag ccactatcga ctacgcgatc atggcgacca cacccgtcct gtggatcctc   2700
tacgccggac gcatcgtggc cggcatcacc ggcgccacag gtgcggttgc tggcgcctat   2760
atcgccgaca tcaccgatgg ggaagatcgg gctcgccact cgggctcat gagcgcttgt   2820 ttcggcgtgg gtatggtggc aggccccgtg gccggggggac tgttgggcgc catctccttg   2880
catgcaccat tccttgcggc ggcggtgctc aacggcctca acctactact gggctgcttc   2940
ctaatgcagg agtcgcataa gggagagcgt cgaccgatgc ccttgagagc cttcaaccca   3000
gtcagctcct tccggtgggc gcggggcatg actatcgtcg ccgcacttat gactgtcttc   3060
tttatcatgc aactcgtagg acaggtgccg cagcgctct gggtcatttt cggcgaggac   3120
cgctttcgct ggagcgcgac gatgatcggc ctgtcgcttg cggtattcgg aatcttgcac   3180
gccctcgctc aagccttcgt cactggtccc gccaccaaac gtttcggcga aagcaggcc   3240 attatcgccg gcatggcggc cgacgcgctg ggctacgtct tgctggcgtt cgcgacgcga   3300
ggctggatgg ccttccccat tatgattctt ctcgcttccg gcggcatcgg gatgcccgcg   3360
ttgcaggcca tgctgtccag gcaggtagat gacgaccatc agggacagct tcaaggatcg   3420
ctcgcggctc ttaccagcct aacttcgatc attggaccgc tgatcgtcac ggcgatttat   3480
gccgcctcgg cgagcacatg gaacgggttg gcatggattg taggcgccgc cctataccttt   3540 gtctgcctcc ccgcgttgcg tcgcggtgca tggagccggg ccacctcgac ctgagtggca   3600 gggcggggc taaggcgcgc catttaaatg aagttcctat tccgaagttc ctattctcta   3660
gaaagtatag gaacttcgaa gcagctccag cctacacaat cgctcaagac gtgtaatgct   3720
gcaatctgca tgcaagcttg gcactgggat ggcgcctcat ccctgaagcc aatagggata   3780
acagggtaat aagcttggcg taatcatgtc atgatcggat cccgggcccg tcgactgcag   3840
aggcctgcat gcaagcttgg cgtaatcatg gtcatagctg tttcctgtgt gaaattgtta   3900
```

| | |
|---|---|
| tccgctcaca attccacaca acatacgagc cggaagcata aagtgtaaag cctggggtgc | 3960 |
| ctaatgagtg agctaactca cattaattgc gttgcgctca ctgcccgctt tccagtcggg | 4020 |
| aaacctgtcg tgccagctgc attaatgaat cggccaacgc gcggggagag gcggtttgcg | 4080 |
| tattgggcgc tcttccgctt cctcgccaac aaaaattagg aattaatcat ctggccaatt | 4140 |
| tcaggtggca cttttcgggc agaccgggga cttatcagcc aacctgt | 4187 |

<210> SEQ ID NO 38
<211> LENGTH: 5011
<212> TYPE: DNA
<213> ORGANISM: Unknown
<220> FEATURE:
<223> OTHER INFORMATION: Transposon

<400> SEQUENCE: 38

| | |
|---|---|
| acaggttggc tgataagtcc ccggtctgcc cgaaaagtgc cacctgaaat tggccagatg | 60 |
| attaattcct aattttttgtt gattctggta ccaaatgagt cgaccggcca gatgattaat | 120 |
| tcctaatttt tgttgacact ctatcattga tagagttatt ttaccactcc ctatcagtga | 180 |
| tagagaaaag tgaaatgaat agttcgacaa aaatctagaa ataattttgt ttaactttaa | 240 |
| gaaggagata tacaaatgaa atcgaagaa ggtaaactgg taatctggat taacggcgat | 300 |
| aaaggctata acggtctcgc tgaagtcggt aagaaattcg agaagatac cggaattaaa | 360 |
| gtcaccgttg agcatccgga taaactggaa gagaaattcc cacaggttgc ggcaactggc | 420 |
| gatggccctg acattatctt ctgggcacac gaccgctttg gtggctacgc tcaatctggc | 480 |
| ctgttggctg aaatcacccc ggacaaagcg ttccaggaca gctgtatcc gtttacctgg | 540 |
| gatgccgtac gttacaacgg caagctgatt gcttacccga tcgctgttga agcgttatcg | 600 |
| ctgatttata caaagatct gctgccgaac ccgccaaaaa cctgggaaga gatcccggcg | 660 |
| ctggataaag aactgaaagc gaaggtaag agcgcgctga tgttcaacct gcaagaaccg | 720 |
| tacttcacct ggccgctgat tgctgctgac ggggggttatg cgttcaagta tgaaaacggc | 780 |
| aagtacgaca ttaaagacgt gggcgtggat aacgctggcg cgaaagcggg tctgacctt c | 840 |
| ctggttgacc tgattaaaaa caaacacatg aatgcagaca ccgattactc catcgcagaa | 900 |
| gctgccttta taaaggcga aacagcgatg accatcaacg gcccgtgggc atggtccaac | 960 |
| atcgacacca gcaaagtgaa ttatggtgta acggtactgc cgaccttcaa gggtcaacca | 1020 |
| tccaaaccgt tcgttggcgt gctgagcgca ggtattaacg ccgccagtcc gaacaaagag | 1080 |
| ctggcaaaag agttcctcga aaactatctg ctgactgatg aaggtctgga agcggttaat | 1140 |
| aaagacaaac cgctgggtgc cgtagcgctg aagtcttacg aggaagagtt ggcgaaagat | 1200 |
| ccacgtattg ccgccactat ggaaaacgcc cagaaaggtg aaatcatgcc gaacatcccg | 1260 |
| cagatgtccg cttttctggta tgccgtgcgt actgcggtga tcaacgccgc cagcggtcgt | 1320 |
| cagactgtcg atgaagccct gaaagacgcg cagactatgc acttcattga aaacaaaaac | 1380 |
| ttcgtcatct ccattccgac cgcagacaaa cgccgtaatc acatcatcca acagttcggc | 1440 |
| caaaagaaaa ttccgtttga atttttcgat gccttcaccc cgagcgaacg tctgaacgac | 1500 |
| catctgcagc gctatctgcc gaatgtcgca gcaaccccgc gtctgacgat gggtgaaaaa | 1560 |
| ggttgcctga tgtctcactt tatgctgtgg aaaaatgtg ttgatgacgg cctggattac | 1620 |
| attaccctgt ttgaagatga catcctgctg ggtgaaaacg cggaacaatt cctggccgaa | 1680 |
| gacgaatggc tgaaagtgcg ttttaatttc caggaaatct ttgttctgcg cctggaaacc | 1740 |

```
ttcctgatgc cggtgaaaat tgaaaaacag caaggcatcc tgccgtttca gcaacgcgaa    1800
atcgatatcc tgaaatcaaa acatttcggc acggcaggtt atgttatttc gcacggtgca    1860
gctaaatacc tgatcgaagt cttcgaaaaa ttcagctctg aagaagtgaa accgattgat    1920
gaaatcatgt taaccagct gattgacatc tccggctatc aggtttacca actgaatccg     1980
gctatttgcg tccaggaact gcaactgaac caggaaaata gtgtgctgga atccggtctg    2040
cagaaagagc gtaagaaaaa caccgttagc cataccaaga aaaccctgaa atatcgtctg    2100
acgcgcatga agaaaaacat cctgcgcgca ctgaataaaa agaaatggga agaacgccaa    2160
tacatcaaag gtctgcaagg caaaaatatc atcctgttta tctagtttcg tcgacacaca    2220
ggaaacatat taaaaattaa acctgcagg agtttaaacg cggccgcgat atcgttgtaa     2280
aacgacggcc agtgcaagaa tcataaaaaa tttatttgct ttcaggaaaa ttttctgta     2340 taatagattc ataaatttga gagaggagtt tttgtgagcg ataacaatt ccccatctta     2400 gtatattagt taagtataaa tacaccgcgg aggcgtcgaa ggagatacaa ccatgagagt    2460
tctggttacc ggtggtagcg gttacattgg aagtcatacc tgtgtgcaat tactgcaaaa    2520
cggtcatgat gtcatcattc ttgataacct ctgtaacagt aagcgcagcg tactgcctgt    2580
tatcgagcgt ttaggcggca acatccaac gttttgttgaa ggcgatattc gtaacgaagc    2640
gttgatgacc gagatcctgc acgatacgc tatcgacacc gtgatccact tcgccgggct    2700
gaaagccgtg ggcgaatcgg tacaaaaacc gctggaatat tacgacaaca atgtcaacgg    2760
cactctgcgc ctgattagcg ccatgcgcgc cgctaacgtc aaaaacttta tttttagctc    2820
ctccgccacc gtttatggcg atcagcccaa aattccatac gttgaaagct ccccgaccgg    2880
cacaccgcaa agcccttacg gcaaaagcaa gctgatggtg aacagatcc tcaccgatct     2940 gcaaaaagcc cagccggact ggagcattgc cctgctgcgc tacttcaacc cggttggcgc    3000
gcatccgtcg ggcgatatgg gcgaagatcc gcaaggcatt ccgaataacc tgatgccata    3060
catcgcccag gttgctgtag gccgtcgcga ctcgctggcg attttggta acgattatcc     3120 gaccgaagat ggtactggcg tacgcgatta catccacgta atggatctgg cggacggtca    3180
cgtcgtggca atggaaaaac tggcgaacaa gccaggcgta cacatctaca acctcggcgc    3240
tggcgtaggc aacagcgtgc tggacgtggt taatgccttc agcaaagcct gcggcaaacc    3300
ggttaattat cattttgcac cgcgtcgcga gggcgacctt ccggcctact gggcggacgc    3360
cagcaaagcc gaccgtgaac tgaactggcg cgtaacgcgc acactcgatg aaatggcgca    3420
ggacacctgg cactggcagt cacgccatcc acagggatat cccgattaac gccatttaaa    3480
tcaacctcag cggtcatagc tgtttcctgt gactgagcaa taactagcat aaccccttgg    3540
ggcctctaaa cgggtcttga ggggttttttt gctgaaacca atttgcctgg cggcagtagc    3600
gcggtggtcc cacctgaccc catgccgaac tcagaagtga acgccgtag cgccgatggt     3660 agtgtggggt ctccccatgc gagagtaggg aactgccagg catcaaataa acgaaaggc     3720 tcagtcgaaa gactgggcct ttcgggatcc aggccggcct gttaacgaat taatcttccg    3780
cggcggtatc gataagcttg atatcgaggc tgacatggga attagccatg gtccatatga    3840
atatcctcct tagttcctat tccgaagttc ctattctcta aaagtatag gaacttcggc     3900 gcgcctacct gtgacggaag atcacttcgc agaataaata aatcctggtg tccctgttga    3960
taccgggaag ccctgggcca acttttggcg aaaatgagac gttgatcggc acgtaagagg    4020
ttccaacttt caccataatg aaataagatc actaccgggc gtattttttg agttgtcgag    4080
attttcagga gctaaggaag ctaaaatgga gaaaaaaatc actggatata ccaccgttga    4140
```

```
tatatcccaa tggcatcgta aagaacattt tgaggcattt cagtcagttg ctcaatgtac    4200
ctataaccag accgttcagc tggatattac ggccttttta aagaccgtaa agaaaaataa    4260
gcacaagttt tatccggcct ttattcacat tcttgcccgc ctgatgaatg ctcatccgga    4320
attacgtatg gcaatgaaag acggtgagct ggtgatatgg gatagtgttc acccttgtta    4380
caccgttttc catgagcaaa ctgaaacgtt tcatcgctc tggagtgaat accacgacga    4440
tttccggcag tttctacaca tatattcgca agatgtggcg tgttacggtg aaaacctggc    4500
ctatttccct aaagggttta ttgagaatat gttttcgtc tcagccaatc cctgggtgag    4560
tttcaccagt tttgatttaa acgtggccaa tatggacaac ttcttcgccc ccgttttcac    4620
catgggcaaa tattatacgc aaggcgacaa ggtgctgatg ccgctggcga ttcaggttca    4680
tcatgccgtt tgtgatggct tccatgtcgg cagatgctta atgaatacaa cagtactgcg    4740
atgagtggca gggcggggcg taaggcgcgc catttaaatg aagttcctat tccgaagttc    4800
ctattctcta gaaagtatag gaacttcgaa gcagctccag cctacacaat cgctcaagac    4860
gtgtaatgct gcaatctgca tgcaagcttg gcactggcga tggcgcctca tccctgaagc    4920
caataagcag ctccagccta cacaatcgct caagacgtgt aatgctgcaa tctgcatgca    4980
agctagaccg gggacttatc agccaacctg t                                   5011
```

<210> SEQ ID NO 39
<211> LENGTH: 2984
<212> TYPE: DNA
<213> ORGANISM: Unknown
<220> FEATURE:
<223> OTHER INFORMATION: Transposon.

<400> SEQUENCE: 39

```
tggccagatg attaattcct aattttttgtt gacactctat cattgataga gttatttttac   60 cactccctat cagtgataga gaaaagtgaa atgaatagtt cgacaaaaat ctagaaataa    120
ttttgtttaa ctttaagaag gagatataca agagctcgag tcgaaggaga tagaaccatg    180
ggaaacacat caatacaaac gcagagttac cgtgcggtag ataaagatgc agggcaaagc    240
agaagttaca ttattccatt cgcgctgctg tgctcactgt ttttttctttg ggcggtagcc    300 ataaccctta acgacatttt attacctcaa ttccagcagg cttttacgct gacaaatttc    360
caggctggcc tgatccaatc ggcctttttac tttggttatt tcattatccc aatccctgct    420
gggatattga tgaaaaaact cagttataaa gcagggatta ttaccgggtt atttttatat    480
gccttgggtg ctgcattatt ctggcccgcc gcagaaataa tgaactacac cttgttttta    540
gttggcctat ttattattgc agccggatta ggttgtctgg aaactgccgc aaacccttt     600 gttacggtat tagggccgga aagtagtggt cacttccgct taaatcttgc gcaaacattt    660
aactcgtttg gcgcaattat cgcggttgtc tttgggcaaa gtcttatttt gtctaacgtg    720
ccacatcaat cgcaagacgt tctcgataaa atgtctccag agcaattgag tgcgtataaa    780
cacagcctgg tattatcggt acagacacct tatatgatca tcgtggctat cgtgttactg    840
gtcgccctgc tgatcatgct gacgaaattc ccggcattgc agagtgataa tcacagtgac    900
gccaaacaag gatcgttctc cgcatcgctt tctcgcctgg cgcgtattcg ccactggcgc    960
tgggcggtat tagcgcaatt ctgctatgtc ggcgcacaaa cggcctgctg gagctatttg    1020
attcgctacg ctgtagaaga aattccaggt atgactgcag gctttgccgc taactatta    1080 accggaacca tggtgtgctt ctttattggt cgtttcaccg gtacctggct catcagtcgc    1140
```

| | |
|---|---|
| ttcgcaccac acaaagtcct ggccgcctac gcattaatcg ctatggcact gtgcctgatc | 1200 |
| tcagccttcg ctggcggtca tgtgggctta atagccctga cttatgcag cgcctttatg | 1260 |
| tcgattcagt acccaacaat cttctcgctg gcattaaga atctcggcca ggacaccaaa | 1320 |
| tatggttcgt ccttcatcgt tatgaccatt attggcggcg gtattgtcac tccggtcatg | 1380 |
| ggttttgtca gtgacgcggc gggcaacatc cccactgctg aactgatccc cgcactctgc | 1440 |
| ttcgcggtca tctttatctt tgcccgtttc cgttctcaaa cggcaactaa ctgataaatc | 1500 |
| gatactagca taaccccttg gggcctctaa acgcgtcgac acgcaaaaag gccatccgtc | 1560 |
| aggatggcct tctgcttaat ttgatgcctg gcagtttatg gcgggcgtcc tgcccgccac | 1620 |
| cctccgggcc gttgcttcgc aacgttcaaa tccgctcccg gcggatttgt cctactcagg | 1680 |
| agagcgttca ccgacaaaca acagataaaa cgaaaggccc agtctttcga ctgagccttt | 1740 |
| cgttttatt gatgcctggc agttccctac tctcgcatgg ggagaccca cactaccatc | 1800 |
| ggatccaggc cggcctgtta acgaattaat cttccgcggc ggtatcgata agcttgatgg | 1860 |
| cgaaagggg atgtgctgca aggcgattaa gttgggtaac gccagggttt tcccagtcac | 1920 |
| gacgttgtaa aacgacggcc agtgaattcg agctcggtac ctaccgttcg tataatgtat | 1980 |
| gctatacgaa gttatcgagc tctagagaat gatccctaaa tgcttcaata atattgaaaa | 2040 |
| aggaagagta tgagggaagc ggtgatcgcc gaagtatcga ctcaactatc agaggtagtt | 2100 |
| ggcgtcatcg agcgccatct cgaaccgacg ttgctggccg tacatttgta cggctccgca | 2160 |
| gtggatggcg gcctgaagcc acacagtgat attgatttgc tggttacggt gaccgtaagg | 2220 |
| cttgatgaaa caacgcggcg agctttgatc aacgaccttt tggaaacttc ggcttcccct | 2280 |
| ggagagagcg agattctccg cgctgtagaa gtcaccattg ttgtgcacga cgacatcatt | 2340 |
| ccgtggcgtt atccagctaa gcgcgaactg caatttggag aatggcagcg caatgacatt | 2400 |
| cttgcaggta tcttcgagcc agccacgatc gacattgatc tggctatctt gctgacaaaa | 2460 |
| gcaagagaac atagcgttgc cttggtaggt ccagcggcgg aggaactctt tgatccggtt | 2520 |
| cctgaacagg atctatttga ggcgctaaat gaaaccttaa cgctatggaa ctcgccgccc | 2580 |
| gactgggctg gcgatgagcg aaatgtagtg cttacgttgt cccgcatttg gtacagcgca | 2640 |
| gtaaccggca aaatcgcgcc gaaggatgtc gctgccgact gggcaatgga gcgcctgccg | 2700 |
| gcccagtatc agcccgtcat acttgaagct agacaggctt atcttggaca agaagaagat | 2760 |
| cgcttggcct cgcgcgcaga tcagttggaa gaatttgtcc actacgtgaa aggcgagatc | 2820 |
| accaaggtag tcggcaaata atagcgggac tctgggaatt cgacgacct gcagccaagc | 2880 |
| ataacttcgt ataatgtatg ctatacgaac ggtaggatcc tctagagtcg acctgcaggc | 2940 |
| atgcaagctt ggcgtaatca tggtcatagc tgtttcctgt gtga | 2984 |

<210> SEQ ID NO 40
<211> LENGTH: 4259
<212> TYPE: DNA
<213> ORGANISM: Unknown
<220> FEATURE:
<223> OTHER INFORMATION: GalETKM operon comprising 19 bp mosaic end recognition site for the EZ-Tn5 transposase at its 5' end.

<400> SEQUENCE: 40

| | |
|---|---|
| ttactcagca ataaactgat attccgtcag gctggaatac tcttcgccag gacgcaggaa | 60 |
| gcagtccggt tgcggccatt cagggtggtt cgggctgtcc ggtagaaact cgcttttccag | 120 |
| agccagccct tgccagtcgg cgtaaggttc ggttccccgc gacggtgtgc cgccgaggaa | 180 |

```
gttgccggag tagaattgca gagccggagc ggtggtgtag accttcagct gcaattttc      240 atctgctgac cagacatgcg ccgccacttt cttgccatcg cctttggcct gtaacaagaa     300
tgcgtgatcg taacctttca cttttgcgctg atcgtcgtcg gcaagaaact cactggcgat    360
gattttggcg ctgcggaaat caaaagacgt tccggcgaca gatttcaggc cgtcgtgcgg     420
aatgccgcct tcatcaaccg gcagatattc gtccgccaga atctgcaact tgtgattgcg    480
cacgtcagac tgctcgccgt caagattgaa atagacgtga ttagtcatat tcaccgggca    540
aggtttatca actgtggcgc gataagtaat ggagatacgg ttatcgtcgg tcagacgata    600
ttgcaccgtc gcgccgagat tacccgggaa gccctgatca ccatcatctg aactcagggc    660
aaacagcacc tgacgatcgt tctggttcac aatctgccag cgacgtttgt cgaacccttc    720
cggcccgccg tgcagctggt taacgccctg acttggcgaa agcgtcacgg tttcaccgtc    780
aaaggtataa cggctattgg cgatacggtt ggcataacga ccaatagagg cccccagaaa    840
cgcggcctga tcctgatagc attccggget ggcacagccg agcagcgcct cgcggacgct    900
gccatcggaa agcggaatac gggcggaaag taaagtcgca ccccagtcca tcagcgtgac    960
taccatccct gcgttgttac gcaaagttaa cagtcggtac ggctgaccat cgggtgccag    1020
tgcgggagtt tcgttcagca ctgtcctgct ccttgtgatg gtttacaaac gtaaaaagtc    1080
tctttaatac ctgttttgc ttcatattgt tcagcgacag cttgctgtac ggcaggcacc    1140
agctcttccg ggatcagcgc gacgatacag ccgccaaatc cgccgccggt catgcgtacg    1200
ccacctttgt cgccaatcac agctttgacg atttctacca gagtgtcaat ttgcggcacg    1260
gtgatttcga atcatcgcg catagaggca tgagactccg ccatcaactc gcccatacgt    1320
ttcaggtcgc cttgctccag cgcgctggca gcttcaacgg tgcgggcgtt ttcagtcagt    1380
atatgacgca cgcgttttgc cacgatcggg tccagttcat gcgcaacagc gttgaactct    1440
tcaatggtga catcacgcag ggctggctgc tggaagaaac gcgcaccggt ttcgcactgt    1500
tcacgacggg tgttgtattc gctgccaacc agggtacgtt tgaagttact gttgatgatg    1560
acgacagcca cacctttggg catggaaact gctttggtcc ccagtgagcg gcaatcgatc    1620
agcaaggcat gatctttctt gccgagcgcg gaaattagct gatccatgat cccgcagtta    1680
cagcctacaa actggttttc tgcttcctga ccgttaagcg cgatttgtgc gccgtccagc    1740
ggcagatgat aaagctgctg caatacggtt ccgaccgcga cttccagtga gcggaagaa    1800 cttaacccgg caccctgcgg cacattgccg ctgatcacca tgtccacgcc gccgaagctg    1860
ttgttacgca gttgcagatg tttcaccacg ccacgaacgt agttagccca ttgatagttt    1920
tcatgtgcga caatgggcgc atcgagggaa aactcgtcga gctgattttc ataatcggct    1980
gccatcacgc gaactttacg gtcatcgcgt ggtgcacaac tgatcacggt ttgataatca    2040
atcgcgcagg gcagaacgaa accgtcgttg tagtcggtgt gttcaccaat caaattcacg    2100
cggccaggcg cctgaatggt gtgagtggca gggtagccaa atgcgttggc aaacagagat    2160
tgtgtttttt ctttcagact catttcttac actccggatt cgcgaaaatg gatatcgctg    2220
actgcgcgca aacgctctgc tgcctgttct gcggtcaggt ctcgctgggt ctctgccagc    2280
atttcataac caaccataaa tttacgtacg gtggcggagc gcagcagagg cggataaaag    2340
tgcgcgtgca gctgccagtg ttgattctct tcgccattaa atggcgcgcc gtgccagccc    2400
atagagtagg ggaaggagca ctggaagagg ttgtcataac gactggtcag cttttttcaac    2460 gccagcgcca gatcgctgcg ctgggcgtcg gtcaaatcgg tgatccgtaa aacgtgggct    2520
ttgggcagca gtagcgtttc gaacggccag gcagcccagt aaggcacgac ggctaaccag    2580
```

```
tgttcggttt cgacaacggt acggctaccg tctgccagct cgcgctgaac ataatccacc    2640
agcattggtg atttctgttc ggcaaaatat tcttttttgca ggcggtcttc gcgctcagct   2700
tcgttaggca ggaagctatt tgcccaaatc tgaccgtgcg gatgcgggtt agagcagccc   2760
atcgccgcgc ctttgttttc aaaaacctgc acccatgggt acgttttccc cagttctgcg   2820
gtttgctcct gccaggtttt gacgatttcc gtcaatgctg caacgctgag ctctggcagc   2880
gttttactgt gatccggtga aaagcagatc acccggctgg tgccgcgcgc gctctggcaa   2940
cgcatcagcg gatcgtgact ttctggcgca tctggcgtgt cagacatcaa agccgcaaag   3000
tcattagtga aaacgtaagt cccggtgtaa tcggggtttt tatcgcctgt cacccgcaca   3060
ttacctgcgc agaggaagca atctggatcg tgcgcaggta acacctgttt ggctggcgtt   3120
tcctgcgccc cctgccaggg gcgcttagcg cggtgcggtg aaaccagaat ccattgcccg   3180
gtgagcgggt tgtagcggcg atgtggatga tcaacgggat taaattgcgt catggtcgtt   3240
ccttaatcgg gatatccctg tggatggcgt gactgccagt gccaggtgtc ctgcgccatt   3300
tcatcgagtg tgcgcgttac gcgccagttc agttcacggt cggctttgct ggcgtccgcc   3360
cagtaggccg gaaggtcgcc ctcgcgacgc ggtgcaaaat gataattaac cggtttgccg   3420
caggctttgc tgaaggcatt aaccacgtcc agcacgctgt tgcctacgcc agcgccgagg   3480
ttgtagatgt gtacgcctgg cttgttcgcc agttttttcca tcgccacgac gtgaccgtcc   3540
gccagatcca ttacgtggat gtaatcgcgt acgccagtac catcttcggt cggataatcg   3600
ttaccaaaaa tcgccagcga gtcgcgacgg cctacagcaa cctgggcgat gtatggcatc   3660
aggttattcg gaatgccttg cggatcttcg cccatatcgc ccgacggatg cgcgccaacc   3720
gggttgaagt agcgcagcag ggcaatgctc cagtccggct gggcttttttg cagatcggtg   3780 aggatctgtt ccaccatcag cttgcttttg ccgtaagggc tttgcggtgt gccggtcggg   3840
aagctttcaa cgtatggaat tttgggctga tcgccataaa cggtggcgga ggagctaaaa   3900
ataaagtttt tgacgttagc ggcgcgcatg gcgctaatca ggcgcagagt gccgttgaca   3960
ttgttgtcgt aatattccag cggttttttgt accgattcgc ccacggcttt cagcccggcg   4020
aagtggatca cggtgtcgat agcgtgatcg tgcaggatct cggtcatcaa cgcttcgtta   4080
cgaatatcgc cttcaacaaa cgttggatgt ttgccgccta aacgctcgat aacaggcagt   4140
acgctgcgct tactgttaca gaggttatca agaatgatga catcatgacc gttttgcagt   4200
aattgcacac aggtatgact tccaatgtaa ccgctaccac cggtaaccag aactctcat   4259
```

<210> SEQ ID NO 41
<211> LENGTH: 6021
<212> TYPE: DNA
<213> ORGANISM: Unknown
<220> FEATURE:
<223> OTHER INFORMATION: Expression construct comprising Bbhl gene with codon optimization for E. coli under control of Ptet promoter and conferring zeocin resistance.

<400> SEQUENCE: 41

```
tttcccccgaa aagtgccacc tgaaattggc cagatgatta attcctaatt tttgttgaca     60
ctctatcatt gatagagtta ttttaccact ccctatcagt gatagagaaa agtgaaatga    120
atagttcgac aaaaatctag aaataatttt gtttaacttt aagaaggaga tatacaaatg    180
agcgatgata acctggccct gaaccagacc gtgaccgcaa gcagctatga agtggcaacg    240
accgcaccgg aaaaagccgt ggatggcgat ctgggtacgc gttggggtac cgcccagaac    300
```

```
aaagcggcca atgaatggat tgaagtcggc ctgggcggta ccaaaacggt gaaacagatc    360
aacatcgatt tcgaacgtaa agacgcggat caaaatatca ccagcttcaa agttgaactg    420
aaacagggtg acacctatac gaaagtgtac caaaaagata cccgcgccaa acagcaagaa    480
attatcctgc tggatcaggc acagcaagca agtgctgtta aagtcacggt gctgtccgcc    540
gatggcggta ccatgaactg ggttaatgtc ggtattaacg aaatctccgt ttattcagcc    600
ccgaaagaaa ccgtcctgga caccgcagat acgaaccata tgctgggcgc taccatgacg    660
gcgagctcta atgaaaccgc tacgctgacc ccggacaaag cgattgatca gaaccgtacc    720
ggtcgcaaca atcgttgggc gagtggctat gaaaccccgt ccaatatctg gctgaaagcc    780
gaatttccgc gtctgaccgc agtgaaagac attcgtatct atttctttga acgcgatgtc    840
aacccgaaac cgacgaatgt gcagtcgttc gacctgagct acaccgattc tgaaggtacc    900
gaacacacgc tgaaaagcgg ctatgccatg accgcatctg gcgctggtta cgttgccgac    960
gtggttattc aactggatca ggcggtgaac gcccgcagtc tgaaactgtc caacttcgca   1020
atcaaaagtt ccgaatacaa caatgtgtca gttgccgaat gggaagcata ctcgaacgat   1080
caggctgaac cgggtgcaac cctggactcg gtcgtgagcg atctggaaag caatcatctg   1140
accattgaaa cggacaccga tacgctggca ctgccgacgg tgccggatgg ttataccgtt   1200
aaatttaacg gcgcagacta cgaacagctg atcgcagctg atggtacggt gaatcacccg   1260
ctggttgaca aaaccgtcca ggtggcttat gttgtcaccg atacggcgac cggcaacacc   1320
aaaaccacga gcgacattcc gtacgtggtt aaaggtacca atcagcaaca ggaaggcaac   1380
aatgctaaac gacgattat cccggaaatc gcggaatggc attctaccag tgcggccaaa   1440
ctggcagctt cagcggtgac caaagtcgtg tatgatgacg attcgctgaa agccgttgtc   1500
gatgaatttg ttgcagacta caaagatttc acgggcatta aactgaccgc caaaaaaggc   1560
gcggccgaag cgggtgcctt taatttcgtg aaaaccgaca gcacggcagc tattgcgcag   1620
ctgggcgatg aaggttatac catggacatc cgcgctgatc gtgtggttgc gaaatcatcg   1680
agcgtgaccg gtaacatgta cgctatgcaa acgattctgc agatgaccaa acaagatgcg   1740
aatggctttg ttatcggtag catgcgcgac tatccgcgtt tcaccacgcg tggtctgctg   1800
ctggatgtcg cacgtaaacc ggtgtctctg gaaatgatgc gcgaaattac gcgcaccatg   1860
cgttattaca aaatgaacga ctttcaggcg cacctgtctg ataactatat cttcctggaa   1920
aattacggca aaggtgacaa cgaagatgaa gcatttaaag cttatgatgc gttccgtctg   1980
gaatctagtc tgacgaatga caaaggtgaa agtccgaccg cagaagatta ctccatcagc   2040
aagaaaacct tcaaacaatt catccaggat gaacgcgcgc tgggcatgaa cgtcgtgccg   2100
gaaattgatg tgccggcaca tgctaatagc tttaccaaaa tctggccgga actgatggtg   2160
aaaggccgtg tctcaccgat taactcgaat cgcccgctga tcgaccacct ggatgttagt   2220
aaaccggaaa ccatcgcgaa aatcaaagaa atcttcgacg attacacgaa aggtgacgat   2280
ccgaccttcg actccgatac cacggttcat attggcgccg atgaatttct gtataactac   2340
accgcatatc gtaaattcat caatgaaatt gtgccgtaca ttaaagatac gaacaccgtt   2400
cgcatgtggg gcggtctgac ctggatcaat gaccataaaa ccgaaatcac gaaagatgca   2460
atcgaaaacg tggaaatgaa tctgtggtca aaagactggg cggatggtct gcagatgtat   2520
aatatgggct acaaactgat caacaccatt gacgattatg gttacatggt gccgaatggc   2580
tcttatggtc gtgcgaacgc ctacggcgac ctgctgaata ttagccgtgt ctttgattct   2640
ttcgaaccga acaaagtgcg ctcctcaggc ggttatcagg cggttccgag cggcgacgat   2700
```

```
caaatgctgg gtgcggcctt tgctatttgg agtgacaata tcgataaatc ggcgagcggt    2760
ctgaccgaat ccgacctgta ttggcgcttt ttcgatgcca tgccgtttta cgcagaaaaa    2820
acgtgggcag ctaccggcaa agaaaagggt acggcggcca aactgaccgc actggcagct    2880
aaacagggca cgggtccgcg taccaacccg tattaccaag cgacctctaa aaatagtgtg    2940
tatgaaagct acgactttaa cgatggcctg gcagatgctt ctggcaatgg tcgcgacctg    3000
accattggcg atggtagcaa agcggccgtt aaagatcagt ctctgaaact ggctggcggt    3060
tcgagctatg cgaccagcaa actggataaa ctgggcaacg gtaatgaact gacgtttgac    3120
gtgaccctgc aacaggcagc taaaccgggt gacattctgt tcgaagcgga tgccccgtat    3180
ggcacccatg atatccgtgt tatggaaaac ggcaaactgg gttttacccg cgaactgtac    3240
aactactact tcgattacga actgccggtc ggtaaaacgg ttaccgtcac gattaaagtg    3300
gatcaacaga ccacgaaact gtatgttgac ggcgaatttg tcagtgatgc gaccggcaaa    3360
tacatcgata aaggtatcga aaagaaaacc ggtattacgg cagcaacctt cgcactgccg    3420
ctgcagcgca tcggttccaa aacctcagca atcaacggcg tgatcgataa cgtgatcgtt    3480
aaaaaatctg aagccgaaac ggatcagtat aacaaaagtt gctggaccgg taccacgaat    3540
tccgaaacgc aatataacga caccgaaggc ctgctgcgtt acgcgtttga taacaatccg    3600
agtaccattt ggcactccaa ctggaaaggt gcgacggata aactgaccgg ctctaatagt    3660
ttctatgccg aaattgatat gtgtcagaaa tacaccatca atcaatttag cttcacgccg    3720
cgtacctcgc aggacagcgg tcaagttacc aaagcggatc tgtacgtcaa agcaaacgct    3780
aatgacgaat ggaaacaggt ggccaccgat caagtttttg aagcctctcg tgcgaagaaa    3840
acctttatgt tcgatgaaca ggaagttcgc tatgtcaaat tcgtggcgaa atctagtaac    3900
gatggttggg tcgctgtgtc agaatttggc gtggcgaata accgtcctc aaccgttcgt    3960 gtcttcgtgg cagctgatcc ggcagaaggc ggtaccgttt cggtcgcagc agaaggtgaa    4020
accggtacgg acaccgccgt ggatgttgct tctggcgcga gtgtcaccgc gaaagccgtg    4080
gcagctgatg gctatcgctt tagtggttgg ttcaccacgg cctcagaaac ggcagtgtcg    4140
accgacgcga cgtacacctt tgcggccgat ggtaacacgg ccctgaccgc aaaattcacg    4200
aaagactcca ccccggatcc gggtccgaaa ccgacgatct cgagcattgc cgttaccaaa    4260
ccgacggtca ccgattataa agtgggtgac acgtttgatg caaccggtct ggccgtgacg    4320
gcaaccatgt ccgatggttc aacgaaaacc ctgacggccg cgaatacac gctgagcgca    4380 acccaggacg gtgcagctgt tgcactggat aaagcatttg ctaaagcggg taaagtcacc    4440
gtgacggtta ccgctaatgg caaaacggcg accttcgatg tcacggtgac cgctaaagac    4500
ccggatccga aaccggcgac gctgaaaagc attaaagtta cctctaaacc ggacaaaacc    4560
acgtatacgg tggatgaaac ctttgccaaa acgggcctgg cagttacggg tacctggtca    4620
gacggcaaaa ccgcgctgct gaaagatggt gaatacaaac tgtcggccgt ggacgcagat    4680
ggtaaaaccg ttgacctgac gaaaccgttt accgcggccg tgatgttac ggtcaccgtg    4740 acgtcaggca aactgaccga ttcgttcacc atcacggtta agccaaaaac cgtcacgccg    4800
gcaccgggtg ataacaaacc gggcgaaaat aaaccgggtg cggataaacc gaaaccgaat    4860
acgccggacg aagtcgcaaa acgggtgcc tcagtgtgag cggccgcgtc gacacgcaaa    4920
aaggccatcc gtcaggatgg ccttctgctt aatttgatgc ctggcagttt atggcgggcg    4980
tcctgcccgc caccctccgg gccgttgctt cgcaacgttc aaatccgctc ccggcggatt    5040
```

```
tgtcctactc aggagagcgt tcaccgacaa acaacagata aaacgaaagg cccagtcttt      5100
cgactgagcc tttcgtttta tttgatgcct ggcagttccc tactctcgca tggggagacc      5160
ccacactacc atcatgtatg aatatcctcc ttagttccta ttccgaaggg taatggcatc      5220
agggaatggc gaacgcgctc cccacactac catcatgtat gaatatcctc cttagttcct      5280
attccgaagt tcctattctc tagaaagtat aggaacttcg gtggaacgac gcgtaactca      5340
cgttaaggga ttttggtcat gatcagcacg tgttgacaat taatcatcgg catagtatat      5400
cggcatagta taatacgaca aggtgaggaa ctaaaccatg ccaagttga ccagtgccgt       5460
tccggtgctc accgcgcgcg acgtcgccgg agcggtcgag ttctggaccg accggctcgg      5520
gttctcccgg gacttcgtgg aggacgactt cgccggtgtg gtccgggacg acgtgaccct      5580
gttcatcagc gcggtccagg accaggtggt gccggacaac ccctggcct gggtgtgggt       5640
gcgcggcctg gacgagctgt acgccgagtg gtcggaggtc gtgtccacga acttccggga      5700
cgcctccggg ccggccatga ccgagatcgg cgagcagccg tggggcggg agttcgccct       5760
gcgcgacccg gccggcaact gcgtgcactt cgtggccgag gagcaggact gagtggcagg      5820
gcggggcgta aggcgcgcca tttaaatgaa gttcctattc cgaagttcct attctctaga      5880
aagtatagga acttcgaagc agctccagcc tacacaatcg ctcaagacgg aacccgcgct      5940
tggcaggaaa gtaataggga tagcagctcc agcctacaca atcgctcaag acgtgtaatg      6000
ctgcacaata accctgctgc a                                                6021

<210> SEQ ID NO 42
<211> LENGTH: 4543
<212> TYPE: DNA
<213> ORGANISM: Unknown
<220> FEATURE:
<223> OTHER INFORMATION: Transposon cassette.

<400> SEQUENCE: 42
ggccagatga ttaattccta atttttgttg acactctatc attgatagag ttattttacc        60
actccctatc agtgatagag aaaagtgaaa tgaatagttc gacaaaaatc tagaaataat       120
tttgtttaac tttaagaagg agatatacaa atgaccatga ttacggattc actggccgtc       180
gttttacaac gtcgtgactg ggaaaaccct ggcgttaccc aacttaatcg ccttgcagca       240
catccccctt tcgccagctg gcgtaatagc gaagaggccc gcaccgatcg cccttcccaa       300
cagttgcgca gcctgaatgg cgaatggcgc tttgcctggt ttccggcacc agaagcggtg      360
ccggaaagct ggctggagtg cgatcttcct gaggccgata ctgtcgtcgt cccctcaaac       420
tggcagatgc acggttacga tgcgcccatc tacaccaacg tgacctatcc cattacggtc       480
aatccgccgt ttgttcccac ggagaatccg acgggttgtt actcgctcac atttaatgtt      540
gatgaaagct ggctacagga aggccagacg cgaattattt ttgatggcgt taactcggcg       600
tttcatctgt ggtgcaacgg gcgctgggtc ggttacggcc aggacagtcg tttgccgtct      660
gaatttgacc tgagcgcatt tttacgcgcc ggagaaaacc gcctcgcggt gatggtgctg      720
cgctggagtg acggcagtta tctggaagat caggatatgt ggcggatgag cggcattttc      780
cgtgacgtct cgttgctgca taaaccgact acacaaatca gcgatttcca tgttgccact      840
cgctttaatg atgatttcag ccgcgctgta ctggaggctg aagttcagat gtgcggcgag      900
ttgcgtgact acctacgggt aacagttttct ttatggcagg gtgaaacgca ggtcgccagc     960
ggcaccgcgc ctttcggcgg tgaaattatc gatgagcgtg gtggttatgc cgatcgcgtc     1020
acactacgtc tgaacgtcga aaacccgaaa ctgtggagcg ccgaaatccc gaatctctat    1080
```

```
cgtgcggtgg ttgaactgca caccgccgac ggcacgctga ttgaagcaga agcctgcgat    1140
gtcggtttcc gcgaggtgcg gattgaaaat ggtctgctgc tgctgaacgg caagccgttg    1200
ctgattcgag gcgttaaccg tcacgagcat catcctctgc atggtcaggt catggatgag    1260
cagacgatgg tgcaggatat cctgctgatg aagcagaaca actttaacgc cgtgcgctgt    1320
tcgcattatc cgaaccatcc gctgtggtac acgctgtgcg accgctacgg cctgtatgtg    1380
gtggatgaag ccaatattga aacccacggc atggtgccaa tgaatcgtct gaccgatgat    1440
ccgcgctggc taccggcgat gagcgaacgc gtaacgcgaa tggtgcagcg cgatcgtaat    1500
cacccgagtg tgatcatctg gtcgctgggg aatgaatcag gccacggcgc taatcacgac    1560
gcgctgtatc gctggatcaa atctgtcgat ccttcccgcc cggtgcagta tgaaggcggc    1620
ggagccgaca ccacgccacc gatattatt  tgcccgatgt acgcgcgcgt ggatgaagac    1680
cagcccttcc cggctgtgcc gaaatggtcc atcaaaaaat ggctttcgct acctggagag    1740
acgcgcccgc tgatcctttg cgaatacgcc cacgcgatgg gtaacagtct ggcggtttc    1800 gctaaatact ggcaggcgtt tcgtcagtat ccccgtttac agggcggctt cgtctgggac    1860
tgggtggatc agtcgctgat taaatatgat gaaaacggca cccgtggtc ggcttacggc    1920 ggtgattttg gcgatacgcc gaacgatcgc cagttctgta tgaacggtct ggtcttgcc    1980 gaccgcacgc cgcatccagc gctgacggaa gcaaaacacc agcagcagtt tttccagttc    2040
cgtttatccg ggcaaaccat cgaagtgacc agcgaatacc tgttccgtca tagcgataac    2100
gagctcctgc actggatggt ggcgctggat ggtaagccgc tggcaagcgg tgaagtgcct    2160
ctggatgtcg ctccacaagg taaacagttg attgaactgc tgaactacc gcagccggag    2220 agcgccgggg aactctggct cacagtacgc gtagtgcaac cgaacgcgac cgcatggtca    2280
gaagccggac acatcagcgc ctggcagcag tggcgtctgg ctgaaaacct cagcgtgaca    2340
ctccccgccg cgtcccacgc catcccgcat ctgaccacca gcgaaatgga ttttgcatc    2400 gagctgggta ataagcgttg gcaatttaac cgccagtcag gctttctttc acagatgtgg    2460
attggcgata aaaaacaact gctgacgccg ctgcgcgatc agttcacccg tgcaccgctg    2520
gataacgaca ttggcgtaag tgaagcgacc cgcattgacc ctaacgcctg ggtcgaacgc    2580
tggaaggcgg cgggccatta ccaggccgaa gcagcgttgt tgcagtgcac ggcagataca    2640
cttgctgatg cggtgctgat tacgaccgct cacgcgtggc agcatcaggg gaaaaccttg    2700
tttatcagcc ggaaaaccta ccggattgat ggtagtggtc aaatggcgat taccgttgat    2760
gttgaagtgc cgagcgatac accgcatccg gcgcggattg gcctgaactg ccagctggcg    2820
caggtagcag agcgggtaaa ctggctcgga ttagggccgc aagaaaacta tcccgaccgc    2880
cttactgccg cctgttttga ccgctgggat ctgccattgt cagacatgta taccccgtac    2940
gtcttcccga gcgaaaacgg tctgcgctgc gggacgcgcg aattgaatta tggcccacac    3000
cagtggcgcg cgacttcca gttcaacatc agccgctaca gtcaacagca actgatggaa    3060
accagccatc gccatctgct gcacgcggaa gaaggcacat ggctgaatat cgacggtttc    3120
catatgggga ttggtggcga cgactcctgg agccgtcag tatcggcgga attccagctg    3180
agcgccggtc gctaccatta ccagttggtc tggtgtcaaa aataaaataa ctagcataac    3240 cccttgggc  ctctaaacgg gtcttgaggg gtttttttgct gaaaccaatt tgcctggcgg    3300
cagtagcgcg gtggtcccac ctgacccat  gccgaactca gaagtgaaac gccgtagcgc    3360
cgatggtagt gtgggtctc  cccatgcgag agtagggaac tgccaggcat caaataaaac    3420
```

| | |
|---|---|
| gaaaggctca gtcgaaagac tgggcctttc gggatccagg ccggcctgtt aacgaattaa | 3480 |
| tcttccgcgg cggtatcgat aagcttgata tcgaattccg aagttcctat tctctagaaa | 3540 |
| gtataggaac ttcaggtctg aagaggagtt tacgtccagc caagctagct tggctgcagg | 3600 |
| tcgtcgaaat tctacgatct cggcttgaac gaattgttag gtggcggtac ttgggtcgat | 3660 |
| atcaaagtgc atcacttctt cccgtatgcc caactttgta tagagagcca ctgcgggatc | 3720 |
| gtcaccgtaa tctgcttgca cgtagatcac ataagcacca agcgcgttgg cctcatgctt | 3780 |
| gaggagattg atgagcgcgg tggcaatgcc ctgcctccgg tgctcgccgg agactgcgag | 3840 |
| atcatagata tagatctcac tacgcggctg ctcaaacctg gcagaacgt aagccgcgag | 3900 |
| agcgccaaca accgcttctt ggtcgaaggc agcaagcgcg atgaatgtct tactacggag | 3960 |
| caagttcccg aggtaatcgg agtccggctg atgttgggag taggtggcta cgtctccgaa | 4020 |
| ctcacgaccg aaaagatcaa gagcagcccg catggatttg acttggtcag ggccgagcct | 4080 |
| acatgtgcga atgatgccca tacttgagcc acctaacttt gttttagggc gactgccctg | 4140 |
| ctgcgtaaca tcgttgctgc tgcgtaacat cgttgctgct ccataacatc aaacatcgac | 4200 |
| ccacggcgta acgcgcttgc tgcttggatg cccgaggcat agactgtaca aaaaaacagt | 4260 |
| cataacaagc catgaaaacc gccactgcgc cgttaccacc gctgcgttcg gtcaaggttc | 4320 |
| tggaccagtt gcgtgagcgc atacgctact tgcattacag tttacgaacc gaacaggctt | 4380 |
| atgtcaactg ggttcgtgcc ttcatccgtt tccacggtgt gcgctgcact tgaacgtgtg | 4440 |
| gcctaatgag gggatcaatt ctctagagct cgctgatcag aagttcctat tctctagaaa | 4500 |
| gtataggaac ttcgatggcg cctcatccct gaagccaata ggg | 4543 |

<210> SEQ ID NO 43
<211> LENGTH: 5692
<212> TYPE: DNA
<213> ORGANISM: Unknown
<220> FEATURE:
<223> OTHER INFORMATION: Transposon cassette.

<400> SEQUENCE: 43

| | |
|---|---|
| ggccagatga ttaattccta atttttgttg acactctatc attgatagag ttattttacc | 60 |
| actccctatc agtgatagag aaaagtgaaa tgaatagttc gacaaaaatc tagaaataat | 120 |
| tttgtttaac tttaagaagg agatatacaa atggaacatc gtgccttcaa atggccgcaa | 180 |
| ccgctggctg gtaataaacc gcgcatctgg tatggtggtg actataaccc ggatcaatgg | 240 |
| ccggaagaag tctgggatga agacgtgca ctgatcagc aagctggcgt gaacctggtg | 300 |
| agtgttgcga tttttagctg ggccaaactg gaaccggaag aaggtgtgta tgatttcgac | 360 |
| tggctggatc gtgttattga caaactgggc aaagcgggta tcgccgttga tctggcctca | 420 |
| ggtaccgcat cgccgccgat gtggatgacc caggcgcatc cggaaatcct gtgggtggat | 480 |
| tatcgtggcg acgtttgtca gccgggtgcc cgtcaacact ggcgtgccac cagcccggtg | 540 |
| tttctggatt acgcgctgaa cctgtgtcgc aaaatggccg aacattataa agataatccg | 600 |
| tacgtggtta gctggcatgt ttctaacgaa tatgctgcc acaatcgttt tgattactca | 660 |
| gaagacgcag aacgcgcttt ccagaaatgg tgtgagaaaa aatatggcac gattgatgca | 720 |
| gtgaatgacg cttggggtac gcgttttggg gcccaacgta tgaacaattt ctcggaaatt | 780 |
| atcccgcgc gcttcatcgg cgatggtaac tttatgaatc cgggtaaact gctggattgg | 840 |
| aaacgttta gctctgatgc gctgctggac ttctataaag cggaacgcga tgccctgctg | 900 |
| gaaattgcac cgaaaccgca gaccacgaac tttatggtct ctgcgggctg cacggtgctg | 960 |

```
gattacgaca aatggggtca tgatgttgac ttcgtcagca atgatcatta ttttctccg    1020 ggcgaagcac acttcgatga aatggcttac gcggcatgtc tgaccgatgg tattgcccgt    1080
aaaaacccgt ggttcctgat ggaacatagt acgtccgccg tgaactggcg tccgaccaat    1140
tatcgcctgg aaccgggcga actggttcgt gatagcctgg cacacctggc tatgggtgcg    1200
gacgccattt gctactttca gtggcgccaa tcaaaagcag gcgctgaaaa atggcattcg    1260
gcaatggttc cgcacgctgg tccgattct cagatcttcc gcgacgtctg tgaactgggc    1320
gcggatctga ataaactggc cgacgaaggt ctgctgagta ccaaactggt gaaatccaaa    1380
gtggcgattg ttttgatta tgaaagtcag tgggccaccg aacataccgc aacgccgacc    1440
caagaagtgc gtcactggac cgaaccgctg gattggtttc gtgccctggc ggataatggt    1500
ctgaccgccg atgttgtgcc ggttcgcggt ccgtgggatg aatatgaagc cgttgtcctg    1560
ccgtcactgg caattctgtc ggaacaaacc acgcgtcgcg ttcgtgaata cgtcgccaat    1620
ggcggtaaac tgtttgtgac gtattacacc ggcctggttg atgaccgcga tcatgtctgg    1680
ctgggcggtt atccgggcag catccgtgat gtggttggtg tccgcgtgga agaatttgca    1740
ccgatgggca cggatgctcc gggtaccatg gaccatctgg atctggacaa cggtaccgtg    1800
gcacacgatt tcgctgacgt gattacgagc gttgcggata ccgcccacgt cgtggcgtct    1860
tttaaagccg ataaatggac gggcttcgac ggtgcaccgg ctatcaccgt caatgatttt    1920
ggcgacggta agcggcttac gtgggtgcc cgtctgggtc gtgaaggtct ggcaaaaagt    1980
ctgccggctc tgctggaaga actgggcatt gaaaccagcg ccgaagatga ccgtggtgaa    2040
gtcctgcgtg tggaacgcgc agatgaaacg ggcgaaaacc attttgtgtt cctgtttaat    2100
cgcacccacg atgttgccgt tgtcgacgtc gaaggtgaac cgctggttgc aagcctggct    2160
caggtcaatg aaagtgaaca caccgctgct atccaaccga acggcgtgct ggtcgtcaaa    2220
ctgtaaacta gcataacccc ttggggcctc taaacgggtc ttgaggggtt ttttgctgaa    2280
accaatttgc ctggcggcag tagcgcggtg gtcccacctg accccatgcc gaactcagaa    2340
gtgaaacgcc gtagcgccga tggtagtgtg gggtctcccc atgcgagagt agggaactgc    2400
caggcatcaa ataaaacgaa aggctcagtc gaaagactgg gcctttcggg atccaggccg    2460
gcctgttaac gaattaatct tccgcggcgg tatcgataag cttgatggcg aaaggggat    2520 gtgctgcaag gcgattaagt tgggtaacgc cagggttttc ccagtcacga cgttgtaaaa    2580
cgacggccag tgaattcgag ctcggtacct accgttcgta atgtatgc tatacgaagt    2640 tatcgagctc tagagaatga tccctcctg ccactcatcg cagtactgtt gtattcatta    2700
agcatctgcc gacatggaag ccatcacaaa cggcatgatg aacctgaatc gccagcggca    2760 tcagcaccctt gtcgccttgc gtataatatt tgcccatggt gaaaacgggg gcgaagaagt    2820
tgtccatatt ggccacgttt aaatcaaaac tggtgaaact cacccaggga ttggctgaga    2880
cgaaaaacat attctcaata aaccctttag gaaataggc caggttttca ccgtaacacg    2940
ccacatcttg cgaatatatg tgtagaaact gccggaaatc gtcgtggtat tcactccaga    3000
gcgatgaaaa cgtttcagtt tgctcatgga aacggtgta acaagggtga acactatccc    3060
atatcaccag ctcaccgtct ttcattgcca tacgtaattc cggatgagca ttcatcaggc    3120
gggcaagaat gtgaataaag gccggataaa acttgtgctt attttttcttt acggtcttta    3180 aaaaggccgt aatatccagc tgaacggtct ggttataggt acattgagca actgactgaa    3240
atgcctcaaa atgttcttta cgatgccatt gggatatatc aacggtggta tatccagtga    3300
```

```
tttttttctc catttagct tccttagctc ctgaaaatct cgacaactca aaaaatacgc    3360
ccggtagtga tcttatttca ttatggtgaa agttggaacc tcttacgtgc cgatcaacgt    3420
ctcattttcg ccaaaagttg gcccagggct tcccggtatc aacagggaca ccaggattta    3480
tttattctgc gaagtgatct tccgtcacag gtagaatttc gacgacctgc agccaagcat    3540
aacttcgtat aatgtatgct atacgaacgg taggatcctc tagagtcgac ctgcaggcat    3600
gatgtatgaa tatcctcctt agttcctatt ccgaagttcc tattctctag aaagtatagg    3660
aacttcggcg acgtctaaga aaccattatt atcatgacat taacctataa aataggcgt    3720
atcacgaggc cctttcgtct tcaagaattc tcatgtttga cagcttatca tcgataagct    3780
ttaatgcggt agtttatcac agttaaattg ctaacgcagt caggcaccgt gtatgaaatc    3840
taacaatgcg ctcatcgtca tcctcggcac cgtcaccctg gatgctgtag gcataggctt    3900
ggttatgccg gtactgccgg gcctcttgcg ggatatcgtc cattccgaca gcatcgccag    3960
tcactatggc gtgctgctag cgctatatgc gttgatgcaa tttctatgcg cacccgttct    4020
cggagcactg tccgaccgct ttggccgccg cccagtcctg ctcgcttcgc tacttggagc    4080
cactatcgac tacgcgatca tggcgaccac acccgtcctg tggatcctct acgccggacg    4140
catcgtggcc ggcatcaccg cgccacagg tgcggttgct ggcgcctata tcgccgacat    4200
caccgatggg gaagatcggg ctcgccactt cgggctcatg agcgcttgtt tcggcgtggg    4260
tatggtggca ggccccgtgg ccgggggact gttgggcgcc atctccttgc atgcaccatt    4320
ccttgcggcg gcggtgctca acggcctcaa cctactactg gctgcttcc taatgcagga    4380
gtcgcataag ggagagcgtc gaccgatgcc cttgagagcc ttcaacccag tcagctcctt    4440
ccggtgggcg cggggcatga ctatcgtcgc cgcacttatg actgtcttct ttatcatgca    4500
actcgtagga caggtgccgg cagcgctctg ggtcattttc ggcgaggacc gctttcgctg    4560
gagcgcgacg atgatcggcc tgtcgcttgc ggtattcgga atcttgcacg ccctcgctca    4620
agccttcgtc actggtcccg ccaccaaacg tttcggcgag aagcaggcca ttatcgccgg    4680
catggcggcc gacgcgctgg gctacgtctt gctggcgttc gcgacgcgag gctggatggc    4740
cttccccatt atgattcttc tcgcttccgg cggcatcggg atgcccgcgt tgcaggccat    4800
gctgtccagg caggtagatg acgaccatca gggacagctt caaggatcgc tcgcggctct    4860
taccagccta acttcgatca ctggaccgct gatcgtcacg gcgatttatg ccgcctcggc    4920
gagcacatgg aacgggttgg catggattgt aggcgccgcc ctataccttg tctgcctccc    4980
cgcgttgcgt cgcggtgcat ggagccgggc cacctcgacc tgagtggcag gcggggcgt    5040
aaggcgcgcc atttaaatga agttcctatt ccgaagttcc tattctctag aaagtatagg    5100
aacttcgaag cagctccagc ctacacaatc gctcaagacg tgtaatgctg caatctgcat    5160
gcaagcttgg cactggccac gcaaaaaggc catccgtcag gatggccttc tgcttaattt    5220
gatgcctggc agtttatggc gggcgtcctg cccgccaccc tccgggccgt tgcttcgcaa    5280
cgttcaaatc cgctcccggc ggatttgtcc tactcaggag agcgttcacc gacaaacaac    5340
agataaaacg aaaggcccag tctttcgact gagcctttcg ttttatttga tgcctggcag    5400
ttccctactc tcgcatgggg agaccccaca ctaccatcgg ggggcatcg atgcaggtgg    5460
cacttttcgg ggaaatgtgc gcggaacccc tatttgttta ttttctaaa tacattcaaa    5520
tatgtatccg ctcatgagac aataaccctg ctgcagaggc ctgcatgcaa gcttggcgta    5580
atcatggtca tagctgtttc ctgtgtgaaa ttgttatccg ctcacaattc cacacaacat    5640
acgagccgga agcataaagt gtaaagcctg ggtgcctaa tgagtgagct aa    5692
```

<210> SEQ ID NO 44
<211> LENGTH: 28
<212> TYPE: DNA
<213> ORGANISM: Unknown
<220> FEATURE:
<223> OTHER INFORMATION: PCR primer

<400> SEQUENCE: 44
aacgccgcca gcggtcgtca gactgtcg					28

<210> SEQ ID NO 45
<211> LENGTH: 28
<212> TYPE: DNA
<213> ORGANISM: Unknown
<220> FEATURE:
<223> OTHER INFORMATION: PCR primer

<400> SEQUENCE: 45
taagcagaag gccatcctga cggatggc					28

<210> SEQ ID NO 46
<211> LENGTH: 25
<212> TYPE: DNA
<213> ORGANISM: Unknown
<220> FEATURE:
<223> OTHER INFORMATION: PCR primer

<400> SEQUENCE: 46
gcggccgcgt cgacacgcaa aaagg					25

<210> SEQ ID NO 47
<211> LENGTH: 28
<212> TYPE: DNA
<213> ORGANISM: Unknown
<220> FEATURE:
<223> OTHER INFORMATION: PCR primer

<400> SEQUENCE: 47
agtctgcgcg tctttcaggg cttcatcg					28

<210> SEQ ID NO 48
<211> LENGTH: 31
<212> TYPE: DNA
<213> ORGANISM: Unknown
<220> FEATURE:
<223> OTHER INFORMATION: PCR primer

<400> SEQUENCE: 48
gatcccatgg aagttaaaat cattggtggt c					31

<210> SEQ ID NO 49
<211> LENGTH: 33
<212> TYPE: DNA
<213> ORGANISM: Unknown
<220> FEATURE:
<223> OTHER INFORMATION: PCR primer

<400> SEQUENCE: 49
gcgcggatcc ttacagtttc acccaagatt ccg					33

<210> SEQ ID NO 50
<211> LENGTH: 35
<212> TYPE: DNA
<213> ORGANISM: Unknown
<220> FEATURE:

<223> OTHER INFORMATION: PCR primer

<400> SEQUENCE: 50
tataccatgg cttttaaggt ggtgcaaatt tgcgg                       35

<210> SEQ ID NO 51
<211> LENGTH: 39
<212> TYPE: DNA
<213> ORGANISM: Unknown
<220> FEATURE:
<223> OTHER INFORMATION: PCR primer

<400> SEQUENCE: 51
aattcggatc cttaagcgtt atacttttgg gatttcacc                   39

<210> SEQ ID NO 52
<211> LENGTH: 58
<212> TYPE: DNA
<213> ORGANISM: Unknown
<220> FEATURE:
<223> OTHER INFORMATION: PCR primer

<400> SEQUENCE: 52
ctgtctctta tacacatctc ctgaaattgg ccagatgatt aattcctaat ttttgttg    58

<210> SEQ ID NO 53
<211> LENGTH: 50
<212> TYPE: DNA
<213> ORGANISM: Unknown
<220> FEATURE:
<223> OTHER INFORMATION: PCR primer

<400> SEQUENCE: 53
ctgtctctta tacacatctc agcattacac gtcttgagcg attgtgtagg       50

<210> SEQ ID NO 54
<211> LENGTH: 47
<212> TYPE: DNA
<213> ORGANISM: Unknown
<220> FEATURE:
<223> OTHER INFORMATION: PCR primer

<400> SEQUENCE: 54
ctgtctctta tacacatctg ggaattgatt ctggtaccaa atgagtc          47

<210> SEQ ID NO 55
<211> LENGTH: 45
<212> TYPE: DNA
<213> ORGANISM: Unknown
<220> FEATURE:
<223> OTHER INFORMATION: PCR primer

<400> SEQUENCE: 55
ctgtctctta tacacatctc cccaggcttt acactttatg cttcc            45

<210> SEQ ID NO 56
<211> LENGTH: 54
<212> TYPE: DNA
<213> ORGANISM: Unknown
<220> FEATURE:
<223> OTHER INFORMATION: PCR primer

<400> SEQUENCE: 56
ctgtctctta tacacatctt tactcagcaa taaactgata ttccgtcagg ctgg   54

-continued

```
<210> SEQ ID NO 57
<211> LENGTH: 55
<212> TYPE: DNA
<213> ORGANISM: Unknown
<220> FEATURE:
<223> OTHER INFORMATION: PCR primer

<400> SEQUENCE: 57
ctgtctctta tacacatctt tccgttaacg tcggtagtgc tgaccttgcc ggagg         55
```